(12) United States Patent
Buschmann et al.

(10) Patent No.: US 10,786,492 B2
(45) Date of Patent: *Sep. 29, 2020

(54) FORMYLATED N-HETEROCYCLIC DERIVATIVES AS FGFR4 INHIBITORS

(71) Applicant: Novartis AG, Basel (CH)

(72) Inventors: Nicole Buschmann, Basel (CH); Robin Alec Fairhurst, Basel (CH); Pascal Furet, Thann (FR); Thomas Knoepfel, Rheinfelden (CH); Catherine Leblanc, Basel (CH); Robert Mah, Muttenz (CH)

(73) Assignee: NOVARTIS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/211,139

(22) Filed: Dec. 5, 2018

(65) Prior Publication Data
US 2019/0105309 A1 Apr. 11, 2019

(51) Int. Cl.
| C07D 401/12 | (2006.01) |
| C07D 401/14 | (2006.01) |
| A61K 31/444 | (2006.01) |
| A61K 31/4427 | (2006.01) |
| C07D 213/75 | (2006.01) |
| C07D 405/14 | (2006.01) |
| A61P 35/00 | (2006.01) |
| A61K 31/497 | (2006.01) |

(52) U.S. Cl.
CPC ........ A61K 31/444 (2013.01); A61K 31/4427 (2013.01); A61K 31/497 (2013.01); A61P 35/00 (2018.01); C07D 213/75 (2013.01); C07D 401/12 (2013.01); C07D 401/14 (2013.01); C07D 405/14 (2013.01)

(58) Field of Classification Search
CPC .................... C07D 401/12; C07D 401/14
See application file for complete search history.

(56) References Cited

FOREIGN PATENT DOCUMENTS

| WO | 2000078731 A1 | 12/2000 |
| WO | 200437808 A1 | 5/2004 |
| WO | 2006000420 A1 | 1/2006 |
| WO | 2008065282 A2 | 6/2008 |

Primary Examiner — Brian E McDowell
(74) Attorney, Agent, or Firm — David K. Cheung

(57) ABSTRACT

The present invention provides a compound of formula (I) or a pharmaceutically acceptable salt thereof;

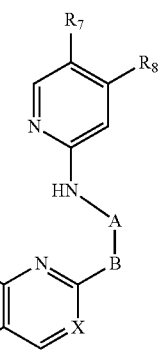

(I)

a method for manufacturing said compound, and its therapeutic uses. The present invention further provides a combination of pharmacologically active agents and a pharmaceutical composition comprising said compound.

1 Claim, No Drawings

FORMYLATED N-HETEROCYCLIC DERIVATIVES AS FGFR4 INHIBITORS

CROSS-REFERENCE TO RELATED APPLICATIONS

This application is a divisional of U.S. patent application Ser. No. 15/561,189, filed Sep. 25, 2017, issued as U.S. Pat. No. 10,189,813, which is a U.S. National Phase application filed under 35 U.S.C. § 371 claiming benefit to International Patent Application No. PCT/IB2016/051631 filed on Mar. 23, 2016, which is entitled to priority under 35 U.S.C. § 119(b) to foreign application EP 15160735.5, filed Mar. 25, 2015, each of which is hereby incorporated by reference in its entirety.

FIELD OF THE INVENTION

The invention provides formylated N-heterocyclic compounds, the use thereof for inhibiting FGFR4 and methods of treating disease using said compounds.

BACKGROUND OF THE INVENTION

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz, Novartis Found Symp 232: 63-76; discussion 76-80, 272-82 (2001)).

The biological action of FGFs is mediated by specific cell surface receptors belonging to the Receptor Protein Tyrosine Kinase (RPTK) family of protein kinases. These proteins consist of an extracellular ligand binding domain, a single transmembrane domain and an intracellular tyrosine kinase domain which undergoes phosphorylation upon binding of FGF. Four FGFRs have been identified to date: FGFR1 (also called Flg, fms-like gene, flt-2, bFGFR, N-bFGFR or Cek1), FGFR2 (also called Bek-Bacterial Expressed Kinase-, KGFR, Ksam, Ksaml and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain III), with an acidic region between Ig domains (the "acidic box" domain), a transmembrane domain, and intracellular kinase domains (Ullrich and Schlessinger, Cell 61: 203, 1990; Johnson and Williams (1992) Adv. Cancer Res. 60: 1-41). The distinct FGFR isoforms have different binding affinities for the different FGF ligands.

Alterations in FGFRs have been associated with a number of human cancers including myeloma, breast, stomach, colon, bladder, pancreatic and hepatocellular carcinomas. Recently, it was reported that FGFR4 may play an important role in liver cancer in particular (PLoS One, 2012, volume 7, 36713). Other studies have also implicated FGFR4 or its ligand FGF19 in other cancer types including breast, glioblastoma, prostate, rhabdomyosarcoma, gastric, ovarian, lung, colon (Int. J. Cancer 1993; 54:378-382; Oncogene 2010; 29:1543-1552; Cancer Res 2010; 70:802-812; Cancer Res 2011; 71:4550-4561; Clin Cancer Res 2004; 10:6169-6178; Cancer Res 2013; 73:2551-2562; Clin Cancer Res 2012; 18:3780-3790; J. Clin. Invest. 2009; 119:3395-3407; Ann Surg Oncol 2010; 17:3354-61; Cancer 2011; 117:5304-13; Clin Cancer Res 2013; 19:809-820; PNAS 2013; 110: 12426-12431; Oncogene 2008; 27:85-97).

Inhibitors of FGF receptors have been the subject of patent applications WO0078731, WO03099796 and WO006000420.

More specifically, therapies involving FGFR4 blocking antibodies have been described for instance in WO2009/009173, WO2007/136893, WO2012/138975, WO2010/026291, WO2008/052798 and WO2010/004204. WO2014/144737 and WO2014/011900 also describe low molecular weight FGFR4 inhibitors.

SUMMARY OF THE INVENTION

There is a continuing need to develop new FGFR4 inhibitors that are good drug candidates. Such candidates would find applications inter alia in the treatment of cancer, particularly in the treatment of liver cancer.

The invention provides compounds, pharmaceutically acceptable salts thereof, pharmaceutical compositions thereof and combinations thereof, which compounds are FGFR4 inhibitors. The invention further provides methods of treating, preventing, or ameliorating cancers comprising administering to a subject in need thereof an effective amount of a FGFR4 inhibitor.

Various embodiments of the invention are described herein.

Within certain aspects, provided herein is a compound of formula (I) or a pharmaceutically acceptable salt thereof:

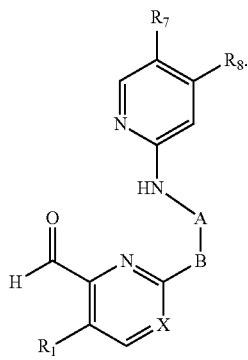

(I)

In another embodiment, the invention provides a pharmaceutical composition comprising a therapeutically effective amount of a compound according to the definition of formula (I), or a pharmaceutically acceptable salt thereof, or subformulae thereof (Ia), (Ib) and one or more pharmaceutically acceptable carriers.

In another embodiment, the invention provides a pharmaceutical composition comprising a therapeutically effective amount of a compound according to the definition of formula (I), or a pharmaceutically acceptable salt thereof, or subformulae thereof (Ia), (Ib) only.

In another embodiment, the invention provides a combination, in particular a pharmaceutical combination, comprising a therapeutically effective amount of the compound according to the definition of formula (I), or a pharmaceutically acceptable salt thereof, or subformulae thereof (Ia), (Ib) and one or more therapeutically active agent.

In a further embodiment, the invention relates to a method of inhibiting FGFR4 receptor activity in a subject, wherein the method comprises administering to the subject a therapeutically effective amount of the compound of formula (I) or subformulae thereof (Ia), (Ib) as defined herein or a pharmaceutically acceptable salt thereof.

In yet another embodiment, the invention relates to a method of treating a disorder or disease selected from cancer, e.g. liver cancer, breast cancer, glioblastoma, prostate cancer, rhabdomyosarcoma, gastric cancer, ovarian cancer, lung cancer or colon cancer comprising administering to the subject a therapeutically effective amount of the compound of formula (I) as defined herein or subformulae thereof (Ia), (Ib) or a pharmaceutically acceptable salt thereof.

DETAILED DESCRIPTION OF THE INVENTION

The invention provides a compound of formula (I) or a pharmaceutically acceptable salt thereof

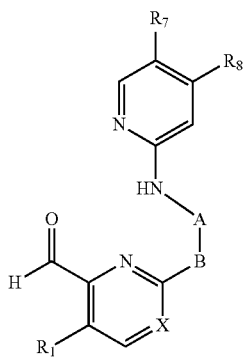

(I)

wherein
X is N or CH;
A is C(O) and B is $NR_5$ or
A and B together form part of a 5- or 6-membered aromatic ring wherein A is C and B is C or N;
$R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted once or more than once with $C_1$-$C_3$alkyl;
$R_2$ is $C_1$-$C_3$alkyl and $R_3$ is $C(O)C_1$-$C_3$alkyl
or
$R_2$ and $R_3$ together with the N to which they are attached form a saturated 5- or 6-membered ring optionally comprising one additional heteroatom selected from N, O or S, which ring is optionally substituted once or more than once with $R_4$;
$R_4$ is for each occurrence independently selected from $C_1$-$C_3$alkyl, $C_1$-$C_3$alkoxy or two $R_4$ attached at the same carbon atom form an oxo group;
$R_5$ is selected from hydrogen, $C_1$-$C_3$alkyl, $C_1$-$C_3$alkoxy$C_1$-$C_3$alkyl, $(CH_2)_{0-1}$—$R_6$;
$R_6$ is a 4-, 5-, or 6-membered saturated heterocyclic ring comprising at least one heteroatom selected from N, O, or S;
$R_7$ is selected from cyano, halo$C_1$-$C_3$alkyl;
$R_8$ is selected from hydrogen, $NR_9R_{10}$, $C_1$-$C_6$alkoxy;
$R_9$ is hydrogen;
$R_{10}$ is selected from $C_1$-$C_6$alkyl, hydroxy$C_1$-$C_6$alkyl, $C_1$-$C_4$alkoxy$C_1$-$C_6$alkyl.

Unless specified otherwise, the terms "compounds of the present invention" or "compounds of the invention" refer to compounds of formula (I), (Ia), (Ib) and salts thereof, as well as all stereoisomers (including diastereoisomers and enantiomers), rotamers, tautomers, isomeric internal addition products and isotopically labeled compounds (including deuterium substitutions), as well as inherently formed moieties.

In particular, the compounds of formula (I), (Ia), (Ib) are able to readily form tautomers and isomeric internal addition products as depicted below.

For instance, compounds of the invention where $R_1$ is hydroxymethyl, $CO_2H$, e.g. compounds (I-1) or (I-2) respectively may be in the form as depicted below (compounds (I-1a) and (I-2a) respectively).

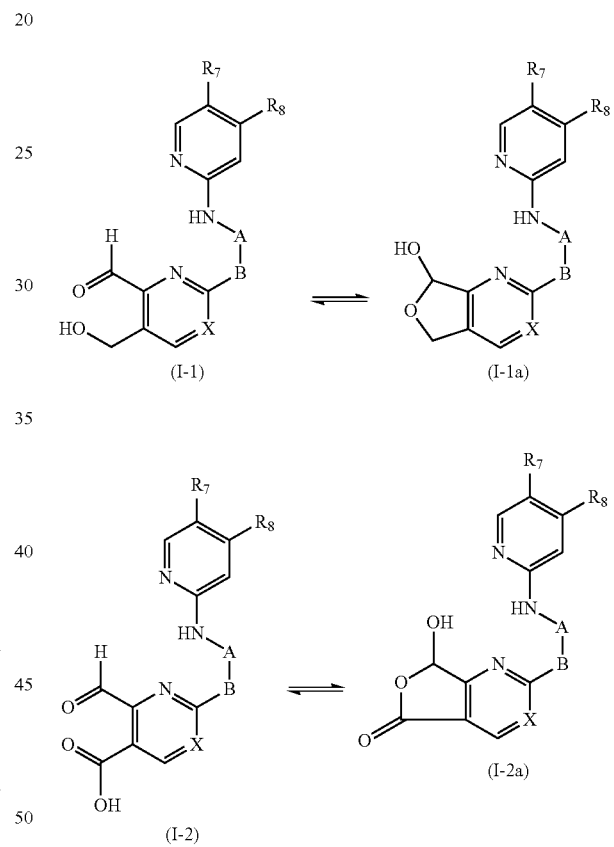

Thus, the compounds (I-1), (I-2) and their respective isomers (I-1a), (I-2a), wherein A, B, X, $R_7$ and $R_8$ are as defined herein, also form part of the invention.

The presence of tautomers or isomeric internal additional products, and equilibrium mixtures between these species can be identified by a person of skill in the art with tools such as NMR. As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_1$-$C_3$alkyl" or "$C_1$-$C_4$alkyl" are to be construed accordingly. Examples of $C_1$-$C_6$alkyl include, but are not limited to, methyl, ethyl, n-propyl, 1-methylethyl (iso-propyl), n-butyl, n-pentyl and 1,1-dimethylethyl (t-butyl).

As used herein, the term "hydroxyC$_1$-C$_6$alkyl" refers to a radical of formula —R$_a$—OH, wherein R$_a$ is C$_{1-6}$alkyl as defined above. Examples of hydroxyC$_1$-C$_6$alkyl include, but are not limited to, hydroxy-methyl, 2-hydroxy-ethyl, 2-hydroxy-propyl, 3-hydroxy-propyl and 5-hydroxy-pentyl.

As used herein, the term "C$_1$-C$_6$alkoxy" refers to a radical of the formula —OR$_a$ where R$_a$ is a C$_1$-C$_6$alkyl radical as generally defined above. The term "C$_1$-C$_3$alkoxy" is to be construed accordingly. Examples of C$_1$-C$_6$alkoxy include, but are not limited to, methoxy, ethoxy, propoxy, iso-propoxy, butoxy, isobutoxy, pentoxy, and hexoxy.

As used herein, the term "C$_1$-C$_4$alkoxyC$_1$-C$_6$alkyl" refers to a radical of the formula —R$_b$—O—R$_a$ where R$_a$ is a C$_1$-C$_4$alkyl radical and R$_b$ is a C$_1$-C$_6$alkyl radical as defined above. The term "C$_1$-C$_3$alkoxyC$_1$-C$_3$alkyl" is to be construed accordingly. The oxygen atom may be bonded to any carbon atom in either alkyl radical. Examples of C$_1$-C$_4$alkoxyC$_1$-C$_6$alkyl include, but are not limited to, methoxy-methyl, methoxy-ethyl, ethoxy-ethyl, 1-ethoxy-propyl and 2-methoxy-butyl.

"Halogen" or "halo" refers to bromo, chloro, fluoro or iodo.

As used herein, the term "halogenC$_1$-C$_3$alkyl" or "haloC$_1$-C$_3$alkyl" refers to C$_1$-C$_3$alkyl radical, as defined above, substituted by one or more halo radicals, as defined above. Examples of halogenC$_1$-C$_3$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "a 4-, 5-, or 6-membered saturated heterocyclic ring comprising at least one heteroatom selected from N, O, or S" includes as example, but is not limited to, tetrahydrofuran.

As used herein, the term "a saturated 5- or 6-membered ring optionally comprising one additional heteroatom selected from N, O or S" in relation to the embodiments where R$^2$ and R$^3$ together with the N atom to which they are attached form said ring, includes as examples, but is not limited to, pyrrolidine, oxazolidine, piperazine, morpholine, thiomorpholine rings. Preferably, it includes pyrrolidine and piperazine rings.

As used herein, the term "a 5- or 6-membered aromatic ring" includes 5-membered heterocyclic aromatic rings comprising one or more heteroatoms selected from N, O or S. Examples include, but are not limited to, imidazole, pyrazole. It also includes 6-membered carbocyclic aromatic rings such as phenyl for example or heterocyclic aromatic rings comprising one or more heteroatoms selected from N, O or S, such as pyridine for example.

As used herein, the term "more than once" when referring to substituent R$^4$, includes 2, 3, 4, 5, or 6 times. Preferably, it includes 2 or 3 times.

As used herein, the term "FGFR4" refers to fibroblast growth factor receptor 4, also known as CD334, JTK2, TKF.

In an embodiment of the invention, there is provided a compound of formula (Ia) or a pharmaceutically acceptable salt thereof

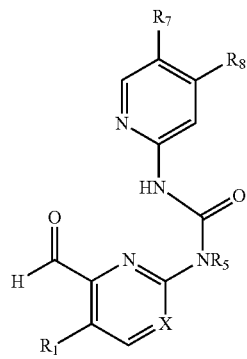

(Ia)

wherein

X is N or CH;

R$_1$ is selected from hydrogen, hydroxyC$_1$-C$_3$alkyl, haloC$_1$-C$_3$alkyl, CO$_2$H, CH$_2$NR$_2$R$_3$, a 5-membered aromatic heterocyclic ring comprising at least one heteroatom selected from N, O or S, which ring is optionally substituted once or more than once with C$_1$-C$_3$alkyl;

R$_2$ is C$_1$-C$_3$alkyl and R$_3$ is C(O)C$_1$-C$_3$alkyl or

R$_2$ and R$_3$ together with the N to which they are attached form a saturated 5- or 6-membered ring optionally comprising one additional heteroatom selected from N, O or S, which ring is optionally substituted once or more than once with R$_4$;

R$_4$ is for each occurrence independently selected from C$_1$-C$_3$alkyl, C$_1$-C$_3$alkoxy or two R$_4$ attached at the same carbon atom form an oxo group;

R$_5$ is selected from hydrogen, C$_1$-C$_3$alkyl, C$_1$-C$_3$alkoxyC$_1$-C$_3$alkyl, (CH$_2$)$_{0-1}$—R$_6$;

R$_6$ is a 4-, 5-, or 6-membered saturated heterocyclic ring comprising at least one heteroatom selected from N, O, or S;

R$_7$ is selected from cyano, haloC$_1$-C$_3$alkyl;

R$_8$ is selected from hydrogen, NR$_9$R$_{10}$, C$_1$-C$_6$alkoxy;

R$_9$ is hydrogen;

R$_{10}$ is selected from C$_1$-C$_6$alkyl, hydroxyC$_1$-C$_6$alkyl, C$_1$-C$_4$alkoxyC$_1$-C$_6$alkyl.

In an embodiment of the invention, there is provided a compound of formula (Ia-1) or a pharmaceutically acceptable salt thereof

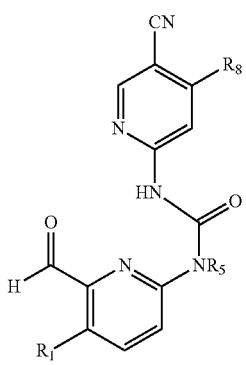

(Ia-1)

wherein

R$_1$ is selected from hydrogen, hydroxyC$_1$-C$_3$alkyl, haloC$_1$-C$_3$alkyl, CO$_2$H, CH$_2$NR$_2$R$_3$, a 5-membered aromatic heterocyclic ring comprising at least one heteroatom selected from N, O or S, which ring is optionally substituted with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy or two $R_4$ attached at the same carbon atom form an oxo group;

$R_5$ is selected from hydrogen, $C_1$-$C_3$alkyl, $C_1$-$C_3$alkoxy$C_1$-$C_3$alkyl, $(CH_2)_{0-1}$—$R_6$;

$R_6$ is a 4-, 5-, or 6-membered saturated heterocyclic ring comprising at least one heteroatom selected from N, O, or S;

$R_8$ is selected from hydrogen, $NR_9R_{10}$, $C_1$-$C_3$alkoxy;

$R_9$ is hydrogen;

$R_{10}$ is selected from $C_1$-$C_3$alkyl, hydroxy$C_1$-$C_4$alkyl, $C_1$-$C_3$alkoxy$C_1$-$C_3$alkyl.

In an embodiment of the invention, there is provided a compound of formula (Ib) or a pharmaceutically acceptable salt thereof

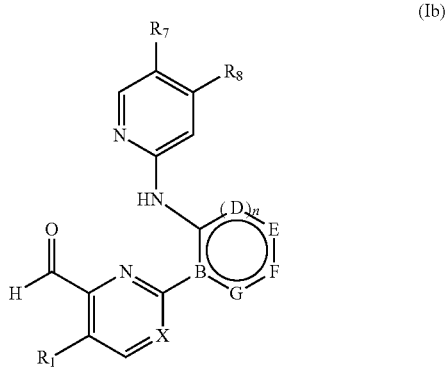

(Ib)

wherein n is 0 or 1;

B is C or N;

D, E, F, G are each independently selected from CH or N, provided that when n is 0, at least one of B, E, F or G is N;

X is N or CH;

$R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted once or more than once with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy or two $R_4$ attached at the same carbon atom form an oxo group;

$R_7$ is selected from cyano, halo$C_1$-$C_3$alkyl;

$R_8$ is selected from hydrogen, $NR_9R_{10}$, $C_1$-$C_6$alkoxy;

$R_9$ is hydrogen;

$R_{10}$ is selected from $C_1$-$C_6$alkyl, hydroxy$C_1$-$C_6$alkyl, $C_1$-$C_4$alkoxy$C_1$-$C_6$alkyl.

In an embodiment of the invention, there is provided a compound of formula (Ib-1) or a pharmaceutically acceptable salt thereof

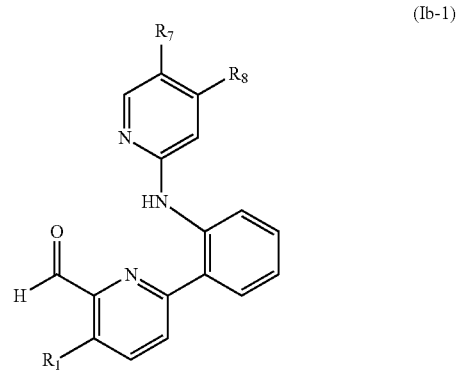

(Ib-1)

wherein $R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy or two $R_4$ attached at the same carbon atom form an oxo group;

$R_7$ is selected from cyano, halo$C_1$-$C_3$alkyl;

$R_8$ is selected from hydrogen, $NR_9R_{10}$, $C_1$-$C_3$alkoxy;

$R_9$ is hydrogen;

$R_{10}$ is selected from $C_1$-$C_3$alkoxy$C_1$-$C_3$alkyl, hydroxy$C_1$-$C_4$alkyl, $C_1$-$C_3$alkyl.

In an embodiment of the invention, there is provided a compound of formula (Ib-2) or a pharmaceutically acceptable salt thereof

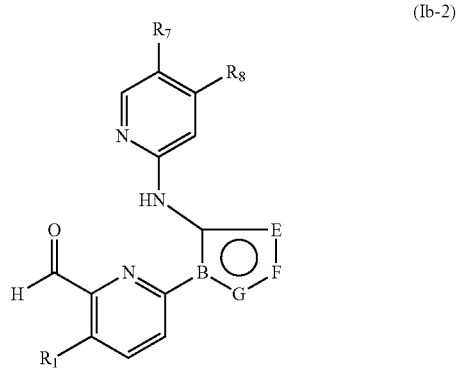

(Ib-2)

wherein

B is C or N;

E, F, G are each independently selected from CH or N, provided that at least one of B, E, F or G is N;

$R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy, or two $R_4$ attached at the same carbon atom form an oxo group;

$R_7$ is selected from cyano, halo$C_1$-$C_3$alkyl;

$R_8$ is selected from hydrogen, $NR_9R_{10}$, $C_1$-$C_3$alkoxy;

$R_9$ is hydrogen;

$R_{10}$ is selected from $C_1$-$C_3$alkyl, hydroxy$C_1$-$C_4$alkyl, $C_1$-$C_3$alkoxy$C_1$-$C_3$alkyl.

Various enumerated embodiments of the invention are described herein. It will be recognized that features specified in each embodiment may be combined with other specified features to provide further embodiments of the present invention.

Embodiment 1

A compound of formula (I) in free form or in pharmaceutically acceptable salt form

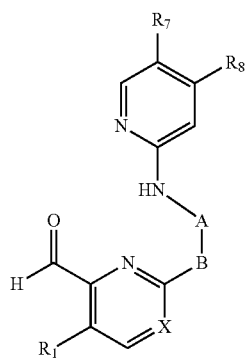

(I)

wherein
X is N or CH;
A is C(O) and B is $NR_5$ or
A and B together form part of a 5- or 6-membered aromatic ring wherein A is C and B is C or N;

$R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted once or more than once with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy or two $R_4$ attached at the same carbon atom form an oxo group;

$R_5$ is selected from hydrogen, $C_1$-$C_3$alkyl, $C_1$-$C_3$alkoxy$C_1$-$C_3$alkyl, $(CH_2)_{0-1}$—$R_6$;

$R_6$ is a 4-, 5-, or 6-membered saturated heterocyclic ring comprising at least one heteroatom selected from N, O, or S;

$R_7$ is selected from cyano, halo$C_1$-$C_3$alkyl;

$R_8$ is selected from hydrogen, $NR_9R_{10}$, $C_1$-$C_6$alkoxy;

$R_9$ is hydrogen;

$R_{10}$ is selected from $C_1$-$C_6$alkyl, hydroxy$C_1$-$C_6$alkyl, $C_1$-$C_4$alkoxy$C_1$-$C_6$alkyl.

Embodiment 2

A compound according to embodiment 1 of formula (Ia), in free form or in a pharmaceutically acceptable salt form,

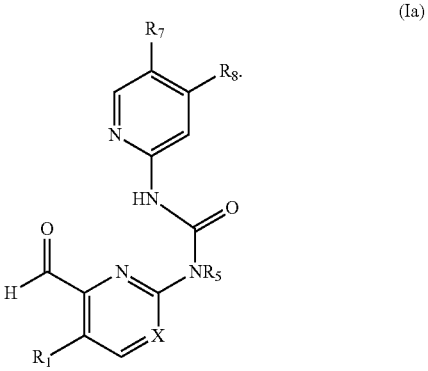

(Ia)

Embodiment 3

A compound according to embodiment 2 in free form or in pharmaceutically acceptable salt from, wherein $R_5$ is selected from $C_1$-$C_3$alkyl, $(CH_2)_{0-1}$—$R_6$.

Embodiment 4

A compound according to embodiment 1 of formula (Ib) in free form or in pharmaceutically acceptable salt form

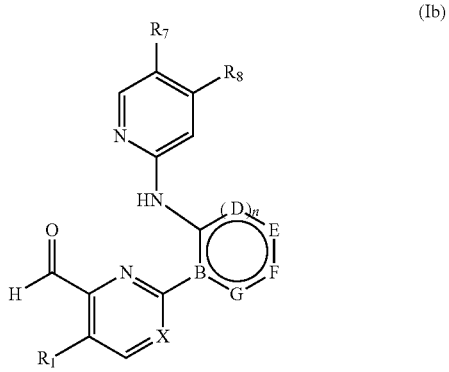

(Ib)

wherein n is 0 or 1;
B is C or N;
D, E, F, G are each independently selected from CH or N, provided that when n is 0, at least one of B, E, F or G is N.

Embodiment 5

A compound according to embodiment 4 in free form or in a pharmaceutically acceptable salt form, wherein n is 1, B is C and D, E, F, G are all CH.

Embodiment 6

A compound according to embodiment 4 in free form or in pharmaceutically acceptable salt form, wherein n is 0 and

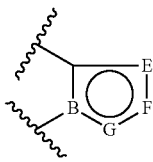

represents an imidazole or pyrazole ring.

Embodiment 7

A compound according to any of embodiments 1 to 6 in free form or in pharmaceutically acceptable salt form, wherein X is CH.

Embodiment 8

A compound according to any of embodiments 1 to 7 in free form or in pharmaceutically acceptable salt form, wherein $R_1$ is a 5-membered aromatic heterocyclic ring comprising at least one heteroatom selected from N, O or S, which ring is optionally substituted once or more than once with $C_1$-$C_3$alkyl.

Embodiment 9

A compound according to any of embodiments 1 to 7 in free form or in pharmaceutically acceptable salt form, wherein $R_1$ is $CH_2NR_2R_3$.

Embodiment 10

A compound according to embodiment 9, in free form or in pharmaceutically acceptable salt form, wherein $R_2$ and $R_3$ together with the N atom to which they are attached form a saturated 5- or 6-membered ring optionally comprising one additional heteroatom selected from N, O or S, which ring is optionally substituted once or more than once with $R_4$.

Embodiment 11

A compound according to embodiment 10, or a pharmaceutically acceptable salt thereof, wherein $R^2$ and $R^3$ together with the N atom to which they are attached form a pyrrolidine or piperazine ring, which ring is optionally substituted once or more than once with $R_4$.

Embodiment 12

A compound according to embodiments 10 or 11, or a pharmaceutically acceptable salt thereof, wherein $R_4$ is for each occurrence independently selected from $C_1$-$C_3$alkyl, or two $R_4$ attached at the same carbon atom form an oxo group.

Embodiment 13

A compound according to any of embodiments 10 to 12, or a pharmaceutically acceptable salt thereof, wherein, if $R_4$ is present, it is present one, two or three times.

Embodiment 14

A compound according to any of embodiments 1 to 13, wherein $R_7$ is cyano.

Embodiment 15

A compound according to any of embodiments 1 to 14, wherein $R_8$ is $NR_9R_{10}$.

Embodiment 16

A compound according to embodiment 15, wherein $R_9$ is hydrogen and $R_{10}$ is $C_1$-$C_3$alkoxy$C_1$-$C_3$alkyl.

Embodiment 17

A compound according to embodiment 1, which is selected from
6-((2-(6-formylpyridin-2-yl)phenyl)amino) nicotinonitrile;
3-(5-cyano-4-((2-methoxyethyl)amino)pyridin-2-yl)-1-(6-formylpyridin-2-yl)-1-methylurea;
3-(5-cyano-4-((2-methoxyethyl)amino)pyridin-2-yl)-1-(6-formylpyridin-2-yl)-1-(2-methoxyethyl)urea;
3-(5-cyano-4-((2-methoxyethyl)amino)pyridin-2-yl)-1-(6-formylpyridin-2-yl)-1-((tetrahydrofuran-3-yl)methyl)urea;
3-(5-cyano-4-((2-methoxyethyl)amino)pyridin-2-yl)-1-(6-formyl-5-(hydroxymethyl)pyridin-2-yl)-1-((tetrahydrofuran-3-yl)methyl)urea;
3-(5-cyano-4-isopropoxypyridin-2-yl)-1-(7-hydroxy-5-oxo-5,7-dihydrofuro[3,4-b]pyridin-2-yl)-1-methylurea;
3-(5-cyano-4-((2-methoxyethyl)amino)pyridin-2-yl)-1-(7-hydroxy-5-oxo-5,7-dihydrofuro[3,4-b]pyridin-2-yl)-1-methylurea;
3-(5-cyano-4-((2-methoxyethyl)amino)pyridin-2-yl)-1-ethyl-1-(6-formyl-5-(1-methyl-1H-pyrazol-4-yl)pyridin-2-yl)urea;
3-(5-cyano-4-(isopropylamino)pyridin-2-yl)-1-ethyl-1-(6-formyl-5-(1-methyl-1H-pyrazol-4-yl)pyridin-2-yl)urea;
3-(5-cyano-4-isopropoxypyridin-2-yl)-1-ethyl-1-(6-formyl-5-(1-methyl-1H-pyrazol-4-yl)pyridin-2-yl)urea;
3-(5-cyano-4-((2-methoxyethyl)amino)pyridin-2-yl)-1-(6-formyl-5-(1-methyl-1H-pyrazol-4-yl)pyridin-2-yl)-1-methylurea;
3-(5-cyano-4-(isopropylamino)pyridin-2-yl)-1-(6-formyl-5-(1-methyl-1H-pyrazol-4-yl)pyridin-2-yl)-1-methylurea;
N-((6-(3-(5-cyano-4-((2-methoxyethyl)amino)pyridin-2-yl)-1-methylureido)-2-formylpyridin-3-yl)methyl)-N-methylacetamide;
3-(5-cyano-4-((2-methoxyethyl)amino)pyridin-2-yl)-1-(5-(difluoromethyl)-6-formylpyridin-2-yl)-1-methylurea;
3-(5-cyano-4-isopropoxypyridin-2-yl)-1-(6-formyl-5-((4-methylpiperazin-1-yl)methyl)pyridin-2-yl)-1-methylurea;
3-(5-cyano-4-isopropoxypyridin-2-yl)-1-(5-(difluoromethyl)-6-formylpyridin-2-yl)-1-methylurea;
3-(5-cyanopyridin-2-yl)-1-(6-formyl-5-((2-oxopyrrolidin-1-yl)methyl)pyridin-2-yl)-1-methylurea 3-(5-cyanopyridin-2-yl)-1-(6-formyl-5-((2-oxopyrrolidin-1-yl)methyl)pyridin-2-yl)-1-methylurea;

3-(5-cyano-4-((2-methoxyethyl)amino)pyridin-2-yl)-1-(6-formyl-5-((2-oxopyrrolidin-1-yl)methyl)pyridin-2-yl)-1-methylurea;
3-(5-cyano-4-isopropoxypyridin-2-yl)-1-(6-formyl-5-((4-methyl-2-oxopiperazin-1-yl)methyl)pyridin-2-yl)-1-methylurea;
3-(5-cyano-4-((2-hydroxy-2-methylpropyl)amino)pyridin-2-yl)-1-(6-formyl-5-(1-methyl-1H-pyrazol-4-yl)pyridin-2-yl)-1-methylurea;
3-(5-cyano-4-isopropoxypyridin-2-yl)-1-(6-formyl-5-((2-oxopyrrolidin-1-yl)methyl)pyridin-2-yl)-1-methylurea;
3-(5-cyano-4-((2-methoxyethyl)amino)pyridin-2-yl)-1-(6-formyl-5-((4-methyl-2-oxopiperazin-1-yl)methyl)pyridin-2-yl)-1-methylurea;
3-(5-cyano-4-isopropoxypyridin-2-yl)-1-(6-formyl-5-(1-methyl-1H-pyrazol-4-yl)pyridin-2-yl)-1-methylurea;
3-(5-cyano-4-isopropoxypyridin-2-yl)-1-(6-formyl-5-((3-methoxypyrrolidin-1-yl)methyl)pyridin-2-yl)-1-methylurea;
6-(2-((4-((2-methoxyethyl)amino)-5-(trifluoromethyl)pyridin-2-yl)amino)-1H-imidazol-1-yl)-3-(1-methyl-1H-pyrazol-4-yl)picolinaldehyde;
6-(5-((4-((2-methoxyethyl)amino)-5-(trifluoromethyl)pyridin-2-yl)amino)-1H-pyrazol-1-yl)-3-(1-methyl-1H-pyrazol-4-yl)picolinaldehyde;
3-(5-cyano-4-isopropoxypyridin-2-yl)-1-(6-formyl-5-(pyrrolidin-1-ylmethyl)pyridin-2-yl)-1-methylurea and
1-(5-cyano-4-isopropoxypyridin-2-yl)-3-(4-formylpyrimidin-2-yl)urea.

Embodiment 18

A compound according to embodiment 17, which is selected from
(R)-3-(5-cyano-4-((2-methoxyethyl)amino)pyridin-2-yl)-1-(6-formylpyridin-2-yl)-1-(((tetrahydrofuran-3-yl)methyl)urea and
(S)-3-(5-cyano-4-((2-methoxyethyl)amino)pyridin-2-yl)-1-(6-formylpyridin-2-yl)-1-(((tetrahydrofuran-3-yl)methyl)urea.

Embodiment 19

A pharmaceutical composition comprising a compound or pharmaceutically acceptable salt thereof according to any of embodiments 1 to 18.

Embodiment 20

A combination comprising a therapeutically effective amount of a compound or a pharmaceutically acceptable salt thereof according to any of embodiments 1 to 18 and one or more therapeutically active agent.

Embodiment 21

A combination according to embodiment 20, wherein the one or more therapeutically active agent is selected from an anti-cancer agent.

Embodiment 22

A compound or a pharmaceutically acceptable salt thereof according to any of embodiments 1 to 18 for use as a medicament.

Embodiment 23

A compound or a pharmaceutically acceptable salt thereof according to any of embodiments 1 to 18 for use in inhibiting FGFR4 activity in a subject.

Embodiment 24

A compound or a pharmaceutically acceptable salt thereof according to any of embodiments 1 to 18 for use in treating a disorder or disease which is treated by inhibition of FGFR4 in a subject.

Embodiment 25

A compound or a pharmaceutically acceptable salt thereof according to any of embodiments 1 to 18 for use in treating a disorder or disease selected from cancer.

Embodiment 26

A compound or a pharmaceutically acceptable salt thereof for use according to embodiment 25 wherein the cancer is selected from liver cancer, breast cancer, glioblastoma, prostate cancer, rhabdomyosarcoma, gastric cancer, ovarian cancer, lung cancer, colon cancer.

Embodiment 27

A compound or a pharmaceutically acceptable salt thereof for use according to embodiment 26, wherein the cancer is liver cancer.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula (I), (Ia) or (Ib) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of formula (I), (Ia) or (Ib) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I). For instance, the invention provides a co-crystal comprising a compound of formula (I) and an organic acid, such as, e.g. citric acid.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by FGFR4, or (ii) associated with FGFR4 activity, or (iii) characterized by activity (normal or abnormal) of FGFR4, or (2) reduce or inhibit the activity of FGFR4; or (3) reduce or inhibit the expression of FGFR4. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of FGFR4.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration.

In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent. Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Examples of solvate of the compounds of the invention are depicted below (compounds (I-a) and (I-3a)).

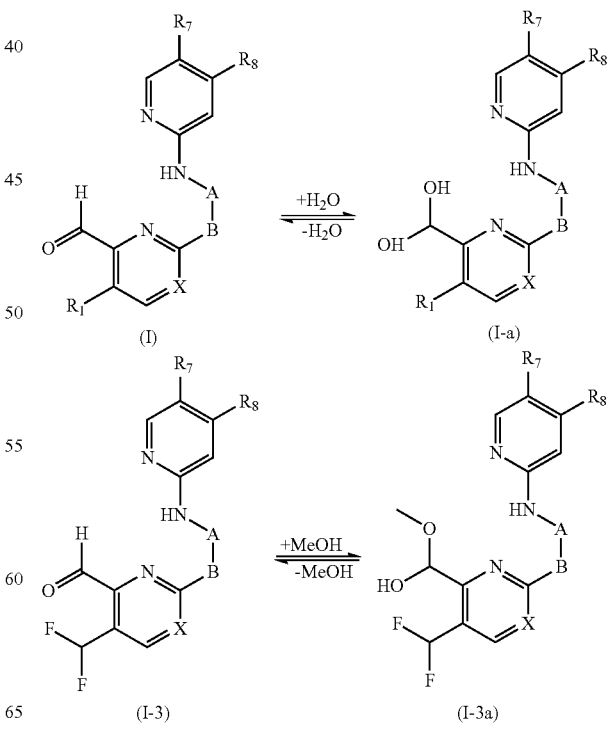

Thus, the compounds of the invention and their solvates, such as compounds of formula (I) and (I-3) and their respective solvates (I-a) and (I-3a) wherein A, B, X, $R_7$ and $R_8$ are as defined herein in relation to a compound of formula (I), also form part of the invention.

The presence of solvates can be identified by a person of skill in the art with tools such as NMR.

The compounds of the present invention, including salts, hydrates and solvates thereof, may inherently or by design form polymorphs.

Typically, the compounds of formula (I), in particular compounds of formula (Ia) and (Ib) can be prepared according to the Schemes provided infra.

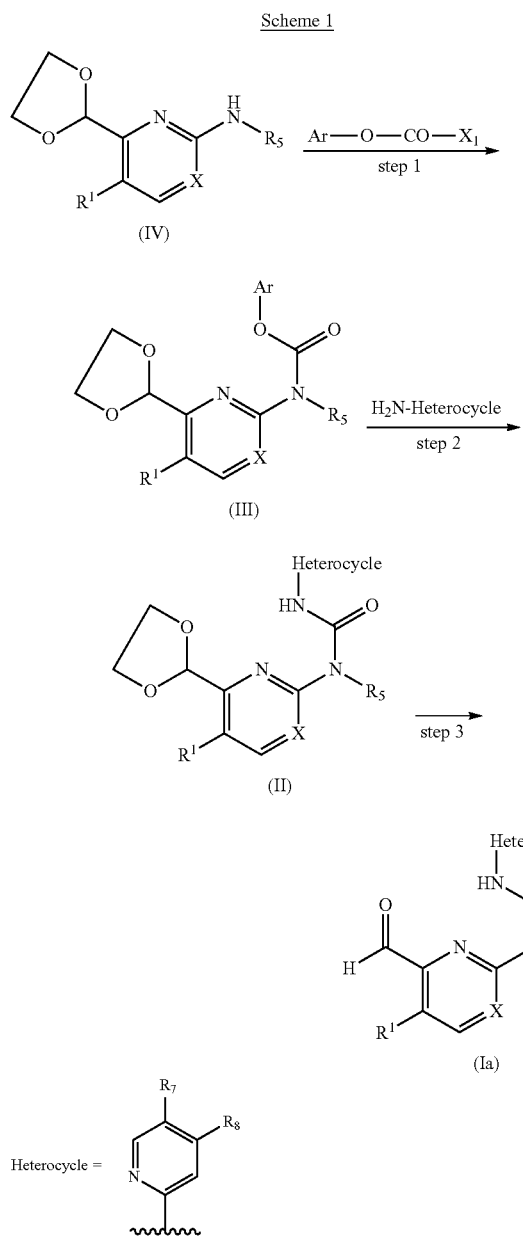

Step 1: a compound of formula (IV) wherein $R_1$, X and $R_5$ are as defined herein in relation to a compound of formula (I), e.g. an aminopyridine or related analogues, is activated with an acylating agent (Ar—O—CO—$X_1$, wherein $X_1$ is a leaving group and Ar is an aryl group including for example phenyl, para-nitrophenyl, 4-fluorophenyl, pentafluorophenyl), such as phenyl chloroformate or diphenyl carbonate to give an aryl carbamate compound of formula (III). The acylation of the compound of formula (IV) to prepare the aryl carbamate compound of formula (III) may occur with or without activation. An example of suitable activation is deprotonation with a base such a lithium hexamethyldisilazide.

Step 2: $NH_2$—Heterocycle, wherein $R_7$ and $R_8$ are as defined herein in relation to a compound of formula (I), displaces the OAr moiety of the arylcarbamate compound of formula (III) wherein $R_1$, X and $R_5$ are as defined herein in relation to a compound of formula (I), either directly or with activation, to give a compound of formula (II) wherein $R_1$, $R_5$, $R_7$, $R_8$, and X are as defined herein in relation to a compound of formula (I). An example of suitable activation is deprotonation with a base such a lithium hexamethyldisilazide.

Step 3: The acetal protecting group of compound of formula (II) wherein $R_1$, $R_5$, $R_7$, $R_8$, and X are as defined herein in relation to a compound of formula (I) is removed by treatment with aqueous acid to give a compound of formula (Ia) wherein $R_1$, $R_5$, $R_7$, $R_8$, and X are as defined herein in relation to a compound of formula (I). Trapping of the liberated aldehyde as the corresponding aldehyde bisulphite adduct can be used as a means to facilitate purification. The pure bisulphite adduct can then be isolated, an example being by filtration, before liberating the aldehyde in a pure form. An example of suitable conditions for bisulphite adduct formation is treatment with $NaHSO_3$ in water. An example of suitable conditions for bisulphite adduct deprotection back to the aldehyde is treatment with aqueous $NaHCO_3$ solution.

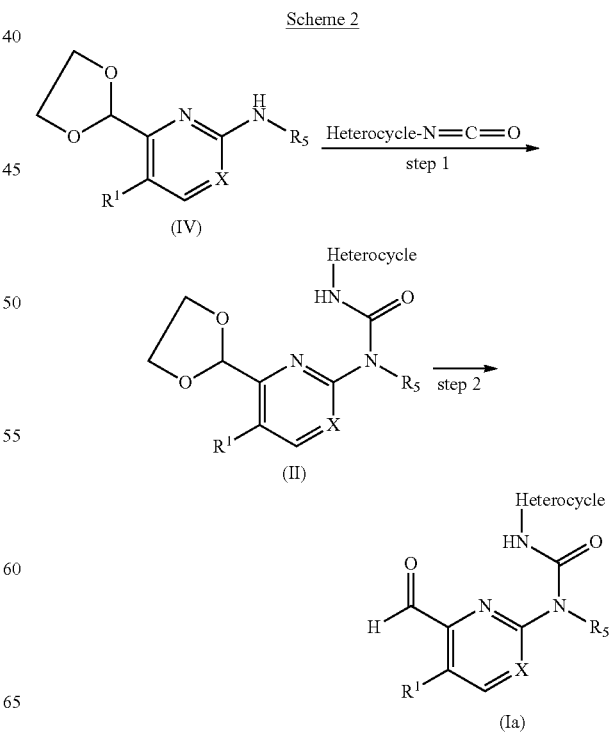

Heterocycle = 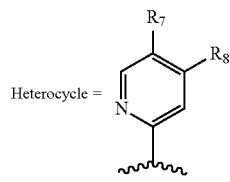

Step 1: The compound of formula (IV) wherein $R_1$, $R_5$ and X are as defined herein in relation to a compound of formula (I), e.g. an aminopyridine or related analogues, is reacted with an isocyanate compound (Heterocycle-N=C=O) wherein $R_7$ and $R_8$ are as defined herein in relation to a compound of formula (I), or an isocyanate equivalent that can liberate the isocyanate in situ, to give a compound of formula (II) wherein $R_1$, $R_5$, $R_7$, $R_8$ and X are as defined herein in relation to a compound of formula (I). Examples of suitable isocyanate precursors used to prepare Heterocycle-N=C=O include phenyl carbamates, acyl imidazoles, acyl triazoles and carbamoyl chlorides.

Step 2: The acetal protecting group of compound of formula (II) wherein $R_1$, $R_5$, $R_7$, $R_8$ and X are as defined herein in relation to a compound of formula (I) is removed by treatment with aqueous acid to give a compound of formula (Ia) wherein $R_1$, $R_5$, $R_7$, $R_8$, and X are as defined herein in relation to a compound of formula (I).

Step 1: A compound of formula (VI) wherein $R_1$, $R_5$ and X are as defined herein in relation to a compound of formula (I), e.g. a bromoaminopyridine or related analogues, is reacted with an isocyanate compound (Heterocycle-N=C=O) wherein $R_7$ and $R_8$ are as defined herein in relation to a compound of formula (I), or an isocyanate equivalent that can liberate the isocyanate in situ, to give a compound of formula (V) wherein $R_1$, $R_5$, $R_7$, $R_8$ and X are as defined herein in relation to a compound of formula (I). Examples of suitable isocyanate precursors used to prepare Heterocycle-N=C=O include phenyl carbamates, acyl imidazoles, acyl triazoles and carbamoyl chlorides.

Step 2: A compound of formula (V) wherein $R_1$, $R_5$, $R_7$, $R_8$ and X are as defined herein in relation to a compound of formula (I) undergoes a halogen-metal exchange reaction to generate a 2-pyridyl organometallic intermediate. Examples of suitable reagents to conduct this halogen-metal exchange include n-butyl lithium and tert-butyllithium. The intermediate 2-pyridyl organometallic species is then formylated with a suitable formylating reagent, such as DMF, to introduce the 2-formyl group and give a compound of formula (Ia) wherein $R_1$, $R_5$, $R_7$, $R_8$, and X are as defined herein in relation to a compound of formula (I).

Scheme 3

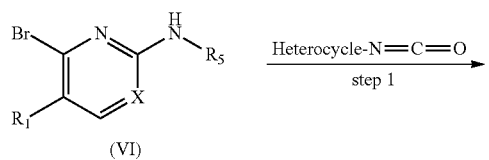

(VI)

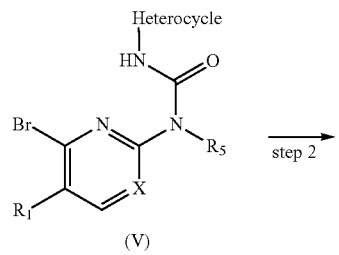

(V)

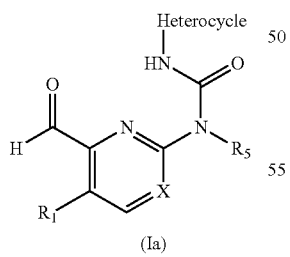

(Ia)

Heterocycle = 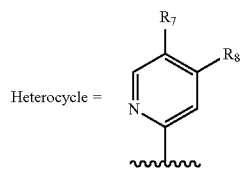

Scheme 4

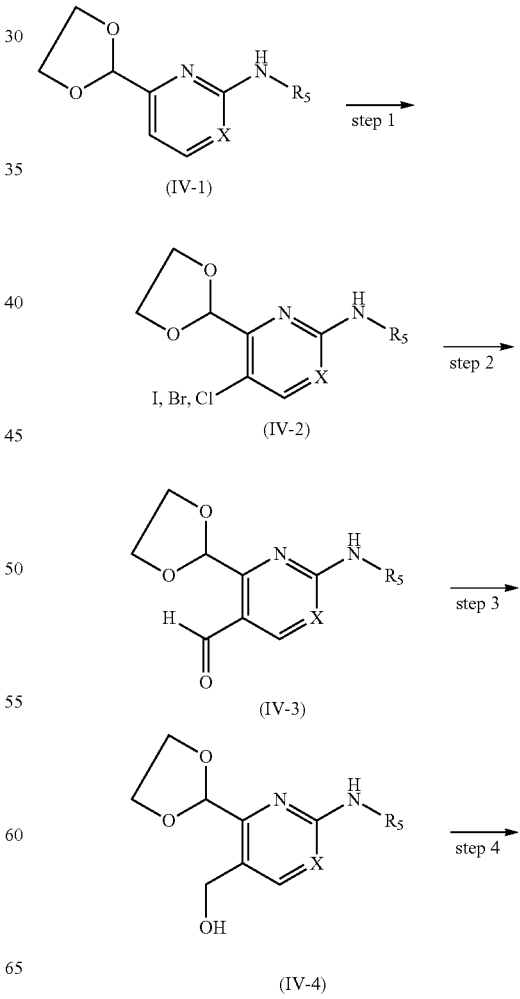

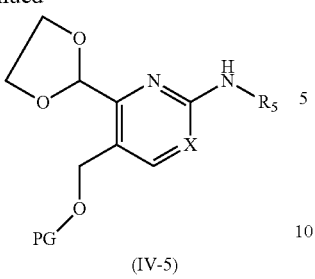

(IV-5)

An approach to introducing $R_1$ substituents, ortho to the 2-formyl group, in compounds of formula (I), is outlined in scheme 4.

Step 1: Bromination, iodination or chlorination of a compound of formula (IV-1) wherein $R_5$ and X are as defined herein in relation to a compound of formula (I) occurs following treatment with a suitable brominating, iodinating or chlorinating agents respectively such as N-bromosuccinimide, N-iodosuccinimide or N-chlorosuccinimide, to give a compound of formula (IV-2) wherein $R^5$ and X are as defined herein in relation to a compound of formula (I).

Step 2: A compound of formula (IV-3) wherein $R_5$ and X are as defined herein in relation to a compound of formula (I) is obtained by a halogen-metal exchange reaction of a compound of formula (IV-2) wherein $R_5$ and X are as defined herein in relation to a compound of formula (I), followed by formylation of the metalated intermediate. Suitable reagent combinations include n-butyl lithium and DMF. A compound of formula (IV-3) wherein $R_5$ and X are as defined herein in relation to a compound of formula (I) can be used as starting material in schemes 1 and 2 shown above.

Steps 3 and 4: Compound of formula (IV-3) wherein $R_5$ and X are as defined herein in relation to a compound of formula (I) can be further elaborated, one example being reduction to and protection of the primary alcohol with an appropriate protecting group (PG), as outlined in steps 3 and 4 respectively. Suitable reagents for the reduction step include $NaBH_4$ and $B_2H_6$, and a suitable protecting group would be a trialkylsilyl group such as tertbutyldimethylsilyl. The protected intermediates (e.g. compound of formula (IV-5) wherein $R_5$ and X are as defined herein in relation to a compound of formula (I)) can then be coupled to give a compound of formula (Ia) wherein $R_1$, $R_5$, $R_7$, $R_8$, and X are as defined herein in relation to a compound of formula (I), as described in schemes 1 and 2.

Scheme 5

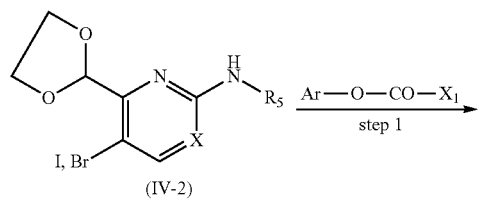

(IV-2)

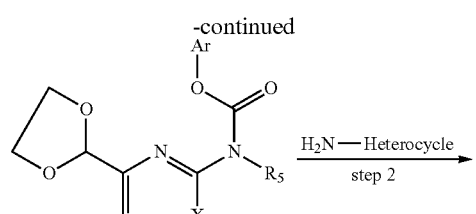

(III-1)

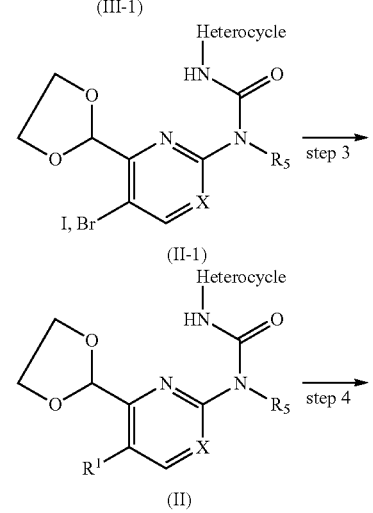

(II-1)

(II)

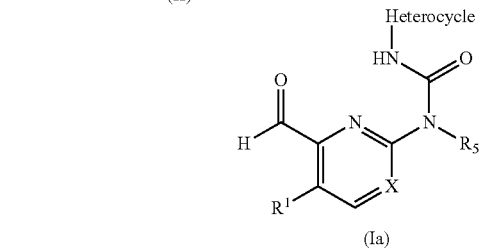

(Ia)

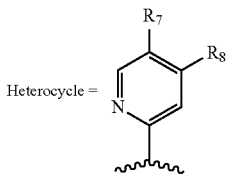

Heterocycle =

Steps 1 and 2: The compound of formula (IV-2) wherein $R_5$ and X are as defined herein in relation to a compound of formula (I)), can be converted to the corresponding urea derivatives (compounds of formula (II-1) wherein $R_5$, $R_7$, $R_8$ and X are as defined herein in relation to a compound of formula (I)), following the methodology outlined in scheme 1.

Step 3: A compound of formula (II), wherein $R_1$, $R_5$, $R_7$, $R_8$ and X are as defined in a compound of formula (I) may be obtained following a number of approaches which include for example trifluoromethylation, or arylation. Suitable trifluoromethylating reagents include: (1,10-phenanthroline)(trifluoromethyl)copper(I). Suitable arylation conditions would include via Suzuki or Stille coupling reactions.

Step 4: The compounds of formula (II), wherein $R_1$, $R_5$, $R_7$, $R_8$ and X are as defined in a compound of formula (I) can then be deprotected to give compounds of formula (Ia) wherein $R_1$, $R_5$, $R_7$, $R_8$, and X are as defined herein in relation to a compound of formula (I), as described in schemes 1 and 2.

Scheme 6

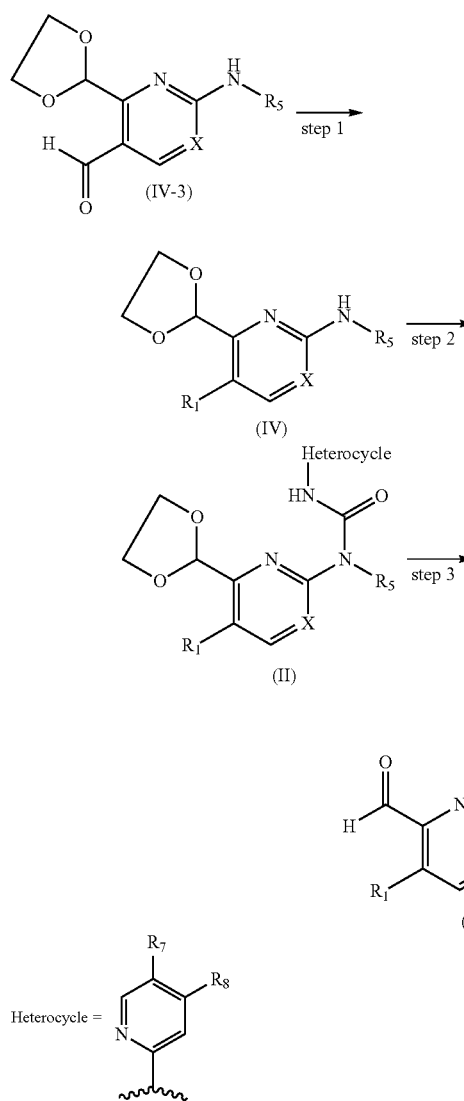

a compound of formula (Ia) wherein $R_1$, $R_5$, $R_7$, $R_8$, and X are as defined herein in relation to a compound of formula (I), as described in schemes 1 and 2.

The acetal group depicted in compounds of Schemes 1, 2, 4, 5 and 6 may be replaced by other suitable acetal such as dialkyl acetals, eg dimethoxy.

Scheme 7

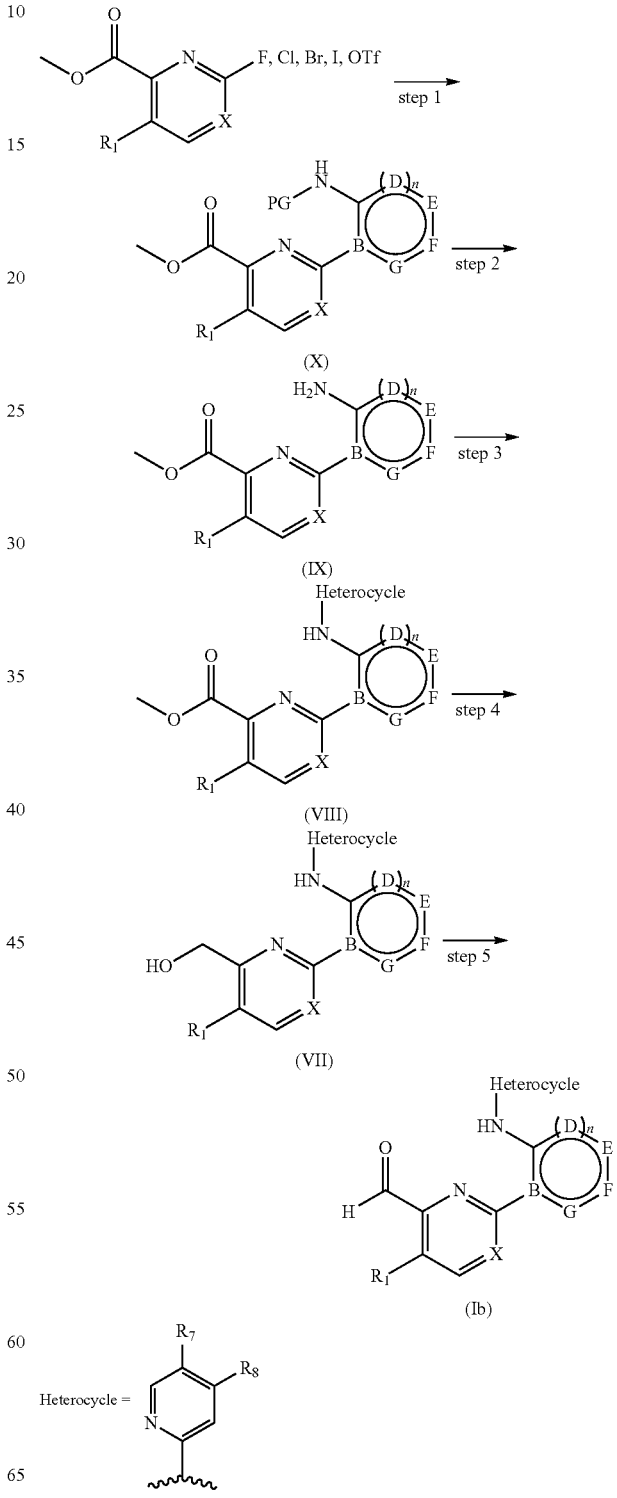

Step 1: Compounds of formula (IV-3) wherein $R_5$ and X are as defined herein in relation to a compound of formula (I), outlined in scheme 4, can be converted to compounds of formula (IV) wherein $R_1$, $R_5$ and X are as described herein in relation to a compound of formula (I) following a number of approaches which include, for example: fluorination with deoxygenation to generate $R_1$=difluoromethyl; reductive amination to generate $R_1$=aminomethyl where the amino group can be primary secondary or tertiary. In the case of $R_1$ being a secondary aminomethyl group, a further acylation reaction can be conducted to generate a tertiary amide, or via an intramolecular reaction a lactam derivative. Suitable reagent combinations for the fluorination reaction include: DAST or XtalFluor with triethylamine trihydrofluoride. Suitable reagent combinations for the reductive amination include: Na(OAc)$_3$BH with the corresponding amines, or amino esters. Suitable acylating reagents include: acetic anhydride, or intramolecular aminolysis of an ester.

Steps 2 and 3: Compounds of formula (IV) wherein $R_1$, $R_5$ and X are as defined herein in relation to a compound of formula (I) undergo urea formation and deprotection to give Step 1: A compound of formula (XI) wherein $R_1$ and X are as defined herein in relation to a compound of formula (I), e.g. a 2-halopyridine or related analogues, is coupled with a suitable organometallic aromatic compound containing an ortho-amino group, or a suitably protected ortho-amino group, or being amenable to the introduction of an ortho-amino group, in a reaction such as a Suzuki reaction, with an aryl boronic acid, or with an arylboronic acid ester, to give a biaryl compound of formula (X), wherein $R_1$, X, n, B, D, E, F and G are as defined herein in relation to a compound of formula (I) and wherein PG is a protecting group. Suitable conditions include heating with a catalyst, such as $PdCl_2(PPh_3)_2$, and a base, such as $NaHCO_3$, in a solvent mixture of water and an organic solvent, such as 1,2-dimethoxyethane. Other cross-coupling reactions, such as Stille or Negishi couplings can also be applied to form the compound of formula (X). Examples of suitable amino protecting groups (PG) for the ortho-amino group include: di-tertbutyl-dicarbonate (Boc), acetyl, carboxybenzyl (Cbz).

Step 2: A compound of formula (IX) wherein $R_1$, X, n, B, D, E, F and G are as defined herein in relation to a compound of formula (I) can be obtained by deprotection of a compound of formula (X) wherein $R_1$, X, n, B, D, E, F and G are as defined herein in relation to a compound of formula (I) and wherein PG is a protecting group. For example, treatment of a compound of formula (X) wherein PG is Boc with an acid, such as trifluoroacetic acid, yields a compound of formula (IX).

Step 3: A compound of formula (VIII) wherein $R_1$, $R_7$, $R_8$, X, n, B, D, E, F and G are as defined herein in relation to a compound of formula (I) is obtained by reaction of a compound of formula (IX) wherein $R_1$, X, n, B, D, E, F and G are as defined herein in relation to a compound of formula (I) with a 2-halo or 2-trifluoromethane sulphonylpyridine, wherein the pyridine moiety is the heterocycle depicted in scheme 7 wherein $R_7$ and $R_8$ are as defined herein in relation to a compound of formula (I), in a transition-metal catalysed coupling reaction, such as a Buckwald-Hartwig, or Goldberg coupling reaction. Suitable conditions include heating with a catalyst, such as $Pd_2(dba)_3$, a ligand, such as 4,5-bis(diphenylphosphino)-9,9-dimethylxanthene, and a base, such as $Cs_2CO_3$, in a solvent, such as 1,4-dioxane.

Step 4: A compound of formula (VII) wherein $R_1$, $R_7$, $R_8$, X, n, B, D, E, F and G are as defined herein in relation to a compound of formula (I) is obtained by reaction of a compound of formula (VIII) wherein $R_1$, X, n, B, D, E, F and G are as defined herein in relation to a compound of formula (I) by reduction using a suitable reducing agent, such as $LiBH_4$.

Step 5: A compound of formula (Ib) wherein $R_1$, $R_7$, $R_8$, X, n, B, D, E, F and G are as defined herein in relation to a compound of formula (I) is obtained by reaction of a compound of formula (VII) wherein $R_1$, $R_7$, $R_8$, X, n, B, D, E, F and G are as defined herein in relation to a compound of formula (I) with a suitable oxidising agent such as manganese dioxide.

Scheme 8

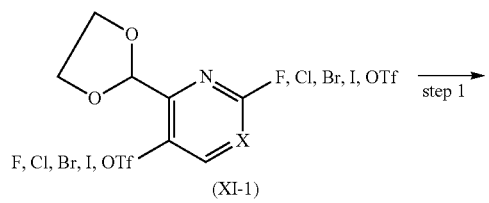

(XI-1)

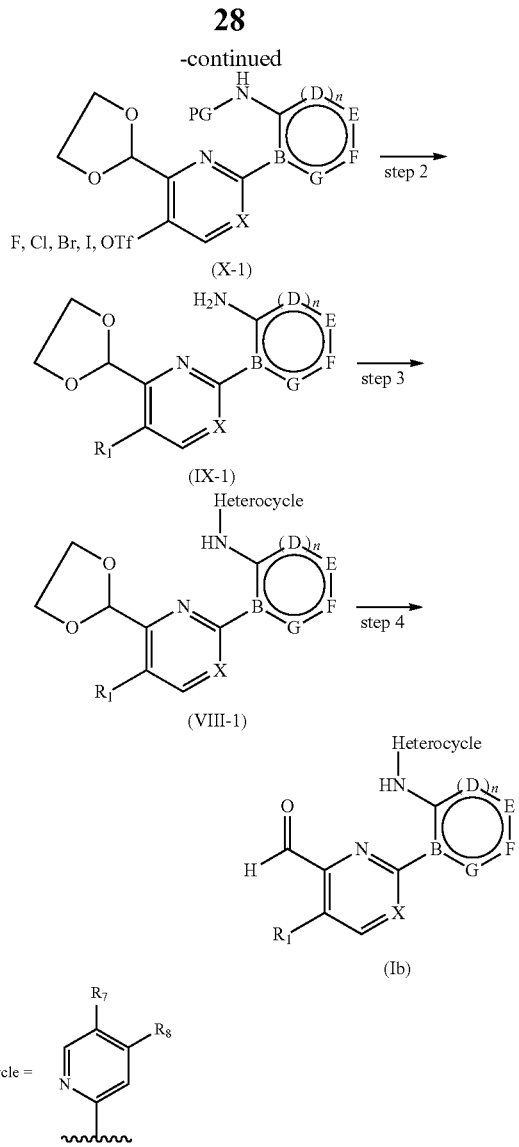

Step 1: A compound of formula (XI-1), wherein X is as defined herein in relation to a compound of formula (I), e.g. a 3,6-dihalopyridine or related analogues, is coupled with a suitable aromatic compound containing an ortho-amino group, or being amenable to the introduction of an ortho-amino group for example a 2-amino imidazole, or a 5-amino pyrazole, in a reaction such as a Goldgerg reaction, to give a biaryl compound of formula (X-1) wherein X, n, B, D, E, F and G are as defined herein in relation to a compound of formula (I) and PG is a protecting group. Suitable conditions include heating with a catalyst, such as copper (I) iodide, with a ligand, such as 8-hydroxyquinoline, and a base, such as $Cs_2CO_3$, in a solvent, such as tert-butanol.

Step 2: A compound of formula (IX-1) wherein $R_1$, X, n, B, D, E, F and G are as defined herein in relation to a compound of formula (I), is obtained by the reaction of (X-1) wherein X, n, B, D, E, F and G are as defined herein in relation to a compound of formula (I) with a boronic acid, or with a boronic acid ester derivative, in a Suzuki reaction. Other cross-coupling reactions, such as Stille or Negishi couplings can also be applied to form the compound of formula (IX-1). Suitable conditions include heating with a catalyst, such as $PdCl_2(dppf)$, and a base, such as $Na_2CO_3$, in a solvent mixture of water and an organic solvent, such as 1,2-dimethoxyethane.

Step 3: A compound of formula (VIII-1) wherein $R_1$, $R_7$, $R_8$, X, n, B, D, E, F and G are as defined herein in relation to a compound of formula (I), is obtain by reacting a compound of formula (IX-1) wherein $R_1$, X, n, B, D, E, F and G are as defined herein in relation to a compound of formula (I) with a 2-halo or 2-trifluoromethane sulphonylpyridine, wherein the pyridine moiety is the heterocycle depicted in scheme 8 wherein $R_7$ and $R_8$ are as defined herein in relation to a compound of formula (I), in a transition-metal catalysed coupling reaction, such as a Buckwald-Hartwig, or Goldberg coupling reaction. Suitable conditions include heating with a catalyst, such as $Pd_2(dba)_3$, a ligand, such as Xantphos, and a base, such as $Cs_2CO_3$, in a solvent, such as 1,4-dioxane.

Step 4: A compound of formula (VIII-1) wherein $R_1$, $R_7$, $R_8$, X, n, B, D, E, F and G are as defined herein in relation to a compound of formula (I), undergoes deprotection of its acetal group by treatment with aqueous acid to give a compound of formula (Ib) wherein $R_1$, $R_7$, $R_8$, X, n, B, D, E, F and G are as defined herein in relation to a compound of formula (I).

In a further aspect, the invention relates to a process for the preparation of a compound of formula (I), in particular a compound of formula (Ia), in free form or in pharmaceutically acceptable salt form, comprising the steps of:

a) coupling a compound of formula (IV) as defined herein with a suitable isocyanate compound to give a compound of formula (II) as defined herein;

b) deprotecting the compound of formula (II) as defined herein obtained in step a) to give a compound of formula (I);

c) recovering the so obtainable compound of formula (I) in free form or in pharmaceutically acceptable salt form.

In a further aspect, the invention relates to a process for the preparation of a compound of formula (I), in particular a compound of formula (Ib) in free form or in pharmaceutically acceptable salt form, comprising the steps of:

a) coupling a compound of formula (XI) as defined herein with a suitable amino aryl compound to give a compound of formula (IX) as defined herein;

b) coupling a compound of formula (IX) as defined herein with a suitable pyridyl compound to give a compound of formula (VIII) as defined herein;

c) converting a compound of formula (VIII) to a compound of formula (I);

d) recovering the so obtainable compound of formula (I) in free form or in pharmaceutically acceptable salt form.

Compounds of formula (II), (III), (IV), (V), (VI), (VII), (VIII), (IX), (X), (XI) as defined herein are useful in the preparation of compounds of the invention, e.g., compounds of Formula (I). Thus, in an aspect, the invention relates to a compound of formula (II), (III), (IV), (V), (VI), (VII), (VIII), (IX), (X), (XI) or salts thereof. In another aspect, the invention relates to the use of a compound of formula (II), (III), (IV), (V), (VI), (VII), (VIII), (IX), (X), (XI) or salts thereof in the manufacture of a compound of formula (I).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol;

c) binders, e.g., magnesium aluminum silicate, starch paste, gelatin, tragacanth, methylcellulose, sodium carboxymethylcellulose and/or polyvinylpyrrolidone;

d) disintegrants, e.g., starches, agar, alginic acid or its sodium salt, or effervescent mixtures; and e) absorbents, colorants, flavors and sweeteners.

In an embodiment, the pharmaceutical compositions are capsules comprising the active ingredient only.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula (I) in free form or in pharmaceutically acceptable salt form, exhibit valuable pharmacological properties, e.g. FGFR4 modulating properties, e.g. as indicated in the in vitro tests as provided in the examples, and are therefore indicated for therapy or for use as research chemicals, e.g. as tool compounds.

Particularly interesting compounds of the invention have good potency in the biological assays described herein. In another aspect, they should have a favourable safety profile. In another aspect, they should possess favourable pharmacokinetic properties. Furthermore, the ideal drug candidate will be in a form that is stable, non-hygroscopic and easily formulated. The compounds of the invention are selective for FGFR4 over other receptors, in particular over other FGF receptors such as FGFR1, FGFR2 and FGFR3. Thus, the present invention relates to compounds which are selective FGFR4 inhibitors.

Having regard to their activity as FGFR4 inhibitors, compounds of the formula (I) in free or pharmaceutically acceptable salt form, are useful in the treatment of conditions which are mediated by the activity of FGFR4 proteins, such as cancer, and/or that are responsive (meaning especially in a therapeutically beneficial way) to inhibition of FGFR4, most especially a disease or disorder as mentioned herein below.

Compounds of the invention may be useful in the treatment of cancer. In particular, the compounds of the invention may be useful in the treatment of an indication selected from liver cancer, breast cancer, glioblastoma, prostate cancer, rhabdomyosarcoma, gastric cancer, ovarian cancer, lung cancer, colon cancer.

The compounds of the invention may also be useful in the treatment of solid malignancies characterized by positive FGFR4 expression.

The compounds of the invention may also be useful in the treatment of solid malignancies characterized by positive KLB (beta-klotho) expression.

The compounds of the invention may also be useful in the treatment of solid malignancies characterized by positive FGF19 expression.

The compounds of the invention may also be useful in the treatment of solid malignancies characterized by positive FGFR4 and positive KLB expression. The compounds of the invention may also be useful in the treatment of solid malignancies characterized by positive FGFR4 and positive FGF19 expression.

The compounds of the invention may also be useful in the treatment of solid malignancies characterized by positive FGFR4, positive KLB and positive FGF19 expression.

Any positive expression in FGFR4, KLB and/or FGF19 as described above can be assessed by methods known to the skilled person such as e.g. RT-qPCR, Western blotting, ELISA, immunohistochemistry.

Solid malignancies characterized by positive FGFR4 and KLB expression include, for example, liver cancer.

Thus, as a further embodiment, the present invention provides the use of a compound of formula (I) or a pharmaceutically acceptable salt thereof, in therapy. In a further embodiment, the therapy is for a disease which may be treated by inhibition of FGFR4. In another embodiment, the disease is selected from the afore-mentioned list, suitably liver cancer.

Thus, as a further embodiment, the present invention provides a compound of formula (I) or a pharmaceutically acceptable salt thereof for use in therapy. In a further embodiment, the therapy is for a disease which may be treated by inhibition of FGFR4. In another embodiment, the disease is selected from the afore-mentioned list, suitably liver cancer.

In another embodiment, the invention provides a method of treating a disease which is treated by inhibition of FGFR4 comprising administration of a therapeutically acceptable amount of a compound of formula (I) or a pharmaceutically acceptable salt thereof. In a further embodiment, the disease is selected from the afore-mentioned list, suitably liver cancer.

In an embodiment, the invention provides a method of inhibiting FGFR4 activity in a subject, wherein the method comprises administering to the subject a therapeutically effective amount of the compound according to any one of claims 1 to 5 or a pharmaceutically acceptable salt thereof.

In an embodiment, the invention provides a method of treating cancer, comprising administering to the subject a therapeutically effective amount of the compound according to any one of claims 1 to 5 or a pharmaceutically acceptable salt thereof.

Thus, as a further embodiment, the present invention provides the use of a compound of formula (I) or a pharmaceutically acceptable salt thereof, for the manufacture of a medicament. In a further embodiment, the medicament is for treatment of a disease which may be treated by inhibition of FGFR4. In another embodiment, the disease is selected from the afore-mentioned list, suitably liver cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The activity of a compound according to the present invention can be assessed by the in vitro methods described in the Examples.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention. Thus, in one embodiment, the invention provides a combination comprising a therapeutically effective amount of a compound of formula (I) or a pharmaceutically acceptable salt thereof and one or more therapeutically active agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by FGFR4. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In certain instances, compounds of the present invention such as compounds of any of examples 1 to 30 may be combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention such as any of the compounds of examples 1 to 30 include:

Tyrosine kinase inhibitors such as Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®);

Vascular Endothelial Growth Factor (VEGF) receptor inhibitors such as Bevacizumab (Avastin®), axitinib (Inlyta®); Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy)propan-2-yl)$_2$-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TK1258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7);

(3R,4R)-4-Amino-1-((4-((3-methoxyphenyl)amino) pyrrolo[2,1-f][1,2,4]triazin-5-yl)methyl)piperidin-3-ol (BMS690514); N-(3,4-Dichloro-2-fluorophenyl)-6-methoxy-7-[[(3aα, 5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl] amino]-N-[3-(trifluoromethyl)phenyl]-benzamide (BHG712, CAS 940310-85-0); and Aflibercept (Eylea®);

Platelet-derived Growth Factor (PDGF) receptor inhibitors Imatinib (Gleevec®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Quizartinib (AC220, CAS 950769-58-1); Pazopanib (Votrient®); Axitinib (Inlyta®); Sorafenib (Nexavar®); Vargatef (BIBF1120, CAS 928326-83-4); Telatinib (BAY57-9352, CAS 332012-40-5); Vatalanib dihydrochloride (PTK787, CAS 212141-51-0); and Motesanib diphosphate (AMG706, CAS 857876-30-3, N-(2,3-dihydro-3,3-dimethyl-1H-indol-6-yl)-2-[(4-pyridinylmethyl) amino]-3-pyridinecarboxamide, described in PCT Publication No. WO 02/066470);

Fibroblast Growth Factor Receptor (FGFR) Inhibitors such as Brivanib alaninate (BMS-582664, (S)-((R)-1-(4-(4-Fluoro-2-methyl-1H-indol-5-yloxy)-5-methyl-pyrrolo[2,1-f][1,2,4]triazin-6-yloxy)propan-2-yl)$_2$-aminopropanoate); Vargatef (BIBF1120, CAS 928326-83-4); Dovitinib dilactic acid (TK1258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and N-[2-[[4-(Diethylamino)butyl]amino]-6-(3,5-dimethoxyphenyl)pyrido [2,3-d]pyrimidin-7-yl]-N'-(1,1-dimethylethyl)-urea (PD173074, CAS 219580-11-7);

Aurora kinase inhibitors such as Danusertib (PHA-739358); N-[4-[[6-Methoxy-7-[3-(4-morpholinyl) propoxy]-4-quinazolinyl]amino]phenyl]benzamide (ZM447439, CAS 331771-20-1); 4-(2-Amino-4-methyl-5-thiazolyl)-N-[4-(4-morpholinyl)phenyl]-2-pyrimidinamine (CYC116, CAS 693228-63-6); Tozasertib (VX680 or MK-0457, CAS 639089-54-6); Alisertib (MLN8237); (N-{2-[6-(4-Cyclobutylamino)-5-trifluoromethyl-pyrimidine-2-ylamino)-(1S,4R)-1,2,3,4-tetrahydro-1,4-epiazano-naphthalen-9-yl]-2-oxoethyl}-acetamide) (PF-03814735); 4-[[9-Chloro-7-(2, 6-difluorophenyl)-5H-pyrimido[5,4-d][2]benzazepin-2-yl]amino]-benzoic acid (MLN8054, CAS 869363-13-3); Cenisertib (R-763); Barasertib (AZD1152); and N-cyclopropyl-N'-[3-[6-(4-morpholinylmethyl)-1H-benzimidazol-2-yl]-1H-pyrazol-4-yl]-urea (AT9283);

Cyclin-Dependent Kinase (CDK) inhibitors such as Aloisine A; Alvocidib (also known as flavopiridol or HMR-1275, 2-(2-chlorophenyl)-5,7-dihydroxy-8-[(3S, 4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-Methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido [5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]-N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl)amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438, CAS 602306-29-6); Palbociclib (PD-0332991); and (2R, 3R)-3-[[2-[[3-[[S(R)]-S-cyclopropylsulfoni midoyl]-phenyl]amino]-5-(trifluoromethyl)-4-pyrimidinyl] oxy]-2-butatanol (BAY 10000394);

Checkpoint Kinase (CHK) inhibitors such as 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl) amino]-3-(1H-benzimidazol-2-yl)-6-chloroquinolin-2 (1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL), and CBP501 ((d-Bpa)sws(d-Phe-F5)(d-Cha)rrrqrr); and (αR)-α-amino-N-[5,6-dihydro-2-(1-methyl-1H-pyrazol-4-yl)-6-oxo-1H-pyrrolo[4,3,2-ef][2,3]benzodiazepin-8-yl]-Cyclohexaneacetamide (PF-0477736);

3-Phosphoinositide-dependent kinase-1 (PDK1 or PDPK1) inhibitors such as 7-2-Amino-N-[4-[5-(2-phenanthrenyl)-3-(trifluoromethyl)-1H-pyrazol-1-yl] phenyl]-acetamide (OSU-03012, CAS 742112-33-0); Pyrrolidine-1-carboxylic acid (3-{5-bromo-4-[2-(1H-imidazol-4-yl)-ethylamino]-pyrimidin-2-ylamino}-phenyl)-amide (BX912, CAS 702674-56-4); and 4-Dodecyl-N-1,3,4-thiadiazol-2-yl-benzenesulfonamide (PHT-427, CAS 1191951-57-1);

Pyruvate Dehydrogenase Kinase (PDK) inhibitors such as (+)-Dehydroabietylamine; Dichloroacetic acid (DCA); and Leelamine;

Protein Kinase B (PKB) or AKT inhibitors such as 8-[4-(1-Aminocyclobutyl)phenyl]-9-phenyl-1,2,4-triazolo[3,4-f][1,6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinyl-methoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl) methoxy]-6H-dibenzo[b,d]pyran-6-one (palomid 529, P529, or SG-00529); Tricirbine (6-Amino-4-methyl-8-(τ3-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7);

Protein Kinase C (PKC) activators such as Bryostatin I (bryo-1) and Sotrastaurin (AEB071); B-RAF inhibitors such as Regorafenib (BAY73-4506, CAS 755037-03-7); Tuvizanib (AV951, CAS 475108-18-0); Vemurafenib (Zelboraf®, PLX-4032, CAS 918504-65-1); Encorafenib (also known as LGX818); 1-Methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-Hydroxyethyl)-3-(pyridin-4-yl)-1H-pyrazol-4-yl]-2,3-dihydroinden-1-one oxime (GDC-0879, CAS 905281-76-7); 5-[2-[4-[2-(Dimethylamino)ethoxy]phenyl]-5-(4-pyridinyl)-1H-imidazol-4-yl]-2,3-dihydro-1H-Inden-1-one oxime (GSK2118436 or SB590885); (+/−)-Methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662) and N-(3-(5-chloro-1H-pyrrolo[2,3-b]pyridine-3-carbonyl)-2,4-difluorophenyl)propane-1-sulfonamide (also known as PLX4720);

C-RAF Inhibitors such as Sorafenib (Nexavar®); 3-(Dimethylamino)-N-[3-[(4-hydroxybenzoyl)amino]-4-methylphenyl]-benzamide (ZM336372, CAS 208260-29-1); and 3-(1-cyano-1-methylethyl)-N-[3-[(3,4-dihydro-3-methyl-4-oxo-6-quinazolinyl)amino]-4-methylphenyl]-benzamide (AZ628, CAS 1007871-84-2);

Human Granulocyte colony-stimulating factor (G-CSF) modulators such as Filgrastim (Neupogen®); Sunitinib malate (Sutent®); Pegilgrastim (Neulasta®) and Quizartinib (AC220, CAS 950769-58-1);

RET Inhibitors such as Sunitinib malate (Sutent®); Vandetanib (Caprelsa®); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Sorafenib (BAY 43-9006); Regorafenib (BAY73-4506, CAS 755037-03-7); and Danusertib (PHA-739358);

FMS-like Tyrosine kinase 3 (FLT3) Inhibitors or CD135 such as Sunitinib malate (Sutent®); Quizartinib (AC220, CAS 950769-58-1); N-[(1-Methyl-4-piperidinyl)methyl]-3-[3-(trifluoromethoxy)phenyl]-Imidazo[1,2-b]pyridazin-6-amine sulfate (SGI-1776, CAS 1173928-26-1); and Vargatef (BIBF1120, CAS 928326-83-4);

c-KIT Inhibitors such as Pazopanib (Votrient®); Dovitinib dilactic acid (TK1258, CAS 852433-84-2); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Masitinib (Masivet®); Regorafenib (BAY73-4506, CAS 755037-03-7); Tivozanib (AV951, CAS 475108-18-0); Vatalanib dihydrochloride (PTK787, CAS 212141-51-0); Telatinib (BAY57-9352, CAS 332012-40-5); Foretinib (GSK1363089, formerly XL880, CAS 849217-64-7); Sunitinib malate (Sutent®); Quizartinib (AC220, CAS 950769-58-1); Axitinib (Inlyta®); Dasatinib (BMS-345825); and Sorafenib (Nexavar®);

Bcr/Abl kinase inhibitors such as Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1 S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3);

IGF-1R inhibitors such as Linsitnib (OSI-906); [7-[trans-3-[(Azetidin-1-yl)methyl]cyclobutyl]-5-(3-benzyloxyphenyl)-7H-pyrrolo[2,3-d]pyrimidin-4-yl]amine (AEW541, CAS 475488-34-7); [5-(3-Benzyloxyphenyl)-7-[trans-3-[(pyrrolidin-1-yl)methyl]cyclobutyl]-7H-pyrrolo[2,3-d]pyrimidin-4-yl]amine (ADW742 or GSK552602A, CAS 475488-23-4); (2-[[3-Bromo-5-(1,1-dimethylethyl)-4-hydroxyphenyl]methylene]-propanedinitrile (Tyrphostin AG1024, CAS 65678-07-1); 4-[[(2S)-2-(3-Chlorophenyl)-2-hydroxyethyl]amino]-3-[7-methyl-5-(4-morpholinyl)-1H-benzimidazol-2-yl]-2(1H)-pyridinone (BMS536924, CAS 468740-43-4); 4-[2-[4-[[(2S)-2-(3-Chlorophenyl)-2-hydroxyethyl]amino]-1,2-dihydro-2-oxo-3-pyridinyl]-7-methyl-1H-benzimidazol-5-yl]-1-piperazinepropanenitrile (BMS554417, CAS 468741-42-6); (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide (BMS754807, CAS 1001350-96-4); Picropodophyllotoxin (AXL1717); and Nordihydroguareacetic acid;

PIM Kinase inhibitors such as 1,10-Dihydropyrrolo[2,3-a]carbazole-3-carbaldehyde (DHPCC-9); N-[(1-Methyl-4-piperidinyl)methyl]-3-[3-(trifluoromethoxy)phenyl]-Imidazo[1,2-b]pyridazin-6-amine sulfate (SGI-1776, CAS 1173928-26-1); and CX-6258 (described in *ACS Med. Chem. Lett.*, 2012, 3 (2), pp 135-139);

MET inhibitors such as Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU 11271); (3Z)-N-(3-Chlorophenyl)-3-({3,5-dimethyl-4-[(4-methyl piperazin-1-yl)carbonyl]-1H-pyrrol-2-yl}methylene)-N-methyl-2-oxoindoline-5-sulfonamide (SU 11274); (3Z)-N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)

methyl]sulfonyl]-3-[[3,5-dimethyl-4-[[(2R)-2-(1-pyrrolidinylmethyl)-1-pyrrol idinyl]carbonyl]-1H-pyrrol-2-yl]methylene]-1,3-dihydro-2H-indol-2-one (PHA665752, CAS 477575-56-7);

Human Epidermal Growth Factor Receptor 2 (HER2 receptor) (also known as Neu, ErbB-2, CD340, or p185) inhibitors such as Trastuzumab (Herceptin®); Pertuzumab (Omnitarg®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8);

Epidermal growth factor receptor (EGFR) inhibitors such as Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4 (dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (Cl-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα, 5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4); Hedgehog antagonists such as Vismodegib (2-chloro-N-[4-chloro-3-(2-pyridinyl)phenyl]-4-(methylsulfonyl)-benzamide, GDC-0449, and described in PCT Publication No. WO 06/028958); 1-(4-Chloro-3-(trifluoromethyl)phenyl)-3-((3-(4-fluorophenyl)-3,4-dihydro-4-oxo-2-quinazolinyl)methyl)-urea (CAS 330796-24-2); N-[(2S,3R,3'R,3αS,4'αR,6S,6'αR,6'bS,7αR, 12'αS, 12'bS)-2',3',3a,4, 4',4'a,5,5',6,6',6'a,6'b,7,7',7a,8',10',12',12'a, 12'b-Eicosahydro-3,6,11',12'b-tetramethylspiro[furo[3,2-b]pyridine-2(3H),9'(1'H)-naphth[2,1-a]azulen]-3'-yl]-methanesulfonamide (IP1926, CAS 1037210-93-7); 4-Fluoro-N-methyl-N-[1-[4-(1-methyl-1H-pyrazol-5-yl)-1-phthalazinyl]-4-piperidinyl]-2-(trifluoromethyl)-benzamide (LY2940680, CAS 1258861-20-9); and Erismodegib (LDE225);

mTOR inhibitors such as Temsirolimus (Torisel®); Ridaforolimus (formally known as deferolimus, (1R,2R, 4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23,29,35-hexamethyl-2,3,10, 14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1); N-[4-[[[3-[(3,5-dimethoxyphenyl)amino]-2-quinoxalinyl]amino]sulfonyl]phenyl]-3-methoxy-4-methyl-benzamide (XL765, also known as SAR245409); and (1R,4R)-4-(4-amino-5-(7-methoxy-1H-indol-2-yl)imidazo[1,5-f][1,2,4]triazin-7-yl)cyclohexanecarboxylic acid (OSI-027);

Phosphoinositide 3-kinase (PI3K) inhibitors such as 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4αR,5R,6αS,9αR)-5-(Acetyloxy)-1-[(di-2-propenylamino)methylene]-4,4a, 5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-36-6); 2-Amino-8-ethyl-4-methyl-6-(1H-pyrazol-5-yl)pyrido[2,3-d]pyrimidin-7 (8H)-one (SAR 245409 or XL 765); 1,3-Dihydro-8-(6-methoxy-3-pyridinyl)-3-methyl-1-[4-(1-piperazinyl)-3-(trifluoromethyl)phenyl]-2H-imidazo[4,5-c]quinolin-2-one, (2Z)-2-butenedioate (1:1) (BGT 226); 5-Fluoro-3-phenyl-2-[(1S)-1-(9H-purin-6-ylamino)ethyl]-4(3H)-quinazolinone (CAL101); 2-Amino-N-[3-[N-[3-[(2-chloro-5-methoxyphenyl)amino]quinoxalin-2-yl]sulfamoyl]phenyl]-2-methylpropanamide (SAR 245408 or XL 147); and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (BYL719);

Bcl-2 protein family inhibitors such as 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−) BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4′-Chloro[1,1′-biphenyl]-2-yl) methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6);

Mitogen-activated protein kinase (MEK) inhibitors such as XL-518 (also known as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); Benimetinib (6-(4-bromo-2-fluorophenylamino)-7-fluoro-3-methyl-3H-benzoimidazole-5-carboxylic acid (2-hydroxyethyoxy)-amide, also known as MEK162, CAS 1073666-70-2, described in PCT Publication No. WO2003077914); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione (also known as E6201 and described in PCT Publication No. WO2003076424); 2′-Amino-3′-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); Trametinib dimethyl sulfoxide (GSK-1120212, CAS 1204531-25-80); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl) amino]-N-(2-hydroxyethoxy)-5-[(3-oxo-[1,2]oxazinan-2-yl) methyl]benzamide (CH 4987655 or Ro 4987655);

P38 MAPK inhibitors such as Orantinib (TSU-68, CAS 252916-29-3); Dilmapimod (SB681323, CAS 444606-18-2); 6-[(Aminocarbonyl)(2,6-difluorophenyl) amino]-2-(2,4-difluorophenyl)-3-pyridinecarboxamide (VX702); 8-Phenyl-2-(morpholin-4-yl)-chromen-4-one (LY294002, CAS 154447-36-6); 4-[4-(4-fluorophenyl)-2-[4-(methylsulfinyl)phenyl]-1H-imidazol-5-yl]-pyridine (SB203580, CAS 152121-47-6); 4-[4-(4-Fluorophenyl)-2-[4-(methylsulfinyl)phenyl]-1H-imidazol-5-yl]-pyridine (SB203580, CAS 152121-47-6); trans-4-[4-(4-Fluorophenyl)-5-(2-methoxy-4-pyrimidinyl)-1H-imidazol-1-yl]-cyclohexanol (SB 239063, CAS 193551-21-2); 6-(4-Fluorophenyl)-2,3-dihydro-5-(4-pyridinyl)-imidazo[2,1-b]thiazole (SKF 86002, CAS 72873-74-6); 5-(2,6-dichlorophenyl)-2-[(2,4-difluorophenyl)thio]-6H-pyrimido[1,6-b] pyridazin-6-one (VX745, CAS 209410-46-8); Talmapimod (SC10469, CAS 309913-83-5); 1-[4-[3-(4-chlorophenyl)-4-(4-pyrimidinyl)-1H-pyrazol-5-yl]-1-piperidinyl]-2-hydroxy-ethanone (SD0006, CAS 1184301-42-5); Dilmapimod (SB681323, CAS 444606-18-2); 3-Bromo-4-[(2,4-difluorobenzyl)oxy]-1-[5-[(methylamino)carbonyl]-2-methylphenyl]-6-methylpyridin-2(1H)-one (PH797804, CAS 586379-66-0); 4-[[5-[(Cyclopropylamino)carbonyl]-2-methylphenyl]amino]-5-methyl-N-propyl-pyrrolo[2,1-f][1,2,4]triazine-6-carboxamide (BMS-582949, CAS 623152-17-0); Pamapimod (R1503, CAS 449811-01-2); 2-[(Hexahydrocyclopenta[c]pyrrol-2(1H)-yl) amino]-8-methyl-6-(2-methylphenyl)-pyrido[2,3-d]pyrimidin-7(8H)-one (AW814141, CAS 905285-51-0); 4-[5-(4-Fluorophenyl)-2-(methylthio)-1H-imidazol-4-yl]-N-(1-phenylethyl)-2-pyridinamine, (9CI) (ML 3403); and rel-6-Chloro-5-[[(2R,5S)-4-[(4-fluorophenyl)methyl]-2,5-dimethyl-1-piperazinyl]carbonyl]-N, N,1-trimethyl-α-oxo-1H-Indole-3-acetamide (SCIO 282 and SD 282);

JAK inhibitors such as Ruxolitinib (Jakafi®); Tofacitinib (CP690550); Axitinib (AG013736, CAS 319460-85-0); 5-Chloro-N$^2$-[(1S)-1-(5-fluoro-2-pyrimidinyl)ethyl]-N$^4$-(5-methyl-1H-pyrazol-3-y)-I2,4-pyrimidinediamine (AZD1480, CAS 935666-88-9); (9E)-15-[2-(1-Pyrrolidinyl)ethoxy]-7,12,26-Trioxa-19,21,24-triazatetracyclo[18.3.1.1$^{2,5}$.1$^{14,18}$]-hexacosa-1(24),2,4, 9,14,16,18(25),20,22-nonaene (SB-1578, CAS 937273-04-6); Momelotinib (CYT 387); Baricitinib (INCB-028050 or LY-3009104); Pacritinib (SB1518); (16E)-14-Methyl-20-Oxa-5,7,14,27-tetraazatetracyclo [19.3.1.12,6.18,12]heptacosa-1 (25),2,4,6(27),8,10,12 (26), 16,21,23-decaene (SB 1317); Gandotinib (LY 2784544); N,N-Cicyclopropyl-4-[(1,5-dimethyl-1H-pyrazol-3-yl)amino]-6-ethyl-1,6-dihydro-1-methyl-imidazo[4,5-d]pyrrolo[2,3-b]pyridine-7-carboxamide (BMS 911543);

Alkylating agents such as Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®);

Aromatase inhibitors such as Exemestane (Aromasin®); Letrozole (Femara®); and Anastrozole (Arimidex®);

Topoisomerase I inhibitors such as Irinotecan (Camptosar®); Topotecan hydrochloride (Hycamtin®); and 7-Ethyl-10-hydroxycampothecin (SN38);

Topoisomerase II inhibitors such as Etoposide (VP-16 and Etoposide phosphate, Toposar®, VePesid® and Etopophos®); Teniposide (VM-26, Vumon®); and Tafluposide;

DNA Synthesis inhibitors such as Capecitabine (Xeloda®); Gemcitabine hydrochloride (Gemzar®); Nelarabine ((2R,3S,4R,5R)-2-(2-amino-6-methoxypurin-9-yl)-5-(hydroxymethyl)oxolane-3,4-diol, Arranon® and Atriance®); and Sapacitabine (1-(2-cyano-2-deoxy-β-D-arabinofuranosyl)-4-(palmitoylamino) pyrimidin-2(1H)-one);

Folate Antagonists or Antifolates such as Trimetrexate glucuronate (Neutrexin®); Piritrexim isethionate (BW201U); Pemetrexed (LY231514); Raltitrexed (Tomudex®); and Methotrexate (Rheumatrex®, Trexal®);

Immunomodulators such as Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics) or such as one or more of an activator of a costimulatory molecule (e.g. an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand), or such as one or more inhibitors of an immune checkpoint molecule (e.g. one or more inhibitors of PD-1, PD-L1, PD-L2, CTLA4, TIM3, LAG3, VISTA, BTLA, TIGIT, LAIR1, CD160, 2B4 and/or TGFR beta);

Proapoptotic receptor agonists (PARAs) including DR4 (TRAILR1) and DR5 (TRAILR2) such as Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo);

Phospholipase A2 ($PLA_2$) inhibitors such as Manoalide; E-(3-Acetamide-1-benzyl-2-ethylindolyl-5-oxy)propane sulfonic acid (LY311727); Anagrelide (Agrylin®); Methyl arachidonyl fluorophosphonate (MAFP); Arachidonyl trifluoromethyl ketone ($AACOCF_3$); (E)-6-(1-bromoethyle)tetrahydro-3-(1-naphthalenyl)-2H-pyran-2-one (Bromoenol lactone or BEL); R-Bromoenol lactone (R-BEL); S-Bromoenol lactone (S-BEL); Diisopropylfluorophosphate (DFP); Phenylmethylsulfonylfluoride (PMSF); and Pefabloc (CAS 34284-75-8, 4-[2-aminoethyl]benzenesulfonyl fluoride); SRC inhibitors such as Dasatinib (Sprycel®); Saracatinib (AZD0530, CAS 379231-04-6); Bosutinib (SKI-606, CAS 380843-75-4); 5-[4-[2-(4-Morpholinyl)ethoxy] phenyl]-N-(phenylmethyl)-2-pyridineacetamide (KX2-391, CAS 897016-82-9); and 4-(2-Chloro-5-methoxyanilino)-6-methoxy-7-(1-methylpiperidin-4-ylmethoxy) quinazoline (AZM475271, CAS 476159-98-5);

Osteoclastic bone resorption inhibitors such as Zoledronate (Zometa®); Ibandronate (Boniva®); Alendronate (Fosamax®); Risedronate (Actonel®, Atelvia®, and Benet®); and Mineral trioxide aggregate (MTA);

G-Protein-coupled Somatostatin receptors Inhibitors such as Octreotide (also known as octreotide acetate, Sandostatin® and Sandostatin LAR®); Lanreotide acetate (CAS 127984-74-1); Seglitide (MK678); Vapreotide acetate (Sanvar®); and Cyclo(D-Trp-Lys-Abu-Phe-MeAla-Tyr)(BIM23027);

Interleukin-11 and Synthetic Interleukin-11 (IL-11) such as Oprelvekin (Neumega®); Erythropoietin and Synthetic erythropoietin such as Erythropoietin (Epogen® and Procrit®); Darbepoetin alfa (Aranesp®); Peginesatide (Hematide®); and EPO covalently linked to polyethylene glycol (Micera®);

Receptor Activator for Nuclear Factor κ B (RANK) inhibitors such as Denosumab (Prolia® and Xgeva®); Thrombopoietin mimetic peptibodies such as Romiplostim (Nplate®); Cell growth stimulators such as Palifermin (Kepivance®); Erythropoietin (Epogen® and Procrit®); Darbepoetin alfa (Aranesp®); Peginesatide (Hematide®); and EPO covalently linked to polyethylene glycol (Micera®);

Histone deacetylase (HDAC) inhibitors such as Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic [L-alanyl-D-alanyl-(2S)-η-oxo-L-α-aminooxiraneoctanoyl-D-prolyl] (HC-toxin); Cyclo [(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide); and Depudecin (4,5:8,9-dianhydro-1,2,6,7,11-pentadeoxy-D-threo-D-ido-Undeca-1,6-dienitol);

Biologic response modifiers including therapeutics such as interferons, interleukins, colony-stimulating factors, monoclonal antibodies, vaccines (therapeutic and prophylactic), gene therapy, and nonspecific immunomodulating agents such as Interferon alpha (Intron®, Roferson®-A); Interferon beta; Interferon gamma; Interleukin-2 (IL-2 or aldesleukin, Proleukin®); Filgrastim (Neupogen®); Sargramostim (Leukine®); Erythropoietin (epoetin); Interleukin-11 (oprelvekin); Imiquimod (Aldara®); Lenalidomide (Revlimid®); Rituximab (Rituxan®); Trastuzumab (Herceptin®); *Bacillus* calmette-guerin (theraCys® and TICE® BCG); Levamisole (Ergamisol®); and Denileukin diftitox (Ontak®);

Anti-tumor antibiotics such as Doxorubicin (Adriamycin® and Rubex®); Bleomycin (Lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence™); Idarubicin (Idamycin®, Idamycin PFS®); Mitomycin C (Mutamycin®); Geldanamycin; Herbimycin; Ravidomycin; and Desacetylravidomycin;

Anti-microtubule or Anti-mitotic agents such as Vinca Alkaloids (such as Vinorelbine tartrate (Navelbine®), Vincristine (Oncovin®), and Vindesine (Eldisine®)); Taxanes (such as paclitaxel and docetaxel); and Estramustine (Emcyl® or Estracyt®); Plant Alkaloids such as Paclitaxel (Taxol and Onxal™); Paclitaxel protein-bound (Abraxane®); Vinblastine (also known as vinblastine sulfate, vincaleukoblastine and VLB, Alkaban-AQ® and Velban®); Vincristine (also known as vincristine sulfate, LCR, and VCR, Oncovin® and Vincasar Pfs®); and Vinorelbine (Navelbine®);

Taxane anti-neoplastic agents such as Paclitaxel (Taxol®); Docetaxel (Taxotere®); Cabazitaxel (Jevtana®, 1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate); and Larotaxel ((2α,3ξ,4α,5β,7α, 10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate); Cathepsin K inhibitors such as Odanacatib (MK-0822, N-(1-cyanocyclopropyl)-4-fluoro-N²-{(1S)-2,2,2-trifluoro-1-[4'-(methylsulfonyl)biphenyl-4-yl]ethyl}-L-leucinamide and described in PCT Publication no. WO 03/075836); Balicatib (N-(1-(((Cyanomethyl)carbamoyl)cyclohexyl)-4-(4-propylpiperazin-1-yl)benzamide, AAE581, CAS 354813-19-7); and Relacatib (SB-462795, CAS 362505-84-8);

Epothilone B analogs such as Ixabepilone (Lxempra®); Patupilone (EP0906); Sagopilone (CAS 305841-29-6); and 21-Aminoepothilone B (BMS-310705, CAS 280578-49-6); Heat Shock Protein (HSP) inhibitors such as Tanespimycin (17-allylamino-17-demethoxy-geldanamycin, also known as KOS-953 and 17-AAG, available from SIGMA, and described in U.S. Pat. No. 4,261,989); Retaspimycin (IP1504), Ganetespib (STA-9090); [6-Chloro-9-(4-methoxy-3,5-dimethylpyridin-2-ylmethyl)-9H-purin-2-yl]amine (BII B021 or CNF2024, CAS 848695-25-0); trans-4-[[2-(Aminocarbonyl)-5-[4,5,6,7-tetrahydro-6,6-dimethyl-4-oxo-3-(trifluoromethyl)-1H-indazol-1-yl]phenyl]amino]cyclohexyl glycine ester (SNX5422 or PF04929113, CAS 908115-27-5); 5-[2,4-Dihydroxy-5-(1-methylethyl)phenyl]-N-ethyl-4-[4-(4-morpholinylmethyl)phenyl]-3-Isoxazolecarboxamide (AUY922, CAS 747412-49-3); and 17-Dimethylaminoethylamino-17-demethoxy-geldanamycin (17-DMAG); Farnesyl Transferase Inhibitors (FTI) such as Tipifarnib (R115777, Zarnestra®); Lonafarnib (SCH66336); [2S-[1 [R*(R*)],2R*(S*),3R*]]-2-[[2-[[2-[(2-Amino-3-mercaptopropyl)amino]-3-methylpentyl]oxy]-1-oxo-3-phenylpropyl]amino]-4-(methylsulfonyl)-butanoic acid, 1-methylethyl ester (L-744832, CAS 160141-09-3); and (R)-2,3,4,5-Tetrahydro-1-(1H-imidazol-4-ylmethyl)-3-(phenylmethyl)-4-(2-thienylsulfonyl)-1H-1,4-benzodiazepine-7-carbonitrile (BMS-214662, CAS 195987-41-8);

Thrombopoietin (TpoR) agonists such as Eltrombopag (SB497115, Promacta® and Revolade®); and Romiplostim (Nplate®);

Proteasome inhibitors such as Bortezomib (Velcade®); Ixazomib citrate (MLN9708, CAS 1201902-80-8); Danoprevir (RG7227, CAS 850876-88-9); Ixazomib (MLN2238, CAS 1072833-77-2); and (S)—N-[(phenylmethoxy)carbonyl]-L-leucyl-N-(1-formyl-3-methylbutyl)-L-Leucinamide (MG-132, CAS 133407-82-6);

Kinesis Spindle Protein (KSP) inhibitors (also known as Eg5 inhibitors) such as Monastrol (Ethyl 4-(3-hydroxyphenyl)-6-methyl-2-sulfanylidene-3,4-dihydro-1H-pyrimidine-5-carboxylate); Ispinesib (SB715992); (2S)-4-(2,5-Difluorophenyl)-N-[(3R,4S)-3-fluoro-1-methyl-4-piperidinyl]-2,5-dihydro-2-(hydroxymethyl)-N-methyl-2-phenyl-1H-pyrrole-1-carboxamide (MK-0731, CAS 845256-65-7); Litronesib (LY2523355, CAS 910634-41-2); and (2S)-2-(3-Aminopropyl)-5-(2,5-difluorophenyl)-N-methoxy-N-methyl-2-phenyl-1,3,4-thiadiazole-3(2H)-carboxamide (ARRY520); and 9-Cyclopentyl-7,9-dihydro-2-[[2-methoxy-4-[(1-methyl-4-piperidinyl)oxy]phenyl]amino]-7-methyl-8H-purin-8-one (AZ 3146);

Polo-like kinase (Plk) inhibitors such as (R)-4-[(8-Cyclopentyl-7-ethyl-5,6,7,8-tetrahydro-5-methyl-6-oxo-2-pteridinyl)amino]-3-methoxy-N-(1-methyl-4-piperidinyl)benzamide (B12536, CAS 755038-02-9); Wortmannin; Morin; Quercetin; Volasertib (B16727); 8-Phenyl-2-(morpholin-4-yl)-chromen-4-one (LY294002); 5-[6-[(4-Methylpiperazin-1-yl)methyl]-1H-benzimidazol-1-yl]-3-[[(1R)-1-[2-(trifluoromethyl)phenyl]ethyl]oxy]-thiophene-2-carboxamide (GSK461364); (E)-4-[2-[2-[N-Acetyl-N-[(p-methoxyphenyl)sulfonyl]amino]phenyl]ethenyl]pyridine 1-oxide (HMN214); and Rigosertib (ON 01910);

Adrenal steroid inhibitors such as Aminoglutethimide (Cytadren®); Trilostane (Modrenal® or Vetoryl®); and Mitotane (Lysodren®);

Anti-androgens such as Nilutamide (Nilandron® and Anandron®); Bicalutamide (Casodex®); Megestrol (Megace®); Cyproterone acetate (Cyprostat®, Androcur@, or Cyproterone®), and Flutamide (Fulexin™ or Eulexin®); Leuprolide (Lupron@, Viadur@ or Eligard®); Foserelin (Zoladex®); Triptorelin (Trelstar Depot®); Abarelix (Plenaxis®); and Finasteride (Andozac® or MK-906);

Anabolic Steroids such as Fluoxymesterone (Halotestin®); Oxymetholone (Anadrol 50®); Oxandrolone (Oxandrin)®; and Stanozolol (Winstrol®);

Proteasome inhibitors such as Bortezomib (Velcade®); Carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); Marizomib (NPI-0052); Ixazomib citrate (MLN-9708); Delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912);

Gonadotropin-releasing hormone (GnRH) receptor agonists such as Leuprolide or leuprolide acetate (Viadure®, Eligard® and Lupron®); Buserelin (Suprefact® or Suprecor®); Nafarelin (Synarel®); Histrelin (Supprelin LA® or Vantas®); Goserelin (Zoladex®); Deslorelin (Suprelorin® or Ovuplant®); Degarelix (Firmagon®); and Triptorelin (Decapeptyl®, Diphereline®, Goapeptyl®, Trelstart® or Variopeptyl® 0.1);

HPV vaccines such as Human papilloma virus (HPV) vaccine (Cervarix® (ATC code J07BM02), and Gardasil® (ATC code J07BM01);

Iron Chelating agents such as Silybin; Curcumin; Ethylene diamine tetraacetic acid (EDTA); Triapine (3-aminopyridine-2-carboxaldehyde thiosemicarbazone); Di-2-pyridylketone thiosemicarbazone; Di-2-pyridylketone-4,4,-dimethyl-3-thiosemicarbazone; Desferrioxamine; and Deferasinox (Exjade®);

Anti-metabolites such as Claribine (2-chlorodeoxyadenosine, Leustatin®); 5-Fluorouracil (Adrucil®); 6-Thioguanine (Purinethol®); Pemetrexed (Alimta®); Cytarabine (also known as arabinosylcytosine (Ara-C), Cytosar-U®); Cytarabine liposomal (also known as Liposomal Ara-C, DepoCyt™); Decitabine (Dacogen®); Hydroxyurea (Hydrea®, Droxia™ and Mylocel™); Fludarabine (Fludara®); Floxuridine (FUDR®); Methotrexate (also known as amethopterin, methotrexate sodim (MTX); Rheumatrex® and Trexall™); Pentostatin (Nipent®); Raltitrexed (Tomudex®); and Pralatrexate (Folotyn™);

Bisphosphonates such as Pamidronate (Aredia®); Zoledronic acid or Zoledronate (Zometa®, Zomera®, Aclasta®, or Reclast®); Alendronate (Fosamax®); Risedronate (Actonel®); and Ibandronate (Boniva®);

Demethylating agents such as 5-Azacitidine (Vidaza®); and Decitabine (Dacogen®);

Retinoids such as Alitretinoin (9-cis-retinoic acid, Panretin®); Tretinoin (all-trans retinoic acid, also known as ATRA, Vesanoid®); Isotretinoin (13-cis-retinoic acid, Accutane®, Amnesteem®, Claravis®, Clarus®, Decutan®, Isotane®, Izotech®, Oratane®, Isotret®, and Sotret®); Bexarotene (Targretin®), Liposomal retinoic acid; Tazarotene (Tazorac®, Avage® or Zorac®); all-trans retinol; all-trans retinaldehyde (also known as all-trans retinal); all-trans 4-oxo retinoic acid; retinyl palmitate; and retinyl acetate;

Cytokines such as Interleukin-2 (also known as aldesleukin and IL-2, Proleukin®); Interleukin-11 (also known as oprevelkin, Neumega®); and Alpha interferon alfa (also known as IFN-alpha, Intron® A, and Roferon-A®);

Estrogen receptor downregulators such as Fulvestrant (Faslodex®);

Anti-estrogens such as Tamoxifen (Novaldex®); Toremifene (Fareston®); and Fulvestrant (Faslodex®);

Selective estrogen receptor modulators (SERMs) such as Raloxifene (Evista®); Bazedoxifene; Tamoxifen (Nolvadex®); and Toremifene (Fareston®);

Leutinizing hormone releasing hormone (LHRH) agonists such as Goserelin (Zoladex®); and Leuprolide acetate (Eligard® or Lupron®);

Progesterones such as Megestrol (also known as megestrol acetate, Megace®); 17 α-hydroxylase/C17,20 lyase (CYP17A1) inhibitors such as Abiraterone acetate (Zyitga®);

Miscellaneous cytotoxic agents such as Arsenic trioxide (Trisenox®); Asparaginase (also known as L-asparaginase, *Erwinia* L-asparaginase, Elspar® and Kidrolase®); and Asparaginase *Erwinia Chrysanthemi* (Erwinaze®);

C-C Chemokine receptor 4 (CCR4) Antibody such as Mogamulizumab (Potelligent®); CD20 antibodies such as Rituximab (Riuxan® and MabThera®); and Tositumomab (Bexxar®) and Ofatumumab (Arzerra®);

CD20 Antibody Drug Conjugates such as Ibritumomab tiuxetan (Zevalin®); and Tositumomab;

CD22 Antibody Drug Conjugates such as Inotuzumab ozogamicin (also referred to as CMC-544 and WAY-207294, available from Hangzhou Sage Chemical Co., Ltd.);

CD30 mAb-cytotoxin Conjugates such as Brentuximab vedotin (Adcetrix®);

CD33 Antibody Drug Conjugates such as Gemtuzumab ozogamicin (Mylotarg®);

CD40 antibodies such as Dacetuzumab (also known as SGN-40 or huS2C6, available from Seattle Genetics, Inc);

CD52 antibodies such as Alemtuzumab (Campath®);

Anti-CS1 antibodies such as Elotuzumab (HuLuc63, CAS No. 915296-00-3);

CTLA-4 antibodies such as Tremelimumab (lgG2 monoclonal antibody available from Pfizer, formerly known as ticilimumab, CP-675,206);

and Ipilimumab (CTLA-4 antibody, also known as MDX-010, CAS No. 477202-00-9);

p53-MDM2 inhibitors such as (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RG7112), 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid (RG7388), SAR299155, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232), {(3R,5R,6S)-5-(3-Chlorophenyl)-6-(4-chlorophenyl)-1-[(2S,3S)-2-hydroxy-3-pentanyl]-3-methyl-2-oxo-3-piperidinyl}acetic acid (AM-8553), (±)-4-[4,5-Bis(4-chlorophenyl)-2-(2-isopropoxy-4-methoxy-phenyl)-4,5-dihydro-imidazole-1-carbonyl]-piperazin-2-one (Nutlin-3), 2-Methyl-7-[Phenyl(phenylamino)methyl]-8-quinolinol (NSC 66811), 1-N-[2-(1H-indol-3-yl)ethyl]-4-N-pyridin-4-ylbenzene-1,4-diamine (JNJ-26854165), 4-[4,5-bis(3,4-chlorophenyl)-2-(2-isopropoxy-4-methoxy-phenyl)-4,5-dihydro-imidazole-1-carboxyl]-piperazin-2-one (Caylin-1), 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2), 5-[[3-Dimethylamino)propyl]amino]-3,10-dimethylpyrimido[4,5-b]quinoline-2,4(3H,10H)-dione dihydrochloride (HLI373) and trans-4-Iodo-4'-boranyl-chalcone (SC204072);

p53 activators.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef@, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®). Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of any of examples 1 to 30 described herein) or a pharmaceutically acceptable salt thereof together with a pharmaceutically acceptable carrier suitable for administration to a human or animal subject, either alone or together with other anti-cancer agents, such as those described above.

In one embodiment, the present invention provides methods of treating a human or animal subject in need of such treatment, comprising administering to the subject a therapeutically effective amount of a compound of the present invention (e.g., a compound of any of examples 1 to 30 described herein) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by FGFR4, wherein the medicament is prepared for administration with another therapeutic agent. The invention also provides the use of another therapeutic agent for treating a disease or condition mediated by FGFR4, wherein the medicament is administered with a compound of formula (I).

The invention also provides a compound of formula (I) for use in a method of treating a disease or condition mediated by FGFR4, wherein the compound of formula (I) is prepared for administration with another therapeutic agent. The invention also provides another therapeutic agent for use in a method of treating a disease or condition mediated by FGFR4, wherein the other therapeutic agent is prepared for administration with a compound of formula (I). The invention also provides a compound of formula (I) for use in a method of treating a disease or condition mediated by FGFR4, wherein the compound of formula (I) is administered with another therapeutic agent. The invention also provides another therapeutic agent for use in a method of treating a disease or condition mediated by FGFR4, wherein the other therapeutic agent is administered with a compound of formula (I).

The invention also provides the use of a compound of formula (I) for treating a disease or condition mediated by FGFR4, wherein the patient has previously (e.g. within 24 hours) been treated with another therapeutic agent. The invention also provides the use of another therapeutic agent for treating a disease or condition mediated by FGFR4, wherein the patient has previously (e.g. within 24 hours) been treated with a compound of formula (I).

In one embodiment, the other therapeutic agent is selected from an anti-cancer agent.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesise the compounds of the present invention are either commercially available or can be produced by organic synthesis methods known to one of ordinary skill in the art.

Further, the compounds of the present invention can be produced by organic synthesis methods known to one of ordinary skill in the art as shown in the following examples.

Abbreviations

| Abbreviation | Description |
| --- | --- |
| aq. | aqueous |
| conc. | concentrated |
| DAST | (diethylamino)sulfur trifluoride |
| dba | dibenzylideneacetone |
| DCC | Dicyclohexylcarbodiimide |
| DCM | dichloromethane |
| DIPEA | N,N-diisopropylethylamine, N-ethyl-N-isopropylpropan-2-amine |
| DMA | N,N-dimethylacetamide |
| DMAP | 4-dimethylaminopyridine |
| DME | 1,2-dimethoxyethane |
| DMF | N,N-dimethylformamide |
| DMSO | dimethylsulfoxide |

-continued

| Abbreviation | Description |
| --- | --- |
| DMSO-$d_6$ | Hexadeuterodi methyl sulfoxide |
| dppf | 1,1'-bis(diphenylphosphino)ferrocene |
| ESI-MS | Electrospray ionization mass spectroscopy |
| h | hour |
| HPLC | High-performance liquid chromatography |
| KHMDS | Potassium hexamethyldisilazide |
| LC-MS | liquid chromatography and mass spectrometry |
| LiHMDS | Lithium hexamethyldisilazide |
| M | molar |
| min | minutes |
| NIS | N-iodosuccinimide |
| NMP | N-methylpyrrolidinone, 1-methyl-2-pyrrolidinone |
| NMR | Nuclear magnetic resonance |
| org. | organic |
| RP | Reverse phase |
| sat | saturated |
| SFC | Supercritical fluid chromatography |
| TBAF | tetrabutylammonium fluoride |
| TFA | trifluoroacetic acid |
| THF | tetrahydrofurane |
| $t_R$ or Rt | Retention time (if not indicated, in minutes) |
| UPLC | Ultra-performance liquid chromatography |

Analytical Details

NMR: Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (d-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses.

UPLC-MS 1:
System: Waters Acquity UPLC with Waters SQ detector.
Column: Acquity HSS T3 1.8 μm 2.1×50 mm.
Flow: 1.2 ml/min. Column temperature: 50° C.
Gradient: from 2 to 98% B in 1.4 min, A=water+0.05% formic acid+3.75 mM ammonium acetate, B=acetonitrile+0.04% formic acid.

UPLC-MS 3:
System: Waters Acquity UPLC with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 5:
System: Waters Acquity UPLC with Waters SQ detector.
Column: Sunfire C18 3.5 μm 2.1×20 mm.
Flow: 0.62 ml/min. Column temperature: 40° C.
Gradient: from 5 to 100% B in 4 min, A=water+0.1% trifluoroacetic acid, B=acetonitrile+0.1% trifluoroacetic acid.

UPLC-MS 6:
System: Waters Acquity Ultra Performance with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 7:
System: Waters Acquity Ultra Performance with Waters SQ detector.
Column: Acquity HSS T3 1.8 μm 2.1×50 mm.

Flow: 1.0 ml/min. Column temperature: 60° C.

Gradient: from 5 to 98% B in 1.4 min, A=water+0.05% formic acid+3.75 mM ammonium acetate, B=acetonitrile+0.04% formic acid.

UPLC-MS 8:

System: Waters Acquity Ultra Performance with Waters SQ detector.

Column: Acquity HSS T3 1.8 μm 2.1×50 mm.

Flow: 1.4 ml/min. Column temperature: 60° C.

Gradient: from 1 to 98% B in 1.4 min, A=water+0.05% formic acid+3.75 mM ammonium acetate, B=acetonitrile+0.04% formic acid.

Preparative Methods:

Flash Chromatography System:

System: Teledyne ISCO, CombiFlash Rf.

Column: pre-packed RediSep® Rf cartridges.

Samples were absorbed on Isolute HM-N Sorbent®, or on silica gel, or applied as solutions.

Supercritical fluid chromatoqraphy (SFC 1):

System: Waters SFC 100 prep-system with a Waters 2998 Photodiode Array (PDA) Detector and a Waters 3100 Mass detector.

Column dimension: 250×30 mm.

Columns:

| Manufacturer | code | Name | Particle size | Pore size |
| --- | --- | --- | --- | --- |
| Princeton | PPU | Propyl-pyridyl-urea | 5 μm | 100 Å |
| | 4EP | 4 Ethylpyridine | 5 μm | 60 Å |
| | DEAP | Diethylaminopropyl | 5 μm | 60 Å |
| Reprosil | NH2 | Amino | 5 μm | 100 Å |
| | DNH | Diamino | 5 μm | 100 Å |
| | SiOH | Silica | 5 μm | 100 Å |
| Waters | Hilic | Atlantis Silica OBD | 5 μm | 100 Å |

Flow: 100 ml/min 120 bar back pressure

Gradient: optimized gradient elution using supercritical $CO_2$/MeOH.

Intermediates

Intermediate 1: 6-((2-(6-(hydroxymethyl)pyridin-2-yl)phenyl)amino)nicotinonitrile Ethyl 6-(2-((5-cyanopyridin-2-yl)amino)phenyl)picolinate (Intermediate 2, 110 mg, 0.319 mmol) was suspended in THF (4 ml) and treated with $LiBH_4$ (15.3 mg, 0.703 mmol). The mixture was stirred at room temperature for 5 h. The reaction mixture was quenched with water and diluted in EtOAc. The organic layer was separated and stirred for 1 h with sat. aq. $Na_2CO_3$ at room temperature. The org. layer was then separated, dried over $Na_2SO_4$ and concentrated under vacuum. The crude material was purified by normal phase chromatography (12 g silica gel cartridge, heptanes/EtOAc 100:0 to 0:100) to give the title compound as a beige solid. (UPLC-MS 1) $t_R$ 0.94 min; ESI-MS 303.1 $[M+H]^+$.

Intermediate 2: Ethyl 6-(2-((5-cyanopyridin-2-yl)amino)phenyl)picolinate

Ethyl 6-(2-aminophenyl)picolinate (intermediate 3, 462 mg, 1.91 mmol), 6-bromonicotinonitrile (419 mg, 2.29 mmol), $Pd_2(dba)_3$ (34.9 mg, 0.038 mmol), 4,5-bis(diphenylphosphino)-9,9-dimethylxanthene (77 mg, 0.133 mmol), $Cs_2CO_3$ (932 mg, 2.86 mmol) and dioxane (10 ml) were charged into a vial under argon. The vial was sealed and the reaction mixture was stirred at 100° C. for 16 h. Subsequently, the reaction mixture was cooled to room temperature, diluted with EtOAc and washed with water (2×) and brine. The organic layers were dried over $Na_2SO_4$, filtered and concentrated under vacuum. The residue was triturated with EtOAc and the solid was collected by filtration, washed with EtOAc and dried under vacuum to obtain the title compound as a light orange solid. (UPLC-MS 5) $t_R$ 2.78 min; ESI-MS 345.3 $[M+H]^+$.

Intermediate 3: Ethyl 6-(2-aminophenyl)picolinate

A solution of ethyl 6-(2-((tert-butoxycarbonyl)amino)phenyl)picolinate (Intermediate 4, 685 mg, 2.00 mmol) in DCM (10 ml) was treated with TFA (3 ml). The solution was stirred at room temperature for 2 h and then concentrated under vacuum. The residue was dissolved in DCM and washed with aq. sat. $NaHCO_3$ (2×) and water. The organic layers were dried over $Na_2SO_4$, filtered and concentrated under vacuum to obtain the title compound as a beige solid. (UPLC-MS 1) $t_R$ 1.00 min; ESI-MS 243.4 $[M+H]^+$.

Intermediate 4: Ethyl 6-(2-((tert-butoxycarbonyl)amino)phenyl)picolinate 6-(2-((tert-butoxycarbonyl)amino)phenyl)picolinic acid (Intermediate 5, 837 mg, 2.66 mmol), HATU (1215 mg, 3.20 mmol), N-methylmorpholine (0.878 ml, 7.99 mmol) and EtOH (1 ml, 17.1 mmol) were dissolved in DMF (15 ml). The reaction solution was stirred at room temperature for 2 h, diluted in EtOAc and washed with sat. aq. $NaHCO_3$ and brine. The organic layer was dried over $Na_2SO_4$, filtered and concentrated under vacuum. The crude material was purified by normal phase chromatography (24 g silica gel cartridge, heptanes/EtOAc 100:0 to 65:35) to give the title compound as a colorless oil. (UPLC-MS 1) $t_R$ 1.30 min; ESI-MS 343.2 $[M+H]^+$.

Intermediate 5: 6-(2-((tert-butoxycarbonyl)amino)phenyl)picolinic acid

A vial was charged with ethyl 6-bromopicolinate (700 mg, 3.04 mmol), tert-butyl 2-(4,4,5,5-tetramethyl-1,3,2-dioxaborolan-2-yl)phenylcarbamate (1165 mg, 3.65 mmol), $PdCl_2(PPh_3)_2$ (214 mg, 0.304 mmol), capped, flushed with argon and then DME (20 ml) and $Na_2CO_3$ (2 M in water, 4.56 ml, 9.13 mmol) were added. The mixture was stirred at 100° C. for 16 h. The reaction mixture was cooled to room temperature, extracted with sat. aq. $NaHCO_3$ (3×). The combined aq. layers were then acidified with HCl (8M in water) to pH 5. The precipitate was collected by filtration to obtain the title compound as an off white solid. (UPLC-MS 1) $t_R$ 0.99 min; ESI-MS 313.1 $[M-H^+]^-$.

Intermediate 6: 1-(6-(1,3-dioxolan-2-yl)pyridin-2-yl)-3-(5-cyano-4-((2-methoxyethyl)amino)pyridin-2-yl)-1-methylurea Phenyl (6-(1,3-dioxolan-2-yl)pyridin-2-yl)(methyl)carbamate (Intermediate 7, 49 mg, 0.163 mmol) and 6-amino-4-((2-methoxyethyl)amino)nicotinonitrile (intermediate 8, 34.5 mg, 0.179 mmol) were dissolved in THF (1 ml) under argon. The solution was cooled to −78° C. and treated slowly with LHMDS (1M in THF, 0.359 ml, 0.359 mmol). The reaction mixture was stirred at −78° C. for 1 h and then slowly warmed up to 0° C. and stirred at 0° C. for 30 minutes. The reaction mixture was poured into sat. aq.

NH$_4$Cl and extracted twice with DCM. The combined organic phases were then dried over Na$_2$SO$_4$, filtered and concentrated. The crude material was purified by normal phase chromatography (4 g silica gel cartridge, heptanes/EtOAc 100:0 to 0:100) to give the title compound as a white solid. (UPLC-MS 3) t$_R$ 0.92 min; ESI-MS 399.2 [M+H]$^+$.

Intermediate 7: phenyl (6-(1,3-dioxolan-2-yl)pyridin-2-yl)(methyl)carbamate

A solution of 6-(1,3-dioxolan-2-yl)-N-methylpyridin-2-amine (Intermediate 9, 45 mg, 0.250 mmol) and diphenylcarbonate (107 mg, 0.499 mmol) in THF (1.5 ml) at −10° C. was treated with LiHMDS (1M in THF, 0.350 ml, 0.350 mmol) and stirred for 0.5 h. Then, LiHMDS (1M in THF, 0.350 ml, 0.350 mmol) was added, the reaction was warmed up to room temperature and stirred for 1.5 h. The reaction mixture was quenched with sat. aq. NH$_4$Cl, extracted with EtOAc (2×). The combined organic layers were washed with brine, dried over Na$_2$SO$_4$, filtered and concentrated under reduced pressure. The crude material was purified by normal phase chromatography (4 g silica gel cartridge, heptanes/EtOAc 100:0 to 0:100) to give the title compound as a pale yellow solid. (UPLC-MS 5) t$_R$ 1.92 min; ESI-MS 301.1 [M+H]$^+$.

Intermediate 8: 6-amino-4-((2-methoxyethyl)amino)nicotinonitrile

A solution of 6-amino-4-fluoronicotinonitrile (intermediate 10, 1.10 g, 8.02 mmol) in DMA (20 ml) was treated with 2-methoxyethylamine (2.07 ml, 24.1 mmol) and DIPEA (4.20 mL, 24.1 mmol), heated to 50° C. and stirred for 15 h. The reaction mixture was cooled to room temperature and concentrated. The crude material was purified by normal phase chromatography (24 g silica gel cartridge, heptanes/EtOAc 100:0 to 0:100). The product containing fractions were concentrated and dried under vacuum to give the title compound as an off-white solid. $^1$H NMR (400 MHz, DMSO-d$_6$) δ 7.92 (s, 1H), 6.39 (s, 2H), 6.15 (t, 1H), 5.61 (s, 1H), 3.46 (t, 2H), 3.27 (s, 3H), 3.24 (q, 2H). (UPLC-MS 3) t$_R$ 0.62; ESI-MS 193.1 [M+H]$^+$.

Intermediate 9: 6-(1,3-dioxolan-2-yl)-N-methylpyridin-2-amine

A vial was charged with 2-bromo-6-(1,3-dioxolan-2-yl)pyridine (200 mg, 0.869 mmol), methylamine (2M in THF, 0.87 ml, 1.7 mmol), chloro[2-(dicyclohexylphosphino)-3,6-dimethoxy-2',4', 6'-triisopropyl-1,1'-biphenyl][2-(2-aminoethyl)phenyl]palladium(II) (34.7 mg, 0.043 mmol) and K$_2$CO$_3$ (1133 mg, 3.48 mmol), flushed with argon and then charged with tert-BuOH (4 ml), capped, heated to 110° C. and the mixture stirred for 2 h. The reaction mixture was cooled to room temperature, diluted with water and extracted with EtOAc (2×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 45:55) to give the title compound as a light brown oil. (UPLC-MS 3) t$_R$ 0.36 min; ESI-MS 181.1 [M+H]$^+$.

Intermediate 10: 6-amino-4-fluoronicotinonitrile

4-Fluoro-5-iodopyridin-2-amine (Intermediate 11, 240 g, 1 mol), zinc cyanide (125 g, 1.05 mol), zinc (13 g, 0.2 mol), Pd$_2$(dba)$_3$ (25 g, 25 mmol) and dppf (55 g, 0.1 mol) in DMA (800 ml) were degassed and charged into the round bottom flask under nitrogen. The mixture was stirred at 100° C. for 3 h. The reaction mixture was diluted with 5% NaHCO$_3$ (2 l), extracted with EtOAc (4×600 ml). The combined organic layers were washed with 5% NaOH (1 l1), dried over Na$_2$SO$_4$, concentrated to 700 ml. The resulting organic phase was eluted through silica gel column with EtOAc (1.7 l). The combined organic filtrate was washed with 2 M HCl (3×800 ml). The pH of the aqueous phase was adjusted to 10 with saturated NaHCO$_3$. The aqueous phase was extracted whit DCM (3×500 ml). The combined DCM was dried over Na$_2$SO$_4$ and concentrated. The residue was further purified by column chromatography (eluted with pentane: EtOAc 10:1 to 3:2) followed by recrystallization from pentane/EtOAc 3/1 to give the title compound as white solid. $^1$H NMR (400 MHz, DMSO-d$_6$) δ 8.40 (d, 1H), 7.40 (s, 2H), 6.34 (d, 1H).

Intermediate 11: 4-fluoro-5-iodopyridin-2-amine

A suspension of 4-fluoropyridin-2-amine (336 g, 2.5 mol) and NIS (745 g, 2.75 mol) in MeCN (9 l) was treated with TFA (114 g, 1 mol). The reaction mixture was then stirred at room temperature for 8 h. The reaction mixture was diluted with EtOAc (10 l), washed with sat. Na$_2$S$_2$O$_3$ (2×5 l), brine (4×5 l). The combined organic layers were dried over Na$_2$SO$_4$, filtered and concentrated to get the crude product. The crude product was purified by recrystallization from EtOAc/pentane (1/10) to afford the title compound as a white solid. $^1$H NMR (400 MHz, DMSO-d$_6$) δ 8.14 (d, 1H), 6.45 (s, 2H), 6.33 (d, 1H).

Intermediate 12: 1-(6-(1,3-dioxolan-2-yl)pyridin-2-yl)-3-(5-cyano-4-((2-methoxyethyl)amino)pyridin-2-yl)-1-(2-methoxyethyl)urea The title compound was prepared by a method similar to that of Intermediate 6 by replacing phenyl (6-(1,3-dioxolan-2-yl)pyridin-2-yl)(methyl)carbamate (Intermediate 7) with phenyl (6-(1,3-dioxolan-2-yl)pyridin-2-yl)(2-methoxyethyl)carbamate (Intermediate 13). (UPLC-MS 3) t$_R$ 0.95 min; ESI-MS 443.2 [M+H]$^+$.

Intermediate 13: phenyl (6-(1,3-dioxolan-2-yl)pyridin-2-yl)(2-methoxyethyl)carbamate The title compound was prepared by a method similar to that of Intermediate 7 by replacing 6-(1,3-dioxolan-2-yl)-N-methylpyridin-2-amine (Intermediate 9) with 6-(1,3-dioxolan-2-yl)-N-(2-methoxyethyl)pyridin-2-amine (Intermediate 14). (UPLC-MS 5) t$_R$ 1.91 min; ESI-MS 345.2 [M+H]$^+$.

Intermediate 14: 6-(1,3-dioxolan-2-yl)-N-(2-methoxyethyl)pyridin-2-amine

A mixture of 2-bromo-6-(1,3-dioxolan-2-yl)pyridine (210 mg, 0.913 mmol) and 2-methoxyethanamine (1 ml, 11.6 mmol) was heated at 90° C. for 16 h. The reaction mixture was cooled to room temperature and partitioned between water and EtOAc. The aq. layer was extracted with EtOAc (2×). The combined organic layers were dried over Na$_2$SO$_4$, filtered and concentrated under vacuum. The crude material was purified by normal phase chromatography (12 g silica gel cartridge, heptanes/EtOAc 100:0 to 40:60) to give the title compound as a yellow oil. (UPLC-MS 3) t$_R$ 0.47 min; ESI-MS 225.2 [M+H]$^+$.

Intermediate 15: (racemic) 1-(6-(1,3-dioxolan-2-yl) pyridin-2-yl)-3-(5-cyano-4-((2-methoxyethyl)amino) pyridin-2-yl)-1-((tetrahydrofuran-3-yl)methyl)urea (racemic) phenyl (6-(1,3-dioxolan-2-yl)pyridin-2-yl)((tetrahydrofuran-3-yl)methyl)carbamate (Intermediate 16, 43.8 mg, 0.118 mmol) and 6-amino-4-((2-methoxyethyl)amino) nicotinonitrile (Intermediate 8, 25 mg, 0.130 mmol) were dissolved in THF (1 ml) under argon. The solution was cooled to −78° C. and treated slowly with LiHMDS (1M in THF, 0.260 ml, 0.260 mmol). The reaction mixture was stirred at −78° C. for 1 h, then slowly warmed up to −20° C. for 2.5 h and then warmed up to room temperature for 30 minutes. The reaction mixture was poured into sat. aq. NH$_4$Cl and extracted twice with DCM. The combined organic phases were then dried over Na$_2$SO$_4$, filtered and evaporated. The crude material was purified by normal phase chromatography (4 g silica gel cartridge, heptanes/EtOAc 100:0 to 0:100) to give the title compound as a white solid. (UPLC-MS 3) $t_R$ 0.92 min; ESI-MS 469.2 [M+H]$^+$.

Intermediate 16: (racemic) phenyl (6-(1,3-dioxolan-2-yl)pyridin-2-yl)((tetrahydrofuran-3-yl)methyl) carbamate A solution of (racemic) 6-(1,3-dioxolan-2-yl)-N-((tetrahydrofuran-3-yl)methyl)pyridin-2-amine (Intermediate 17, 160 mg, 0.639 mmol) and diphenylcarbonate (274 mg, 1.28 mmol) in THF (4 ml) at −78° C. was treated with LiHMDS (1M in THF, 0.895 ml, 0.895 mmol) and stirred for 30 minutes. The reaction mixture was quenched at −78° C. with sat. aq. NH$_4$Cl. The resulting mixture was then warmed up to room temperature and then partitioned between DCM and water. The aq. layer was washed twice with DCM. The combined org. layers were dried over Na$_2$SO$_4$, filtered and concentrated under vacuum. The crude material was purified by normal phase chromatography (12 g silica gel cartridge, heptanes/EtOAc 100:0 to 40:60) to give the title compound as a colorless oil. (UPLC-MS 3) $t_R$ 1.00 min; ESI-MS 370.9 [M+H]$^+$.

Intermediate 17: (racemic) 6-(1,3-dioxolan-2-yl)-N-((tetrahydrofuran-3-yl)methyl)pyridin-2-amine A septum sealed vial was charged with 2-bromo-6-(1,3-dioxolan-2-yl)pyridine (200 mg, 0.869 mmol), (racemic) (tetrahydrofuran-3-yl)methanamine (176 mg, 1.74 mmol), chloro[2-(dicyclohexylphosphino)-3,6-dimethoxy-2',4',6'-triisopropyl-1,1'-biphenyl][2-(2-aminoethyl)-phenyl]palladium(II) (34.7 mg, 0.043 mmol) and K$_2$CO$_3$ (1.13 g, 3.48 mmol), flushed with argon and then charged with tert-BuOH (4 ml), capped, heated to 110° C. and stirred for 2 h. The reaction mixture was cooled to room temperature, diluted with water and extracted with EtOAc (2×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 26:74) to give the title compound as a light brown oil. $^1$H NMR (400 MHz, DMSO-d$_6$) δ 7.38 (dd, 1H), 6.67 (t, 1H), 6.59 (d, 1H), 6.44 (dd, 1H), 5.50 (s, 1H), 4.07-3.99 (m, 2H), 3.97-3.90 (m, 2H), 3.77-3.67 (m, 2H), 3.65-3.58 (m, 1H), 3.44 (dd, 1H), 3.26-3.12 (m, 2H), 2.48-2.42 (m, 1H), 2.00-1.90 (m, 1H), 1.64-1.53 (m, 1H).

Intermediate 18: (racemic) 1-(5-(((tert-butyldimethylsilyl)oxy)methyl)-6-(1,3-dioxolan-2-yl)pyridin-2-yl)-3-(5-cyano-4-((2-methoxyethyl)amino)pyridin-2-yl)-1-((tetrahydrofuran-3-yl)methyl)urea A solution of LiHMDS in THF (0.9 M, 1.21 ml, 1.09 mmol) was added to phenyl (5-(((tert-butyldimethylsilyl) oxy)methyl)-6-(1,3-dioxolan-2-yl)pyridin-2-yl)((tetrahydrofuran-3-yl)methyl)carbamate (Intermediate 19, 280 mg, 0.54 mmol) and 6-amino-4-((2-methoxyethyl)amino)nicotinonitrile (intermediate 8, 115 mg, 0.60 mmol) in THF (5 ml) cooled at −78° C. with a dry ice/acetone bath. After stirring for 20 minutes at −78 OC additional LiHMDS in THF (1.8 ml) was added, stirring continued for 20 minutes, the rection warmed to room temperature, aqueous NH$_4$Cl was added and the mixture extracted with EtOAc. The organic layers were washed with brine, dried over Na$_2$SO$_4$ and evaporated. The residue was then purified by normal phase chromatography using a 40 g RediSep® column, eluting with a gradient from heptane to 50% EtOAc in heptane. Product containing fractions were then combined and evaporated to give the title compound. (UPLC-MS 7) $t_R$ 1.45 min; ESI-MS 613.5 [M+H]$^+$.

Intermediate 19: (racemic) phenyl (5-(((tert-butyldimethylsilyl)oxy)methyl)-6-(1,3-dioxolan-2-yl) pyridin-2-yl) ((tetrahydrofuran-3-yl)methyl)carbamate A solution of LiHMDS in THF (0.9 M, 1.02 ml, 0.835 mmol) was added to (racemic) 5-(((tert-butyldimethylsilyl) oxy)methyl)-6-(1,3-dioxolan-2-yl)-N-((tetrahydrofuran-3-yl)methyl)pyridin-2-amine (Intermediate 20, 366 mg, 0.918 mmol) and diphenyl carbonate (197 mg, 0.918 mmol) in THF (10 ml) cooled at −78 OC with a dry ice/acetone bath. After stirring for 30 minutes at −78 OC additional diphenyl carbamate (90 mg, 0.420 mmol) was added and the reaction mixture allowed to warm to room temperature. Aqueous NH$_4$Cl was then added and extracted with EtOAc. The organic layer was washed with brine, dried over Na$_2$SO$_4$ and evaporated. The residue was then purified by normal phase chromatography using a 40 g RediSep® column, eluting with a gradient from heptane to 50% EtOAc in heptane. Product containing fractions were then combined and evaporated to give the title compound. (UPLC-MS 6) $t_R$ 1.49 min; ESI-MS 515.4 [M+H]$^+$.

Intermediate 20: (racemic) 5-(((tert-butyldimethylsilyl)oxy)methyl)-6-(1,3-dioxolan-2-yl)-N-((tetrahydrofuran-3-yl)methyl) pyridin-2-amine Diisopropylethylamine (0.22 ml, 1.26 mmol), tert-butyldimethylsilyl chloride (164 mg, 1.09 mmol) and DMAP (5 mg, 0.042 mmol) were added consecutively to (racemic) (2-(1,3-dioxolan-2-yl)-6-(((tetrahydrofuran-3-yl)methyl) amino)pyridin-3-yl)methanol (Intermediate 21, 235 mg, 0.838 mmol) in DCM (5 ml) at room temperature. After stirring for 18 h additional tert-butyldimethylsilyl chloride (50 mg, 0.332 mmol) was added and stirring continued for 1 h. The reaction mixture was then partitioned between saturated aqueous NaHCO$_3$ and DCM, extracted 2× with DCM, the organic layers dried over Na$_2$SO$_4$ and evaporated to give the title compound as a yellow oil. (UPLC-MS 7) $t_R$ 1.22 min; ESI-MS 395.2 [M+H]$^+$.

Intermediate 21: (racemic) (2-(1,3-dioxolan-2-yl)-6-(((tetrahydrofuran-3-yl)methyl)amino)pyridin-3-yl) methanol Sodium borohydride (39 mg, 1.02 mmol) was added to a solution of (racemic) 2-(1,3-dioxolan-2-yl)-6-(((tetrahydrofuran-3-yl)methyl)amino)nicotinaldehyde (Intermediate 22, 370 mg, 0.931 mmol) in EtOH (10 ml) cooled to 0° C. with an ice bath. The reaction mixture was stirred for 1 h at room temperature, then partitioned between saturated aqueous NaHCO$_3$ and EtOAc, extracted 3× with EtOAc, the organic layers dried over Na$_2$SO$_4$ and evaporated. The residue was purified by normal phase chromatography using a 24 g RediSep® column, eluting with a gradient from heptane to 50% EtOAc in heptane. Product containing fractions were then combined and evaporated to give the title compound as a colourless oil. (UPLC-MS 6) t$_R$ 0.40 min; ESI-MS 281.2 [M+H]$^+$.

Intermediate 22: (racemic) 2-(1,3-dioxolan-2-yl)-6-(((tetrahydrofuran-3-yl)methyl)amino) nicotinaldehyde A solution of MeLi in Et$_2$O (1.6 M, 0.90 ml, 1.44 mmol) was added to a solution of (racemic) 5-bromo-6-(1,3-dioxolan-2-yl)-N-((tetrahydrofuran-3-yl)methyl)pyridin-2-amine (Intermediate 23, 430 mg, 1.31 mmol) in THF (15 ml) cooled to −78° C. with a dry-ice/acetone bath. After stirring for 5 minutes at −78° C. a solution of nBuLi in hexanes (1.6 M, 0.90 ml, 0.90 mmol) was added dropwise. After a further 20 minutes DMF (1.01 ml, 13.1 mmol) was added, the reaction mixture stirred at −78° C. for 1 h then warmed to room temperature. Aqueous NH$_4$Cl was added, the mixture extracted with DCM, the organic layers dried over Na$_2$SO$_4$ and evaporated to give the title compound. (UPLC-MS 6) t$_R$ 0.66 min; ESI-MS 279.2 [M+H]$^+$.

Intermediate 23: (racemic) 5-bromo-6-(1,3-dioxolan-2-yl)-N-((tetrahydrofuran-3-yl)methyl)pyridin-2-amine A mixture of 3,6-dibromo-2-(1,3-dioxolan-2-yl)pyridine (Intermediate 32, 104 mg, 0.337 mmol), (tetrahydrofuran-3-yl)methanamine (51 mg, 0.505 mmol), CuI (3.2 mg, 0.017 mmol) and K$_2$CO$_3$ (47 mg, 0.337 mmol) was heated in a septum sealed vial at 90° C. for 1 h and then at 110° C. for 1 h. The cooled reaction mixture was partitioned between water and DCM, extracted 2× with DCM, the combined organic layers washed with brine and evaporated. The residue was then purified by normal phase chromatography using a 4 g RediSep® column, eluting with a gradient from heptane to EtOAc. Product containing fractions were combined and evaporated to give the title compound as a yellow oil. (UPLC-MS 6) t$_R$ 0.86 min; ESI-MS 329.1 and 331.1 [M+H]$^+$.

Intermediates 24 and 25: (S) 1-(6-(1,3-dioxolan-2-yl)pyridin-2-yl)-3-(5-cyano-4-((2-methoxyethyl)amino)pyridin-2-yl)-1-((tetrahydrofuran-3-yl)methyl)urea and (R) 1-(6-(1,3-dioxolan-2-yl)pyridin-2-yl)-3-(5-cyano-4-((2-methoxyethyl)amino)pyridin-2-yl)-1-((tetrahydrofuran-3-yl)methyl)urea Racemic 1-(6-(1,3-dioxolan-2-yl)pyridin-2-yl)-3-(5-cyano-4-((2-methoxyethyl)amino)-pyridin-2-yl)-1-((tetrahydrofuran-3-yl)methyl)urea (Intermediate 15, 275 mg, 0.587 mmol) was purified by chiral HPLC: VWR LAPREP P110+loop+P314 instrument; Chiracel Oz/20 μM 5×42 cm column; 70:30 heptane/EtOH mobile phase; 80 ml/min flow rate; 6 ml injection volume (EtOH/DCM); UV 280 nm detection. Product containing fractions were combined and evaporated to give a first eluting peak with a 30.0 minute retention time and a second eluting peak with a 61.5 minute retention time.

Intermediate 26: 1-(6-(1,3-dioxolan-2-yl)-5-(4-methylpiperazine-1-carbonyl)pyridin-2-yl)-3-(5-cyano-4-isopropoxypyridin-2-yl)-1-methylurea A solution of LiHMDS in THF (0.40 ml, 0.361 mmol) was added to a mixture of phenyl (6-(1,3-dioxolan-2-yl)-5-(4-methylpiperazine-1-carbonyl)pyridin-2-yl)(methyl)carbamate (intermediate 27, 70 mg, 0.181 mmol) and 6-amino-4-isopropoxynicotinonitrile (intermediate 28, 32.0 mg, 0.181 mmol) in THF (5 ml) cooled to −78° C. with a dry-ice acetone bath. The reaction mixture was stirred for 2 h at −78° C., warmed to room temperature and stirred for a further 2 h. Saturated aqueous NaHCO$_3$ and DCM were added, the mixture extracted 3× with DCM, the organic layers dried over Na$_2$SO$_4$ and evaporated. The residue was absorbed onto isolute HM-N Sorbent® and purified by normal phase chromatography using a 12 g RediSep® column, eluting with a gradient from heptane to EtOAc and then from DCM to 10% MeOH in DCM. Product containing fractions were then combined and evaporated to give the title compound. (UPLC-MS 7) t$_R$ 0.76 min; ESI-MS 510.4 [M+H]$^+$.

Intermediate 27: phenyl (6-(1,3-dioxolan-2-yl)-5-(4-methylpiperazine-1-carbonyl)pyridin-2-yl)(methyl) carbamate A solution of LiHMDS (1.34 ml, 1.21 mmol) was added dropwise to a mixture of (2-(1,3-dioxolan-2-yl)-6-(methylamino)pyridin-3-yl)(4-methylpiperazin-1-yl)methanone (Intermediate 29, 185 mg, 0.60 mmol), diphenyl carbonate (259 mg, 1.21 mmol) and THF (7 ml) cooled with a dry-ice/acetone bath. The reaction mixture was stirred for 1 h at −78° C., warmed to room temperature, then stirred for 1 h at room temperature, before the addition of aqueous NH$_4$Cl solution. The aqueous layer was extracted 3× with DCM, dried over Na$_2$SO$_3$ and evaporated. Purification of the crude product by normal phase chromatography, 24 g RediSep® column, eluting with a gradient from hexane to EtOAc, then DCM to 10% MeOH in DCM gave the title compound. (UPLC-MS 6) t$_R$ 0.64 min; ESI-MS 427.2 [M+H]$^+$.

Intermediate 28: 6-amino-4-isopropoxynicotinonitrile

A solution of KHMDS (87 g, 438 mmol) was added portionwise to a solution of propan-2-ol (26.3 g, 438 mmol) in THF (250 ml) at room temperature. After 15 min a solution of 6-amino-4-fluoronicotinonitrile (Intermediate 10, 30 g, 219 mmol) in THF (200 ml) was added and the reaction mixture stirred for 18 h at room temperature. The reaction mixture was partitioned between saturated aqueous NH$_4$Cl and EtOAc, extracted with EtOAc (2×), the combined EtOAc layers were dried over Na$_2$SO$_4$ and evaporated. The residue was triturated with Et$_2$O and the product obtained by filtration as a yellow solid. $^1$H NMR (400 MHz, DMSO-d$_6$) δ 8.12 (s, 1H), 6.82 (s, 2H), 6.07 (s, 1H), 4.64 (septet, 1H), 1.31 (d, 6H). (UPLC-MS 7) t$_R$ 0.61; ESI-MS 178.1 [M+H]$^+$.

Intermediate 29: (2-(1,3-dioxolan-2-yl)-6-(methylamino)pyridin-3-yl)(4-methylpiperazin-1-yl)methanone HATU (265 mg, 0.696 mmol) and Et$_3$N (0.297 ml, 2.14 mmol) were added to 2-(1,3-dioxolan-2-yl)-6-(methylamino)nicotinic acid sodium salt (Intermediate 30, 1.0 g, 0.535 mmol) in DMF (3 ml) at room temperature, followed by 1-methylpiperazine (0.214 g, 2.14 mmol). The reaction mixture was stirred for 1 h then partitioned between water and EtOAc, extracted 2× with EtOAc, 2× with DCM, 2× with nBuOH, the combined organic layers dried over $Na_2SO_4$ and evaporated. The residue was triturated with DCM, filtered and evaporated to give the title compound. (UPLC-MS 6) $t_R$ 0.29; ESI-MS 307.2 $[M+H]^+$.

Intermediate 30:
2-(1,3-dioxolan-2-yl)-6-(methylamino)nicotinic acid sodium salt A solution of nBuLi in hexanes (1.6 M, 3.45 ml, 5.52 mmol) was added to a stirred solution of 5-bromo-6-(1,3-dioxolan-2-yl)-N-methylpyridin-2-amine (Intermediate 31, 650 mg, 2.51 mmol) in THF (10 ml) cooled with a dry-ice/acetone bath. The reaction mixture was stirred for 15 min at −78° C., then $CO_2$ bubbled through the solution for 10 seconds. Stirring was continued for 10 minutes at −78° C. and the reaction mixture partitioned between water and $Et_2O$. The aqueous layer was acidified then washed with DCM, then basified with $NaHCO_3$ and washed with DCM, evaporated and the solid triturated with MeOH. Filtration and evaporation of the MeOH gave the title compound. (UPLC-MS 6) $t_R$ 0.32; ESI-MS 225.1 $[M+H]^+$.

Intermediate 31: 5-bromo-6-(1,3-dioxolan-2-yl)-N-methylpyridin-2-amine

A mixture of 3,6-dibromo-2-(1,3-dioxolan-2-yl)pyridine (Intermediate 32, 950 mg, 3.07 mmol), methylamine in EtOH (33%, 1.48 ml, 9.22 mmol) and EtOH (4 ml) was heated in a septum sealed vial for 18 h at 110° C. After cooling, additional methylamine in EtOH (2.96 ml, 18.4 mmol) was added and heating continued for 20 h at 120° C. The cooled reaction mixture was partitioned between water and EtOAc, extracted 2× with EtOAc, dried over $Na_2SO_4$ and evaporated. Purification of the crude product by normal phase chromatography, 40 g RediSep® column, eluting with a gradient from heptane to EtOAc, gave the title compound as a yellow solid. (UPLC-MS 6) $t_R$ 0.77 min; ESI-MS 259.1 and 261.1 $[M+H]^+$.

Intermediate 32:
3,6-dibromo-2-(1,3-dioxolan-2-yl)pyridine

A mixture of 3,6-dibromopicolinaldehyde [1215183-85-9] (365 g, 1.378 mol), ethylene glycol (98 ml, 1.764 mol) and para-toluenesulfonic acid monohydrate (26.8 g, 141 mmol) in toluene (5 ml) was heated to reflux with the separated $H_2O$ being collected with a Dean-Stark trap. After 4 h, the reaction mixture was cooled to room temperature, poured into sat. aq. $NaHCO_3$ and extracted with EtOAc (2×). The combined organic layers were dried over $Na_2SO_4$ and evaporated to afford the crude title compound as a beige solid. (UPLC-MS 3) $t_R$ 0.91; ESI-MS 307.9/309.9/311.9 $[M+H]^+$.

Intermediate 33: 1-(6-(1,3-dioxolan-2-yl)-5-(4-methylpiperazine-1-carbonyl)pyridin-2-yl)-3-(5-cyano-4-((2-methoxyethyl)amino)pyridin-2-yl)-1-methylurea A solution of LiHMDS in THF (0.40 ml, 0.361 mmol) was added to a mixture of phenyl (6-(1,3-dioxolan-2-yl)-5-(4-methylpiperazine-1-carbonyl)pyridin-2-yl)(methyl)carbamate (Intermediate 27, 70 mg, 0.164 mmol) and 6-amino-4-((2-methoxyethyl)amino)nicotinonitrile (Intermediate 8, 35 mg, 0.181 mmol) in THF (5 ml) cooled to −78° C. with a dry-ice acetone bath. The reaction mixture was stirred for 2 h at −78° C., warmed to room temperature and stirred for a further 2 h. Saturated aqueous $NaHCO_3$ and DCM were added, the mixture extracted 3× with DCM, the organic layers dried over $Na_2SO_4$ and evaporated. The residue was absorbed onto isolute HM-N Sorbent® and purified by normal phase chromatography using a 12 g RediSep® column, eluting with a gradient from heptane to EtOAc and then from DCM to 10% MeOH in DCM. Product containing fractions were then combined and evaporated to give the title compound. (UPLC-MS 7) $t_R$ 0.59 min; ESI-MS 525.3 $[M+H]^+$.

Intermediate 34: 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea A solution of LiHMDS in THF (0.45 ml, 0.407 mmol) was added to a mixture of phenyl (6-(1,3-dioxolan-2-yl)-5-(1-methyl-1H-pyrazol-4-yl)pyridin-2-yl)(ethyl)carbamate (Intermediate 35, 73 mg, 0.185 mmol) and 6-amino-4-((2-methoxyethyl)amino)nicotinonitrile (Intermediate 8, 39 mg, 0.204 mmol) in THF (3 ml) cooled to −78° C. with a dry-ice acetone bath. The reaction mixture was stirred for 1 h at −78° C. and additional LiHMDS solution added (0.45 ml) and for a further 10 minutes before adding further LiHMDS solution (0.45 ml) The reaction mixture was stirred for 1 h then warmed to room temperature, saturated aqueous $NaHCO_3$ and DCM were added, the mixture extracted 3× with DCM, the organic layers dried over $Na_2SO_4$ and evaporated. The residue was absorbed onto isolute HM-N Sorbent® and purified by normal phase chromatography using a 24 g RediSep® column, eluting with a gradient from heptane to EtOAc. Product containing fractions were then combined and evaporated to give the title compound. (UPLC-MS 7) $t_R$ 0.98 min; ESI-MS 493.3 $[M+H]^+$.

Intermediate 35: phenyl (6-(1,3-dioxolan-2-yl)-5-(1-methyl-1H-pyrazol-4-yl)pyridin-2-yl)(ethyl)carbamate A solution of 6-(1,3-dioxolan-2-yl)-N-ethyl-5-(1-methyl-1H-pyrazol-4-yl)pyridin-2-amine (Intermediate 36, 320 mg, 1.17 mmol) and diphenylcarbonate (275 mg, 1.28 mmol) in THF (10 ml) at −78° C. was treated with LiHMDS (1M in THF, 1.43 ml, 1.28 mmol) and stirred for 2 h. The reaction mixture was then warmed to room temperature and stirred for 2 h, quenched with sat. aq. $NH_4Cl$, extracted with EtOAc (2×), the combined organic layers washed with brine, dried over $Na_2SO_4$, filtered and concentrated. The crude material was purified by normal phase chromatography (40 g RediSep® column, eluting with a gradient of heptanes/EtOAc 100:0 to 0:100) to give the title compound as a white solid. (UPLC-MS 6) $t_R$ 1.06 min; ESI-MS 395.2 $[M+H]^+$.

Intermediate 36: 6-(1,3-dioxolan-2-yl)-N-ethyl-5-(1-methyl-1H-pyrazol-4-yl)pyridin-2-amine A mixture of 5-bromo-6-(1,3-dioxolan-2-yl)-N-ethylpyridin-2-amine (Intermediate 37, 370 mg, 1.36 mmol), 1-methylpyrazole-4-boronic acid pinacol ester (423 mg, 2.03 mmol), PdCl2(dppf).$CH_2Cl_2$ adduct (111 mg, 0.14 mmol), DME (5 ml) and saturated aqueous $Na_2CO_3$ (1.67 ml) were heated for 4 h at 80° C. in a septum sealed vial under an Ar atmosphere. The cooled reaction mixture was partitioned between water and DCM, extracted 2× with DCM and the combined organic layers evaporated onto isolute HM-N Sorbent®. Purification by normal phase chromatography using a 40 g RediSep® column, eluting with a gradient from heptane to EtOAc, gave the title compound. (UPLC-MS 6) $t_R$ 0.52 min; ESI-MS 275.2 [M+H]+.

Intermediate 37: 5-bromo-6-(1,3-dioxolan-2-yl)-N-ethylpyridin-2-amine

The title compound was prepared in an analogous manner to 5-bromo-6-(1,3-dioxolan-2-yl)-N-methylpyridin-2-amine (Intermediate 31), except a solution of ethylamine in THF (2 M) was used in place of the solution of methylamine in EtOH. (UPLC-MS 7) $t_R$ 0.88 min; ESI-MS 273.2 [M+H]+.

Intermediate 38: 1-(6-(1,3-dioxolan-2-yl)-5-(1-methyl-1H-pyrazol-4-yl)pyridin-2-yl)-3-(5-cyano-4-(isopropylamino)pyridin-2-yl)-1-ethylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except 6-amino-4-(isopropylamino)nicotinonitrile (Intermediate 39) was used in place of 6-amino-4-((2-methoxyethyl)amino)nicotinonitrile (Intermediate 8). (UPLC-MS 7) $t_R$ 1.09 min; ESI-MS 477.3 [M+H]+.

Intermediate 39: 6-amino-4-(isopropylamino)nicotinonitrile

A mixture of isopropylamine (1.83 ml, 21.3 mmol), 6-amino-4-fluoronicotinonitrile (Intermediate 10, 972 mg, 7.09 mmol) and diisopropylethylamine (3.71 ml, 21.3 mmol) in DMA (17 ml) was heated at 50° C. in a septum sealed reaction vessel for 48 h. The reaction mixture was then cooled, evaporated and purified by normal phase chromatography using an 40 g RediSep® column, eluting with a gradient from DCM to 10% MeOH in DCM. Product containing fractions were combined and evaporated. The residue was partitioned between DCM and 10% aqueous citric acid solution, the aqueous layer washed 2× with DCM, basified with NaHCO$_3$, extracted with DCM (4×), the combined organic extracts from the basic extraction dried over Na$_2$SO$_4$ and evaporated to give the title compound as a white solid. $^1$H NMR (400 MHz, DMSO-d$_6$) δ 7.89 (s, 1H), 6.31 (s, br, 2H), 5.71 (d, br, 1H), 5.58 (s, 1H), 3.61-3.49 (m, 1H), 1.14 (d, 6H).

Intermediate 40: 1-(6-(1,3-dioxolan-2-yl)-5-(1-methyl-1H-pyrazol-4-yl)pyridin-2-yl)-3-(5-cyano-4-isopropoxypyridin-2-yl)-1-ethylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except 6-amino-4-isopropoxynicotinonitrile (Intermediate 28) was used in place of 6-amino-4-((2-methoxyethyl)amino)nicotinonitrile (Intermediate 8). (UPLC-MS 7) $t_R$ 1.14 min; ESI-MS 478.2 [M+H]+.

Intermediate 41: 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-(1-methyl-1H-pyrazol-4-yl)pyridin-2-yl)(methyl)carbamate (Intermediate 42) was used in place of phenyl (6-(1,3-dioxolan-2-yl)-5-(1-methyl-1H-pyrazol-4-yl)pyridin-2-yl)(ethyl)carbamate (Intermediate 35). (UPLC-MS 6) $t_R$ 0.93 min; ESI-MS 479.3 [M+H]+.

Intermediate 42: phenyl (6-(1,3-dioxolan-2-yl)-5-(1-methyl-1H-pyrazol-4-yl)pyridin-2-yl)(methyl)carbamate The title compound was prepared in an analogous manner to phenyl (6-(1,3-dioxolan-2-yl)-5-(1-methyl-1H-pyrazol-4-yl)pyridin-2-yl)(ethyl)carbamate (Intermediate 35), except 6-(1,3-dioxolan-2-yl)-N-methyl-5-(1-methyl-1H-pyrazol-4-yl)pyridin-2-amine (Intermediate 43) was used in place of 6-(1,3-dioxolan-2-yl)-N-ethyl-5-(1-methyl-1H-pyrazol-4-yl)pyridin-2-amine (Intermediate 36). (UPLC-MS 7) $t_R$ 0.96 min; ESI-MS 381.2 [M+H]+.

Intermediate 43: 6-(1,3-dioxolan-2-yl)-N-methyl-5-(1-methyl-1H-pyrazol-4-yl)pyridin-2-amine The title compound was prepared in an analogous manner to 6-(1,3-dioxolan-2-yl)-N-ethyl-5-(1-methyl-1H-pyrazol-4-yl)pyridin-2-amine (Intermediate 36), except 5-bromo-6-(1,3-dioxolan-2-yl)-N-methylpyridin-2-amine (Intermediate 31) was used in place of 5-bromo-6-(1,3-dioxolan-2-yl)-N-ethylpyridin-2-amine (Intermediate 37). (UPLC-MS 7) $t_R$ 0.44 min; ESI-MS 261.2 [M+H]+.

Intermediate 44: 1-(6-(1,3-dioxolan-2-yl)-5-(1-methyl-1H-pyrazol-4-yl)pyridin-2-yl)-3-(5-cyano-4-(isopropylamino)pyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-(1-methyl-1H-pyrazol-4-yl)pyridin-2-yl)(methyl)carbamate (Intermediate 42) and 6-amino-4-(isopropylamino)nicotinonitrile (Intermediate 39) were used in place of phenyl (6-(1,3-dioxolan-2-yl)-5-(1-methyl-1H-pyrazol-4-yl)pyridin-2-yl)(ethyl)carbamate (Intermediate 35) and 6-amino-4-((2-methoxyethyl)amino)nicotinonitrile (Intermediate 8). (UPLC-MS 6) $t_R$ 1.05 min; ESI-MS 463.3 [M+H]+.

Intermediate 45: N-((6-(3-(5-cyano-4-((2-methoxyethyl)amino)pyridin-2-yl)-1-methylureido)-2-(1,3-dioxolan-2-yl)pyridin-3-yl)methyl)-N-methylacetamide The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-((N-methylacetamido)methyl)pyridin-2-yl)(methyl)carbamate (Intermediate 46) was used in place of phenyl (6-(1,3-dioxolan-2-yl)-5-(1-methyl-1H- pyrazol-4-yl)pyridin-2-yl)(ethyl)carbamate (Intermediate 35). (UPLC-MS 7) $t_R$ 0.83 min; ESI-MS 484.2 [M+H]$^+$.

Intermediate 46: phenyl (6-(1,3-dioxolan-2-yl)-5-((N-methylacetamido)methyl)pyridin-2-yl)(methyl)carbamate The title compound was prepared in an analogous manner to phenyl (5-(((tert-butyldimethylsilyl)oxy)methyl)-6-(1,3-dioxolan-2-yl)pyridin-2-yl)((tetrahydrofuran-3-yl)methyl)carbamate (Intermediate 19), except N-((2-(1,3-dioxolan-2-yl)-6-(methylamino)pyridin-3-yl)methyl)-N-methylacetamide (Intermediate 47) was used in place of 5-((((tert-butyldimethylsilyl)oxy)methyl)-6-(1,3-dioxolan-2-yl)-N-((tetrahydrofuran-3-yl)methyl)pyridin-2-amine (Intermediate 20). (UPLC-MS 7) $t_R$ 0.91 min; ESI-MS 386.2 [M+H]$^+$.

Intermediate 47: N-((2-(1,3-dioxolan-2-yl)-6-(methylamino)pyridin-3-yl)methyl)-N-methylacetamide Acetic anhydride (0.126 ml, 1.31 mmol) was added to a mixture of 6-(1,3-dioxolan-2-yl)-N-methyl-5-((methylamino)methyl)pyridin-2-amine (Intermediate 48, 325 mg, 1.31 mmol), 2,6-lutidine (0.236 ml, 1.97 mmol) and DCM (2 ml) cooled with an ice bath. The reaction mixture was stirred at 0° C. for 30 minutes then for 18 h at room temperature, saturated aqueous NaHCO$_3$ solution was added and the aqueous layer extracted 3× with DCM. The combined organic layers were dried over Na$_2$SO$_4$ and evaporated. Purification by normal phase chromatography using a 12 g RediSep® column, eluting with a gradient from heptane to EtOAc, gave the title compound as a yellow gum. (UPLC-MS 6) $t_R$ 0.40 min; ESI-MS 266.2 [M+H]$^+$.

Intermediate 48: 6-(1,3-dioxolan-2-yl)-N-methyl-5-((methylamino)methyl)pyridin-2-amine A mixture of 2-(1,3-dioxolan-2-yl)-6-(methylamino)nicotinaldehyde (Intermediate 49, 340 mg, 1.47 mmol), methylamine hydrochloride (198 mg, 2.94 mmol), a solution of methylamine in EtOH (8 M, 0.367 ml, 2.94 mmol), sodium cyanoborohydride (369 mg, 5.88 mmol) and MeOH (8 ml) were heated for 3 h at 50° C. in a septum sealed vial. The cooled reaction mixture was partitioned between water and DCM, extracted 2× with DCM, dried over Na$_2$SO$_4$, filtered and evaporated to give the title compound as a yellow foam. (UPLC-MS 6) $t_R$ 0.31 min; ESI-MS 224.2 [M+H]$^+$.

Intermediate 49: 2-(1,3-dioxolan-2-yl)-6-(methylamino)nicotinaldehyde

A solution of nBuLi in hexanes (1.6 M, 3.47 ml, 5.56 mmol) was added to 5-bromo-6-(1,3-dioxolan-2-yl)-N-methylpyridin-2-amine (Intermediate 31, 1.2 g, 4.63 mmol) in THF (50 ml) cooled with a dry-ice/acetone bath. After stirring for 5 minutes at −78° C., additional nBuLi in hexanes (3.47 ml, 5.56 mmol) was added, the reaction mixture stirred for a further 20 minutes at −78° C., then DMF (3.59 ml, 46.3 mmol) was added. Stirring was continued for a further 1 h at −78° C., the reaction mixture warmed to room temperature, quenched with aqueous NH$_4$Cl and extracted 2× with EtOAc. The combined organic layers were dried over Na$_2$SO$_4$, filtered and evaporated. Purification by normal phase chromatography using a 80 g RediSep® column, eluting with a gradient from heptane to EtOAc, gave the title compound. (UPLC-MS 7) $t_R$ 0.55 min; ESI-MS 209.3 [M+H]$^+$.

Intermediate 50: 3-(5-cyano-4-((2-methoxyethyl)amino)pyridin-2-yl)-1-(5-(difluoromethyl)-6-(1,3-dioxolan-2-yl)pyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (5-(difluoromethyl)-6-(1,3-dioxolan-2-yl)pyridin-2-yl)(methyl)carbamate (Intermediate 51) was used in place of phenyl (6-(1,3-dioxolan-2-yl)-5-(1-methyl-1H-pyrazol-4-yl)pyridin-2-yl)(ethyl)carbamate (Intermediate 35). (UPLC-MS 7) $t_R$ 1.04 min; ESI-MS 449.2 [M+H]$^+$.

Intermediate 51: phenyl (5-(difluoromethyl)-6-(1,3-dioxolan-2-yl)pyridin-2-yl)(methyl)carbamate The title compound was prepared in an analogous manner to phenyl (6-(1,3-dioxolan-2-yl)-5-(4-methylpiperazine-1-carbonyl)pyridin-2-yl)(methyl)carbamate (Intermediate 27), except 5-(difluoromethyl)-6-(1,3-dioxolan-2-yl)-N-methylpyridin-2-amine (Intermediate 52) was used in place of (2-(1,3-dioxolan-2-yl)-6-(methylamino)pyridin-3-yl)(4-methylpiperazin-1-yl)methanone (Intermediate 29). (UPLC-MS 7) $t_R$ 1.15 min; ESI-MS 351.1 [M+H]$^+$.

Intermediate 52: 5-(difluoromethyl)-6-(1,3-dioxolan-2-yl)-N-methylpyridin-2-amine DAST (0.60 ml, 4.11 mmol) was added to a solution of 2-(1,3-dioxolan-2-yl)-6-(methylamino)nicotinaldehyde (Intermediate 49, 340 mg, 1.47 mmol) in DCM (6 ml) cooled with an ice bath. The reaction was warmed to room temperature, stirred for 18 h, then partitioned between saturated aqueous NaHCO$_3$ and DCM and extracted 2× with DCM. The combined organic layers were dried over Na$_2$SO$_4$, filtered and evaporated. Purification by normal phase chromatography using a 12 g RediSep® column, eluting with a gradient from heptane to EtOAc, gave the title compound as a white solid. (UPLC-MS 6) $t_R$ 0.75 min; ESI-MS 231.1 [M+H]$^+$.

Intermediate 53: 1-(6-(1,3-dioxolan-2-yl)-5-((4-methylpiperazin-1-yl)methyl)pyridin-2-yl)-3-(5-cyano-4-isopropoxypyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-((4-methylpiperazin-1-yl)methyl)pyridin-2-yl)(methyl)carbamate (Intermediate 54) and 6-amino-4-isopropoxynicotinonitrile (Intermediate 28) were used in place of phenyl (6-(1,3-dioxolan-2-yl)-5-(1-methyl-1H-pyrazol-4-yl)pyridin-2-yl)(ethyl)carbamate (Intermediate 35) and 6-amino-4-((2-methoxyethyl)amino)nicotinonitrile (Intermediate 8). (UPLC-MS 6) $t_R$ 0.80 min; ESI-MS 496.4 [M+H]$^+$.

Intermediate 54: phenyl (6-(1,3-dioxolan-2-yl)-5-((4-methylpiperazin-1-yl)methyl)pyridin-2-yl)(methyl)carbamate The title compound was prepared in an analogous manner to phenyl (6-(1,3-dioxolan-2-yl)-5-(4-methylpiperazine-1- carbonyl)pyridin-2-yl)(methyl)carbamate (Intermediate 27), except 6-(1,3-dioxolan-2-yl)-N-methyl-5-((4-methylpiperazin-1-yl)methyl)pyridin-2-amine (Intermediate 55) was used in place of (2-(1,3-dioxolan-2-yl)-6-(methylamino) pyridin-3-yl) (4-methylpiperazin-1-yl)methanone (Intermediate 29). (UPLC-MS 6) $t_R$ 0.70 min; ESI-MS 413.3 [M+H]$^+$.

Intermediate 55: 6-(1,3-dioxolan-2-yl)-N-methyl-5-((4-methylpiperazin-1-yl)methyl)pyridin-2-amine NaBH(OAc)$_3$ (458 mg, 2.16 mmol) was added to a solution of 2-(1,3-dioxolan-2-yl)-6-(methylamino)nicotinaldehyde (Intermediate 49, 300 mg, 1.44 mmol) and 1-methylpiperazine (0.168 ml, 1.51 mmol) in 1,2-dichloroethane (10 ml) at room temperature. The reaction mixture was stirred for 18 h, then partitioned between saturated NaHCO$_3$ and DCM, extracted 2× with DCM, dried over Na$_2$SO$_4$ and evaporated to give the title compound as a yellow oil. (UPLC-MS 8) $t_R$ 0.54 min; ESI-MS 293.3 [M+H]$^+$.

Intermediate 56: 3-(5-cyano-4-isopropoxypyridin-2-yl)-1-(5-(difluoromethyl)-6-(1,3-dioxolan-2-yl)pyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (5-(difluoromethyl)-6-(1,3-dioxolan-2-yl)pyridin-2-yl) (methyl)carbamate (Intermediate 51) and 6-amino-4-isopropoxynicotinonitrile (Intermediate 28) were used in place of phenyl (6-(1,3-dioxolan-2-yl)-5-(1-methyl-1H-pyrazol-4-yl)pyridin-2-yl)(ethyl)carbamate (Intermediate 35) and 6-amino-4-((2-methoxyethyl)amino)nicotinonitrile (Intermediate 8). (UPLC-MS 7) $t_R$ 1.19 min; ESI-MS 434.2 [M+H]$^+$.

Intermediate 57: 1-(6-(1,3-dioxolan-2-yl)-5-((2-oxopyrrolidin-1-yl)methyl)pyridin-2-yl)-3-(5-cyanopyridin-2-yl)-1-methylurea A mixture of 1-((2-(1,3-dioxolan-2-yl)-6-(methylamino)pyridin-3-yl)methyl)pyrrolidin-2-one (Intermediate 58, 42 mg, 0.091 mmol), phenyl (5-cyanopyridin-2-yl)carbamate (Intermediate 59, 72 mg, 0.30 mmol), DMAP (16.7 mg, 0.136 mmol) and AcCN (1 ml) was heated for 18 h at 70° C. in a sealed vial under an Ar atmosphere. The cooled reaction mixture was partitioned between saturated aqueous NaHCO$_3$ and DCM, extracted 2× with DCM, dried over Na$_2$SO$_4$ and evaporated. Purification by normal phase chromatography using a 12 g RediSep® column, eluting with a gradient from heptane to EtOAc, gave the title compound as a white solid. (UPLC-MS 6) $t_R$ 0.87 min; ESI-MS 423.3 [M+H]$^+$.

Intermediate 58: 1-((2-(1,3-dioxolan-2-yl)-6-(methylamino)pyridin-3-yl)methyl)pyrrolidin-2-one A mixture of 2-(1,3-dioxolan-2-yl)-6-(methylamino)nicotinaldehyde (Intermediate 49, 315 mg, 1.06 mmol), methyl 4-aminobutanoate hydrochloride (244 mg, 1.59 mmol), Et$_3$N (0.25 ml, 1.80 mmol) and 1,2-dichloroethane (5 ml) was stirred for 2.5 h at room temperature. NaBH(OAc)$_3$ (337 mg, 1.59 mmol) was added and the reaction mixture stirred for 18 h at room temperature. Additional methyl 4-aminobutanoate hydrochloride (244 mg, 1.59 mmol) and Et$_3$N (0.25 ml, 1.80 mmol) were added and after a further 1 h NaBH(OAc)$_3$ (337 mg, 1.59 mmol) was added. The reaction mixture was stirred for 48 h, then partitioned between saturated aqueous NaHCO$_3$ and DCM, extracted 2× with DCM and the combined organic layers evaporated onto isolute HM-N Sorbent®. Purification by normal phase chromatography using a 24 g RediSep® column, eluting with a gradient from heptane to EtOAc and then DCM to 10% MeOH in DCM, gave the title compound. (UPLC-MS 6) $t_R$ 0.41 min; ESI-MS 278.4 [M+H]$^+$.

Intermediate 59: phenyl (5-cyanopyridin-2-yl)carbamate

Phenyl chloroformate (0.53 ml, 4.20 mmol) was added dropwise to a stirred solution of 6-aminonicotinonitrile (0.50 g, 4.20 mmol) and pyridine (0.39 ml, 4.83 mmol) in THF (10 ml) cooled with an ice bath. After 30 minutes the reaction mixture was filtered, the solid washed 3× with Et$_2$O and the filtrate evaporated to give the title compound. (UPLC-MS 6) $t_R$ 0.92 min; ESI-MS 240.1 [M+H]$^+$.

Intermediate 60: 1-(6-(1,3-dioxolan-2-yl)-5-((2-oxopyrrolidin-1-yl)methyl)pyridin-2-yl)-3-(5-cyano-4-((2-methoxyethyl)amino)pyridin-2-yl)-1-methylurea 4-Nitrophenyl chloroformate (107 mg, 0.53 mmol) was added over 5 minutes to a solution of 6-amino-4-((2-methoxyethyl)amino)nicotinonitrile (Intermediate 8, 102 mg, 0.53 mmol) and pyridine (0.049 ml, 0.61 mmol) in THF (2 ml) cooled with an ice bath under a positive pressure of Ar. The reaction mixture was stirred for 3 h at 0° C. and 1-((2-(1,3-dioxolan-2-yl)-6-(methylamino)pyridin-3-yl) methyl)pyrrolidin-2-one (Intermediate 58, 118 mg, 0.43 mmol) and DMAP (71 mg, 0.58 mmol) in THF (2 ml) were added, the reaction mixture warmed to room temperature, stirred for 1 h then heated at 70° C. for 18 h. The cooled reaction mixture was partitioned between saturated aqueous NaHCO$_3$ and DCM, extracted 2× with DCM and evaporated onto isolute HM-N Sorbent®. (UPLC-MS 7) $t_R$ 0.83 min; ESI-MS 496.4 [M+H]$^+$.

Intermediate 61: 1-(6-(1,3-dioxolan-2-yl)-5-((4-methyl-2-oxopiperazin-1-yl)methyl)pyridin-2-yl)-3-(5-cyano-4-isopropoxypyridin-2-yl)-1-methylurea A mixture of 1-((2-(1,3-dioxolan-2-yl)-6-(methylamino)pyridin-3-yl)methyl)-4-methylpiperazin-2-one (Intermediate 62, 65 mg, 0.21 mmol), phenyl (5-cyano-4-isopropoxypyridin-2-yl)carbamate (Intermediate 63, 139 mg, 0.47 mmol), DMAP (29 mg, 0.23 mmol) and AcCN (1 ml) was heated for 1 h at 70° C. in a sealed vial under an Ar atmosphere. The cooled reaction mixture was partitioned between 5% aqueous citric acid solution and DCM, extracted 2× with DCM and evaporated onto isolute HM-N Sorbent®. Purification by normal phase chromatography using a 12 g RediSep® column, eluting with a gradient from heptane to EtOAc then DCM to 10% MeOH in DCM, gave the title compound. (UPLC-MS 6) $t_R$ 0.83 min; ESI-MS 510.1 [M+H]$^+$.

Intermediate 62: 1-((2-(1,3-dioxolan-2-yl)-6-(methylamino)pyridin-3-yl)methyl)-4-methylpiperazin-2-one A mixture of 2-(1,3-dioxolan-2-yl)-6-(methylamino)nicotinaldehyde (Intermediate 49, 300 mg, 1.01 mmol), ethyl 2-((2-aminoethyl)(methyl)amino)acetate dihydrochloride (Intermediate 64, 414 mg, 2.02 mmol), Et$_3$N (1.40 ml, 10.1 mmol) and MeOH (10 ml) was stirred for 2.5 h at room temperature. NaBH(OAc)$_3$ (641 mg, 3.03 mmol) was added and the reaction mixture stirred for 18 h at room temperature. Additional NaBH(OAc)$_3$ (641 mg, 3.03 mmol) was added and stirring continued for a further 18 h, then NaBH$_3$CN (190 mg, 3.03 mmol) was added and stirring continued for a further 4 days. The reaction mixture was partitioned between saturated aqueous NaHCO$_3$ and DCM, extracted 2× with DCM and the combined organic layers dried over Na$_2$SO$_4$ and evaporated. Purification by normal phase chromatography using a 24 g RediSep® column, eluting with a gradient from DCM to 20% MeOH in DCM, gave the title compound. $^1$H NMR (400 MHz, DMSO-d$_6$) δ 7.19 (d, 1H), 6.54-6.46 (m, 1H), 6.44 (d, 1H), 5.69 (s, 1H), 4.51 (s, 2H), 4.20-4.13 (m, 2H), 3.96-3.89 (m, 2H), 3.15-3.06 (m, 4H), 2.74 (s, 3H), 2.60-2.51 (m, 2H), 2.22 (s, 3H).

Intermediate 63: phenyl (5-cyano-4-isopropoxypyridin-2-yl)carbamate

Phenyl chloroformate (3.89 ml, 31.0 mmol) was added drop wise to a mixture of 6-amino-4-isopropoxynicotinonitrile (Intermediate 28, 2.5 g, 14.11 mmol) and pyridine (2.51 ml, 31.0 mmol) in THF (100 ml) at room temperature. The reaction mixture was stirred for 12 h at room temperature, additional pyridine (2.51 ml, 31.0 mmol) added, before stirring for an additional 12 h and then partitioned between EtOAc and saturated aqueous NaHCO$_3$ solution. The organic layer was washed with saturated brine, dried over MgSO$_4$ and evaporated. The residue was triturated with Et$_2$O and the product obtained by filtration as a beige solid. (UPLC-MS 7) t$_R$ 1.09; ESI-MS 298.2 [M+H]$^+$.

Intermediate 64: ethyl 2-((2-aminoethyl)(methyl)amino)acetate dihydrochloride

Concentrated hydrochloric acid (10 ml) was added to a solution of ethyl 2-((2-((tert-butoxycarbonyl)amino)ethyl)(methyl)amino)acetate (Intermediate 65, 3.05 g, 11.13 mmol) in THF (20 ml) and EtOH (100 ml) at room temperature. After stirring 1 h at room temperature the reaction mixture was evaporated, ethanol (20 ml) added, evaporated, further ethanol (50 ml) added and then stirred at 60° C. for 70 min. The cooled reaction mixture was then evaporated to give the title compound as a pale-yellow glass. $^1$H NMR (400 MHz, DMSO-d$_6$) δ 8.58 (s, br, 3H), 4.19 (q, 2H), 4.26-4.15 (m, 2H), 3.44 (s, br, 2H), 3.21 (s, br, 2H), 2.88 (s, 3H), 1.21 (t, 3H).

Intermediate 65: ethyl 2-((2-((tert-butoxycarbonyl)amino)ethyl)(methyl)amino)acetate Ethyl bromoacetate (1.27 ml, 11.48 mmol) was added to a mixture of tert-butyl (2-(methylamino)ethyl)carbamate (2.0 g, 11.48 mmol), triethylamine (4.81 ml) and THF (24 ml) at 0° C. After stirring 24 h at room temperature the reaction mixture was partitioned between saturated aqueous NaHCO$_3$ and DCM, extracted 2× with DCM, the organic layers dried over Na$_2$SO$_4$ and evaporated to give the title compound as a clear pale-yellow oil. $^1$H NMR (400 MHz, CDCl$_3$) δ 5.20 (s, br, 1H), 4.18 (q, 2H), 3.24 (s, 2H), 3.22-3.16 (m, 2H), 2.65-2.61 (m, 2H), 2.38 (s, 3H), 1.42 (s, 9H), 1.24 (t, 3H).

Intermediate 66: 1-(6-(1,3-dioxolan-2-yl)-5-(1-methyl-1H-pyrazol-4-yl)pyridin-2-yl)-3-(5-cyano-4-((2-hydroxy-2-methylpropyl)amino)pyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-(1-methyl-1H-pyrazol-4-yl)pyridin-2-yl)(methyl)carbamate (Intermediate 42) and 6-amino-4-((2-hydroxy-2-methylpropyl)amino)nicotinonitrile (Intermediate 67) were used in place of phenyl (6-(1,3-dioxolan-2-yl)-5-(1-methyl-1H-pyrazol-4-yl)pyridin-2-yl)(ethyl)carbamate (Intermediate 35) and 6-amino-4-((2-methoxyethyl)amino)nicotinonitrile (Intermediate 8). (UPLC-MS 7) t$_R$ 0.89; ESI-MS 493.3 [M+H]$^+$.

Intermediate 67: 6-amino-4-((2-hydroxy-2-methylpropyl)amino)nicotinonitrile

A mixture of 1-amino-2-methylethanol (1.0 g, 11.22 mmol), 6-amino-4-fluoronicotinonitrile (Intermediate 10, 1.54 g, 11.22 mmol) and triethylamine (6.26 ml, 44.9 mmol) was heated at 60° C. in a septum sealed reaction vessel under argon for 18 h. The reaction mixture was then cooled, evaporated, partitioned between aqueous NaHCO$_3$ solution and n-BuOH, extracted 3× with n-BuOH, the combined organic layers dried over Na$_2$SO$_4$ and evaporated. The residue was triturated with Et$_2$O (100 ml) and DCM (5 ml) to give the title compound as a beige solid. (UPLC-MS 6) t$_R$ 0.35; ESI-MS 207.2 [M+H]$^+$.

Intermediate 68: 1-(6-(1,3-dioxolan-2-yl)-5-((2-oxopyrrolidin-1-yl)methyl)pyridin-2-yl)-3-(5-cyano-4-isopropoxypyridin-2-yl)-1-methylurea The title compound was prepared in an analogous manner to 1-(6-(1,3-dioxolan-2-yl)-5-((4-methyl-2-oxopiperazin-1-yl)methyl)pyridin-2-yl)-3-(5-cyano-4-isopropoxypyridin-2-yl)-1-methylurea (Intermediate 61) except 1-((2-(1,3-dioxolan-2-yl)-6-(methylamino)pyridin-3-yl)methyl)pyrrolidin-2-one (Intermediate 58) was used in place of 1-((2-(1,3-dioxolan-2-yl)-6-(methylamino)pyridin-3-yl)methyl)-4-methylpiperazin-2-one (Intermediate 62). (UPLC-MS 6) t$_R$ 1.03; ESI-MS 481.3 [M+H]$^+$.

Intermediate 69: 1-(6-(1,3-dioxolan-2-yl)-5-((4-methyl-2-oxopiperazin-1-yl)methyl)pyridin-2-yl)-3-(5-cyano-4-((2-methoxyethyl)amino)pyridin-2-yl)-1-methylurea 6-amino-4-((2-methoxyethyl)amino)nicotinonitrile (Intermediate 8, 188 mg, 0.98 mmol) was added to a stirred solution of di(1H-1,2,4-triazol-1-yl)methanone (169 mg, 1.03 mmol) in DMF (3 ml) at room temperature under an atmosphere of Ar. After 2 h a solution of 1-((2-(1,3-dioxolan-2-yl)-6-(methylamino)pyridin-3-yl)methyl)-4-methylpiperazin-2-one (Intermediate 62, 150 mg, 0.49 mmol) in DMF (4 ml) was added. The reaction mixture was stirred for 18 h, partitioned between saturated aqueous NaHCO$_3$ solution, extracted with 2×DCM, the combined organic layers washed with brine, dried over Na$_2$SO$_4$ and evaporated onto isolute HM-N Sorbent®. Purification by normal phase chromatography using a 40 g RediSep® column, eluting with a gradient from heptane to EtOAc, gave the title compound. (UPLC-MS 6) $t_R$ 0.64; ESI-MS 525.3 [M+H]$^+$.

Intermediate 70: 1-(6-(1,3-dioxolan-2-yl)-5-(1-methyl-1H-pyrazol-4-yl)pyridin-2-yl)-3-(5-cyano-4-isopropoxypyridin-2-yl)-1-methylurea The title compound was prepared in an analogous manner to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34), except phenyl (6-(1,3-dioxolan-2-yl)-5-(1-methyl-1H-pyrazol-4-yl)pyridin-2-yl)(methyl)carbamate (Intermediate 42) and 6-amino-4-isopropoxynicotinonitrile (Intermediate 28) were used in place of phenyl (6-(1,3-dioxolan-2-yl)-5-(1-methyl-1H-pyrazol-4-yl)pyridin-2-yl)(ethyl)carbamate (Intermediate 35) and 6-amino-4-((2-methoxyethyl)amino)-nicotinonitrile (Intermediate 8). (UPLC-MS 7) $t_R$ 1.11; ESI-MS 464.3 [M+H]$^+$.

Intermediate 71: (racemic) 1-(6-(1,3-dioxolan-2-yl)-5-((3-methoxypyrrolidin-1-yl)methyl)pyridin-2-yl)-3-(5-cyano-4-isopropoxypyridin-2-yl)-1-methylurea The title compound was prepared in an analogous manner to 1-(6-(1,3-dioxolan-2-yl)-5-((4-methyl-2-oxopiperazin-1-yl)methyl)pyridin-2-yl)-3-(5-cyano-4-isopropoxypyridin-2-yl)-1-methylurea (Intermediate 61) except (racemic) 6-(1,3-dioxolan-2-yl)-5-((3-methoxypyrrolidin-1-yl)methyl)-N-methylpyridin-2-amine (Intermediate 72) was used in place of 1-((2-(1,3-dioxolan-2-yl)-6-(methylamino)pyridin-3-yl)methyl)-4-methylpiperazin-2-one (Intermediate 62). (UPLC-MS 6) $t_R$ 0.84; ESI-MS 497.3 [M+H]$^+$.

Intermediate 72: (racemic) 6-(1,3-dioxolan-2-yl)-5-((3-methoxypyrrolidin-1-yl)methyl)-N-methylpyridin-2-amine The title compound was prepared in an analogous manner to 6-(1,3-dioxolan-2-yl)-N-methyl-5-((4-methylpiperazin-1-yl)methyl)pyridin-2-amine (Intermediate 55) except 3-methoxypyrrolidine was used in place of 1-methylpiperazine. (UPLC-MS 6) $t_R$ 0.42; ESI-MS 294.2 [M+H]$^+$.

Intermediate 73: N2-(1-(6-(1,3-dioxolan-2-yl)-5-(1-methyl-1H-pyrazol-4-yl)pyridin-2-yl)-1H-imidazol-2-yl)-N4-(2-methoxyethyl)-5-(trifluoromethyl) pyridine-2,4-diamine A mixture of 1-(6-(1,3-dioxolan-2-yl)-5-(1-methyl-1H-pyrazol-4-yl)pyridin-2-yl)-1H-imidazol-2-amine (Intermediate 74, 30 mg, 0.094 mmol), 2-chloro-N-(2-methoxyethyl)-5-(trifluoromethyl)pyridin-4-amine (Intermediate 75, 26 mg, 0.103 mmol), Pd$_2$(dba)$_3$ (1.7 mg, 0.002 mmol), Xantphos (2.2 mg, 0.004 mmol) and Cs$_2$CO$_3$ (43 mg, 0.131 mmol) in dioxane (0.4 ml) was heated at 100° C. for 42 h. Added additional Pd$_2$(dba)$_3$ (1.8 mg) and Xantphos (2.4 mg) and heated at 130° C. for 6 h. Added additional Pd$_2$(dba)$_3$ (1.8 mg) and Xantphos (2.4 mg) and continued heating at 130° C. After another 16 h, the reaction mixture was cooled to room temperature, diluted with H$_2$O and extracted with EtOAc (3×). The combined organic layers were dried over Na$_2$SO$_4$ and filtered. The filtrate was treated with PL-BnSH resin (Agilent Technologies), filtered and concentrated. The crude material was applied to a 24 g RediSep® silica column and purified by normal phase chromatography, eluting with 95:5:1 DCM/MeOH/conc. NH$_4$OH. Product-containing fractions were combined and evaporated. The residue was triturated with Et$_2$O and the title compound obtained by filtration as a beige solid. (UPLC-MS 3) $t_R$ 0.89; ESI-MS 531.2 [M+H]$^+$.

Intermediate 74: 1-(6-(1,3-dioxolan-2-yl)-5-(1-methyl-1H-pyrazol-4-yl)pyridin-2-yl)-1H-imidazol-2-amine A mixture of 1-(5-bromo-6-(1,3-dioxolan-2-yl)pyridin-2-yl)-1H-imidazol-2-amine (Intermediate 76, 500 mg, 1.53 mmol), 1-methyl-1H-pyrazole-4-boronic acid pinacolester (389 mg, 1.83 mmol), PdCl$_2$(dppf).CH$_2$Cl$_2$ (125 mg, 0.153 mmol) and Na$_2$CO$_3$ (421 mg, 3.97 mmol) in DME (6 ml) and H$_2$O (2 ml) was heated at 90° C. After 4.5 h, the reaction mixture was cooled to room temperature, diluted with H$_2$O and extracted with EtOAc (3×). The combined organic layers were dried over Na$_2$SO$_4$ and filtered. The filtrate was treated with PL-BnSH resin (Agilent Technologies), filtered and concentrated. The crude material was applied to a 120 g RediSep® silica column and purified by normal phase chromatography, eluting with 92.5:7.5:1 DCM/MeOH/conc. NH$_4$OH. Product-containing fractions were combined and evaporated to give the title compound as a brown solid. (UPLC-MS 3) $t_R$ 0.48; ESI-MS 313.1 [M+H]$^+$.

Intermediate 75: 2-chloro-N-(2-methoxyethyl)-5-(trifluoromethyl)pyridin-4-amine

2-Methoxyethylamine (1.0 ml, 11.57 mmol) was added drop wise to 2,4-dichloro-5-(trifluoromethyl)pyridine (500 mg, 2.32 mmol) at 0° C. and the mixture stirred at room temperature for 2.5 h. The reaction mixture was partitioned between saturated aqueous NaHCO$_3$ solution and DCM, the organic layer dried over Na$_2$SO$_4$ and evaporated. The residue was applied to a 120 g RediSep® silica column as a DCM solution and purified by normal phase chromatography, eluting with a gradient from DCM to 50% EtOAc in DCM. The title compound was obtained as the major regioisomer and elutes before the 4-chloro-N-(2-methoxyethyl)-5-(trifluoromethyl)pyridin-2-amine (ratio 2:1). Product containing fractions were combined and evaporated to give the title compound as a yellow-white solid. (UPLC-MS 6) $t_R$ 0.96; ESI-MS 255.1 [M+H]$^+$.

Intermediate 76: 1-(5-bromo-6-(1,3-dioxolan-2-yl)pyridin-2-yl)-1H-imidazol-2-amine A mixture of 3,6-dibromo-2-(1,3-dioxolan-2-yl)pyridine (Intermediate 32, 2.0 g, 6.47 mmol), 2-aminoimidazole sulfate (1.30 g, 6.80 mmol), copper(I) iodide (0.123 g, 0.65 mmol), cesium carbonate (5.27 g, 16.18 mmol) and 8-hydroxyquinoline (0.141 g, 0.97 mmol) in t-butanol (9.4 ml) was heated at 100° C. After 23 h, the reaction mixture was cooled to room temperature, diluted with H$_2$O and extracted with EtOAc (3×). The combined organic layers were dried over Na$_2$SO$_4$ and evaporated. The crude material was triturated with DMF and the product obtained by filtration as a light brown solid. (UPLC-MS 3) $t_R$ 0.52; ESI-MS 311.1/313.1 [M+H]$^+$.

Intermediate 77: N2-(1-(6-(1,3-dioxolan-2-yl)-5-(1-methyl-1H-pyrazol-4-yl)pyridin-2-yl)-1H-pyrazol-5-yl)-N4-(2-methoxyethyl)-5-(trifluoromethyl) pyridine-2,4-diamine The title compound was prepared in an analogous manner to N2-(1-(6-(1,3-dioxolan-2-yl)-5-(1-methyl-1H-pyrazol-4- yl)pyridin-2-yl)-1H-imidazol-2-yl)-N4-(2-methoxyethyl)-5-(trifluoromethyl)pyridine-2,4-diamine (Intermediate 73) except 1-(6-(1,3-dioxolan-2-yl)-5-(1-methyl-1H-pyrazol-4-yl)pyridin-2-yl)-1H-pyrazol-5-amine (Intermediate 78) was used in place of 1-(6-(1,3-dioxolan-2-yl)-5-(1-methyl-1H-pyrazol-4-yl)pyridin-2-yl)-1H-imidazol-2-amine (Intermediate 74). (UPLC-MS 3) $t_R$ 1.23; ESI-MS 531.1 [M+H]⁺.

Intermediate 78: 1-(6-(1,3-dioxolan-2-yl)-5-(1-methyl-1H-pyrazol-4-yl)pyridin-2-yl)-1H-pyrazol-5-amine The title compound was prepared in an analogous manner to 1-(6-(1,3-dioxolan-2-yl)-5-(1-methyl-1H-pyrazol-4-yl)pyridin-2-yl)-1H-imidazol-2-amine (Intermediate 74) except 1-(5-bromo-6-(1,3-dioxolan-2-yl)pyridin-2-yl)-1H-pyrazol-5-amine (Intermediate 79) was used in place of 1-(5-bromo-6-(1,3-dioxolan-2-yl)pyridin-2-yl)-1H-imidazol-2-amine (Intermediate 76). (UPLC-MS 3) $t_R$ 0.69; ESI-MS 313.1 [M+H]⁺.

Intermediate 79: 1-(5-bromo-6-(1,3-dioxolan-2-yl)pyridin-2-yl)-1H-pyrazol-5-amine The title compound was prepared in an analogous manner to 1-(5-bromo-6-(1,3-dioxolan-2-yl)pyridin-2-yl)-1H-imidazol-2-amine (Intermediate 76) except 3-aminopyrazole was used in place of 2-aminoimidazole. The title compound elutes before the major regioisomer from the reaction: 1-(5-bromo-6-(1,3-dioxolan-2-yl)pyridin-2-yl)-1H-pyrazol-3-amine. (UPLC-MS 3) $t_R$ 0.83; ESI-MS 313.0 and 311.0 [M+H]⁺.

Intermediate 80: 1-(6-(1,3-dioxolan-2-yl)-5-(pyrrolidin-1-ylmethyl)pyridin-2-yl)-3-(5-cyano-4-isopropoxypyridin-2-yl)-1-methylurea The title compound was prepared in an analogous manner to 1-(6-(1,3-dioxolan-2-yl)-5-((4-methyl-2-oxopiperazin-1-yl)methyl)pyridin-2-yl)-3-(5-cyano-4-isopropoxypyridin-2-yl)-1-methylurea (Intermediate 61) except 6-(1,3-dioxolan-2-yl)-N-methyl-5-(pyrrolidin-1-ylmethyl)pyridin-2-amine (Intermediate 81) was used in place of 1-((2-(1,3-dioxolan-2-yl)-6-(methylamino)pyridin-3-yl)methyl)-4-methylpiperazin-2-one (Intermediate 62). (UPLC-MS 7) $t_R$ 0.84; ESI-MS 467.3 [M+H]⁺.

Intermediate 81: 6-(1,3-dioxolan-2-yl)-N-methyl-5-(pyrrolidin-1-ylmethyl)pyridin-2-amine The title compound was prepared in an analogous manner to 6-(1,3-dioxolan-2-yl)-N-methyl-5-((4-methylpiperazin-1-yl)methyl)pyridin-2-amine (Intermediate 55) except pyrrolidine was used in place of 1-methylpiperazine. (UPLC-MS 7) $t_R$ 0.37; ESI-MS 264.2 [M+H]⁺.

Intermediate 82: 3-(5-cyano-4-isopropoxypyridin-2-yl)-1-(4-(dimethoxymethyl)pyrimidin-2-yl)urea A mixture of 4-(dimethoxymethyl)pyridin-2-amine (35 mg, 0.207 mmol), phenyl (5-cyano-4-isopropoxypyridin-2-yl)carbamate (Intermediate 63, 92 mg, 0.309 mmol), 4-(dimethylamino)-pyridine (28 mg, 0.228 mmol) and acetonitrile (2 ml) was heated at 70° C. for 1 h in a sealed vial. The cooled mixture was partitioned between 5% aqueous citric acid and $CH_2Cl_2$, the organic layer dried over $Na_2SO_4$ and evaporated. The residue was purified by normal phase chromatography, 12 g RediSep® column, eluting with a gradient from heptane to EtOAc, to give the title compound. (UPLC-2 min 7) $t_R$ 1.00 min; ESI-MS 373.1 [M+H]⁺.

EXAMPLES

Example 1: 6-((2-(6-formylpyridin-2-yl)phenyl)amino)nicotinonitrile

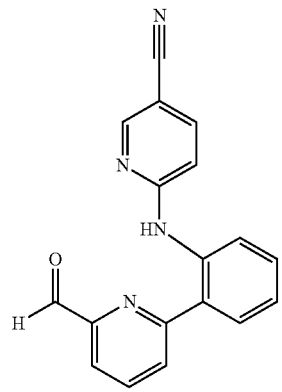 [SMILES: N#Cc1ccc(Nc2ccccc2-c2cccc(C=O)n2)nc1]

In a vial, a solution of 6-((2-(6-(hydroxymethyl)pyridin-2-yl)phenyl)amino)nicotinonitrile (Intermediate 1, 50 mg, 0.165 mmol) in dioxane (2 ml) was treated with manganese dioxide (216 mg, 2.48 mmol). The vial was flushed with argon, sealed and the reaction mixture stirred at 104° C. for 45 min. The reaction mixture was cooled to room temperature and filtered through plug of celite. The plug was eluted with EtOAc. The filtrate was concentrated under reduced pressure and the residue was purified by normal phase chromatography (4 g silica gel cartridge, heptanes/EtOAc 100:0 to 0:100) to give the title compound as a yellow solid. ¹H NMR (400 MHz, DMSO-$d_6$) δ 11.08 (s, 1H), 10.08 (s, 1H), 8.48 (d, 1H), 8.18-8.07 (m, 3H), 7.96-7.84 (m, 3H), 7.54-7.47 (m, 1H), 7.32-7.25 (m, 1H), 6.95 (d, 1H). (UPLC-MS 1) $t_R$ 1.06 min; ESI-MS 301.1 [M+H]⁺.

Example 2: 3-(5-cyano-4-((2-methoxyethyl)amino)pyridin-2-yl)-1-(6-formylpyridin-2-yl)-1-methylurea

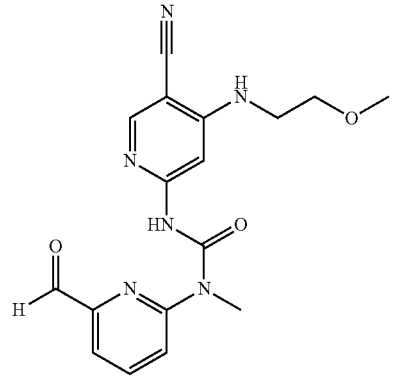 [SMILES: COCCNc1cc(NC(=O)N(C)c2cccc(C=O)n2)ncc1C#N]

A solution of 1-(6-(1,3-dioxolan-2-yl)pyridin-2-yl)-3-(5-cyano-4-((2-methoxyethyl)amino)pyridin-2-yl)-1-methylurea (Intermediate 6, 49 mg, 0.123 mmol) in THF (2 ml) and water (0.5 ml) was treated with conc. HCl (0.20 ml) and stirred at room temperature for 8 h. The reaction mixture was quenched with sat. aq. $NaHCO_3$ and extracted with DCM (3x). The combined org. layers were dried over $Na_2SO_4$, filtered and concentrated under vacuum. The crude material was triturated in EtOAc. Heptane was added to the mixture and then the suspension was centrifuged The mother liquor was removed and the solid dried to obtain the title compound as a white solid. $^1$H NMR (400 MHz, DMSO-$d_6$) δ 12.48 (s, 1H), 9.94 (d, 1H), 8.25 (s, 1H), 8.17-8.11 (m, 1H), 7.72 (dd, 1H), 7.68 (m, 1H), 7.47 (s, 1H), 6.97 (t, 1H), 3.55-3.49 (m, 2H), 3.46 (s, 3H), 3.41-3.35 (m, 2H), 3.29 (s, 3H). (UPLC-MS 3) $t_R$ 0.88 min; broad peak; ESI-MS 355.1 [M+H]$^+$.

Example 3: 3-(5-cyano-4-((2-methoxyethyl)amino) pyridin-2-yl)-1-(6-formylpyridin-2-yl)-1-(2-methoxyethyl)urea

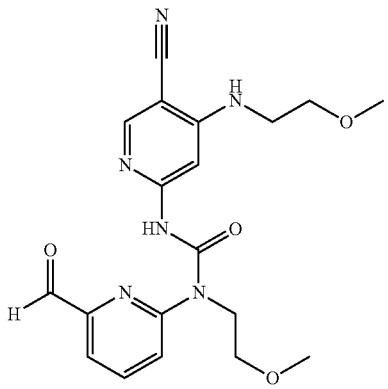 [SMILES: COCCNc1cc(NC(=O)N(CCOC)c2cccc(C=O)n2)ncc1C#N]

The title compound was prepared by a method similar to that of 1-(6-(1,3-dioxolan-2-yl)pyridin-2-yl)-3-(5-cyano-4-((2-methoxyethyl)amino)pyridin-2-yl)-1-methylurea (Example 2) by replacing 1-(6-(1,3-dioxolan-2-yl)pyridin-2-yl)-3-(5-cyano-4-((2-methoxyethyl)amino)pyridin-2-yl)-1-methylurea (Intermediate 6) with 1-(6-(1,3-dioxolan-2-yl) pyridin-2-yl)-3-(5-cyano-4-((2-methoxyethyl)amino) pyridin-2-yl)-1-(2-methoxyethyl)urea (Intermediate 12). $^1$H NMR (400 MHz, DMSO-$d_6$) δ 11.44 (s, 1H), 9.92 (s, 1H), 8.24 (s, 1H), 8.08 (t, 1H), 7.80 (d, 1H), 7.71 (d, 1H), 7.39 (s, 1H), 6.97 (t, 1H), 4.26 (t, 2H), 3.63 (t, 2H), 3.55-3.49 (m, 2H), 3.40-3.36 (m, 2H), 3.29-3.26 (m, 6H). (UPLC-MS 3) $t_R$ 0.93 min; broad peak; ESI-MS 399.1 [M+H]$^+$.

Example 4: (racemic) 3-(5-cyano-4-((2-methoxyethyl)amino)pyridin-2-yl)-1-(6-formylpyridin-2-yl)-1-((tetrahydrofuran-3-yl) methyl)urea

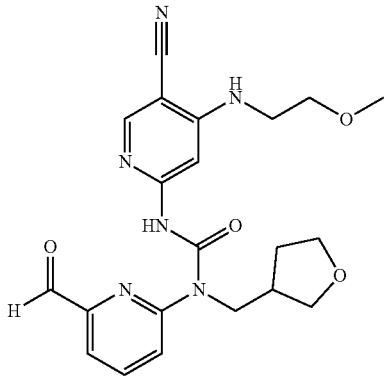 [SMILES: COCCNc1cc(NC(=O)N(CC2CCOC2)c2cccc(C=O)n2)ncc1C#N]

The title compound was prepared by a method similar to that of Example 2 by replacing 1-(6-(1,3-dioxolan-2-yl) pyridin-2-yl)-3-(5-cyano-4-((2-methoxyethyl)amino)pyridin-2-yl)-1-methylurea (Intermediate 6) with (racemic) 1-(6-(1,3-dioxolan-2-yl)pyridin-2-yl)-3-(5-cyano-4-((2-methoxyethyl)amino)pyridin-2-yl)-1-((tetrahydrofuran-3-yl)methyl)urea (Intermediate 15) and the crude material was purified by supercritical fluid chromatography (SFC 1, DEAP column). $^1$H NMR (400 MHz, DMSO-$d_6$) δ 11.62 (s, 1H), 9.94 (d, 1H), 8.23 (s, 1H), 8.11 (t, 1H), 7.74 (m, 2H), 7.42 (s, 1H), 6.93 (t, 1H), 4.17-4.02 (m, 2H), 3.81-3.74 (m, 1H), 3.66-3.56 (m, 2H), 3.53 (t, 2H), 3.45 (dd, 1H), 3.39 (q, 2H), 3.29 (s, 3H), 2.62-2.53 (m, 1H), 1.95-1.84 (m, 1H), 1.56-1.67 (m, 1H). (UPLC-MS 3) $t_R$ 0.89 min; ESI-MS 425.2 [M+H]$^+$.

Example 5: (racemic) 3-(5-cyano-4-((2-methoxyethyl)amino)pyridin-2-yl)-1-(6-formyl-5-(hydroxymethyl)pyridin-2-yl)-1-((tetrahydrofuran-3-yl)methyl) urea

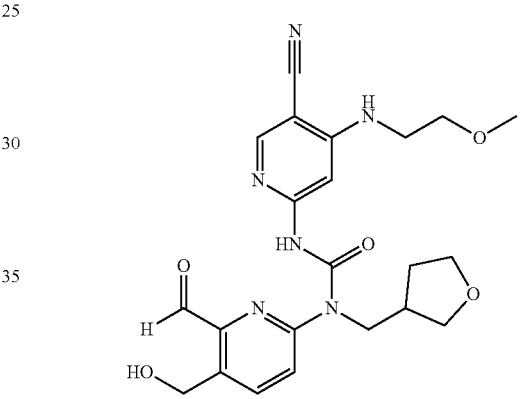

Concentrated hydrochloric acid (0.36 ml) was added to 1-(5-(((tert-butyldimethylsilyl)oxy)methyl)-6-(1,3-dioxolan-2-yl)pyridin-2-yl)-3-(5-cyano-4-((2-methoxyethyl) amino)pyridin-2-yl)-1-((tetrahydrofuran-3-yl)methyl)urea (Intermediate 18, 135 mg, 0.220 mmol) in THF (2 ml) and water (2 ml) at room temperature. After stirring for 40 minutes additional concentrated hydrochloric acid (0.36 ml) was added and this was repeated twice more after 1.3 and 2.3 hours. The reaction mixture was then stirred for a further 30 minutes, partitioned between saturated aqueous $NaHCO_3$ and DCM, extracted 2x with DCM, the organic layers dried over $Na_2SO_4$ and evaporated. The residue was sonicated with EtOAc (3 ml) at 45° C. and heptane (3 ml) added. The title compound was then isolated by filtration as a white solid. $^1$H NMR (400 MHz, DMSO-$d_6$) mixture of aldehyde and internal hemi-acetal, data for the predominant hemi-acetal form: δ 11.02 (s, 1H), 8.16 (s, 1H), 7.92 (d, 1H), 7.43 (d, 1H), 7.41 (s, 1H), 7.03 (d, 1H), 6.91 (t, br, 1H), 6.16 (d, 1H), 5.09 (d, 1H), 4.95 (d, 1H), 4.09-3.96 (m, 2H), 3.76-3.70 (m, 1H), 3.61-3.48 (m, 4H), 3.43-3.24 (m, 4H), 3.11 (s, 3H), 1.91-1.81 (m, 1H), 1.61-1.51 (m, 1H). (UPLC-MS 7) $t_R$ 0.71 min; ESI-MS 455.4 [M+H]$^+$.

Examples 6 and 7: (S)-3-(5-cyano-4-((2-methoxy-ethyl)amino)pyridin-2-yl)-1-(6-formylpyridin-2-yl)-1-((tetrahydrofuran-3-yl)methyl)urea and (R)-3-(5-cyano-4-((2-methoxyethyl)amino)pyridin-2-yl)-1-(6-formylpyridin-2-yl)-1-((tetrahydrofuran-3-yl)methyl)urea

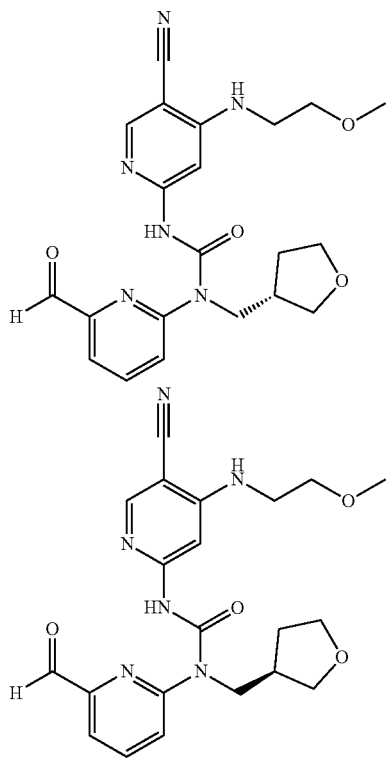

Concentrated hydrochloric acid (1.56 ml) was added to the first eluting enantiomer of 1-(6-(1,3-dioxolan-2-yl)pyridin-2-yl)-3-(5-cyano-4-((2-methoxyethyl)amino)pyridin-2-yl)-1-((tetrahydrofuran-3-yl)methyl)urea (Intermediate 24, 110 mg, 0.235 mmol) in THF (10 ml) and water (10 ml) at room temperature. After stirring for 48 h the reaction mixture was partitioned between saturated aqueous NaHCO₃ and DCM, extracted 3× with DCM, the organic layers dried over Na₂SO₄ and evaporated. The residue was triturated with EtOAc and heptane to give the title compound as a white solid. Similarly the second eluting enantiomer (Intermediate 25) was deprotected in an analagous manner.

Example 8: 6-(3-(5-cyano-4-isopropoxypyridin-2-yl)-1-methylureido)-2-formylnicotinic acid

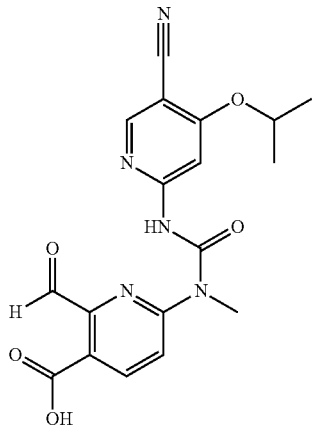 [SMILES: CC(C)Oc1cc(NC(=O)N(C)c2ccc(C(=O)O)c(C=O)n2)ncc1C#N]

Concentrated hydrochloric acid (0.48 ml) was added to 1-(6-(1,3-dioxolan-2-yl)-5-(4-methylpiperazine-1-carbonyl)pyridin-2-yl)-3-(5-cyano-4-isopropoxypyridin-2-yl)-1-methylurea (Intermediate 26, 74 mg, 0.145 mmol) in THF (3 ml) and water (1.5 ml) at room temperature. After stirring for 24 h the reaction mixture was partitioned between saturated aqueous NaHCO₃ and DCM, extracted 2× with DCM, the organic layers dried over Na₂SO₄ and evaporated. The residue was filtered through a AnaLogix C18 SF40 150 g SuperFlash column eluting with aqueous AcCN containing 0.1% CF₃CO₂H and the product containing fractions evaporated to give the title compound. $^1$H NMR (400 MHz, DMSO-$d_6$): δ 12.28 (s, 1H), 8.58 (s, 1H), 8.44 (d, 1H), 8.31 (d, 1H), 7.87 (s, 1H), 7.62 (d, 1H), 6.61 (d, 1H), 4.89-4.81 (m, 1H), 3.53 (s, 3H), 1.39 (d, 6H). (UPLC-MS 6) $t_R$ 0.90 min; ESI-MS 384.2 [M+H]⁺.

Example 9: 6-(3-(5-cyano-4-((2-methoxyethyl)amino)pyridin-2-yl)-1-methylureido)-2-formylnicotinic acid

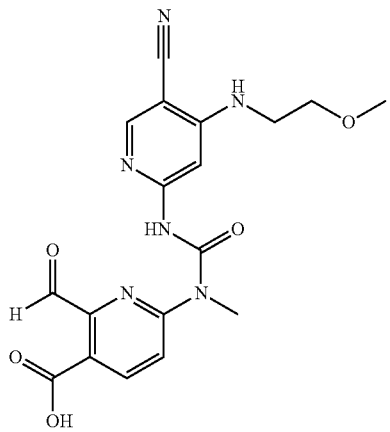 [SMILES: COCCNc1cc(NC(=O)N(C)c2ccc(C(=O)O)c(C=O)n2)ncc1C#N]

Concentrated hydrochloric acid (0.44 ml) was added to 1-(6-(1,3-dioxolan-2-yl)-5-(4-methylpiperazine-1-carbonyl)pyridin-2-yl)-3-(5-cyano-4-((2-methoxyethyl)amino)pyridin-2-yl)-1-methylurea (Intermediate 33, 70 mg, 0.133 mmol) in THF (3 ml) and water (1.5 ml) at room temperature. After stirring for 18 h the reaction mixture was partitioned between saturated aqueous NaHCO₃ and DCM, extracted 2× with DCM, the organic layers dried over Na₂SO₄ and evaporated. The residue was filtered through a AnaLogix C18 SF40 150 g SuperFlash column eluting with aqueous AcCN containing 0.1% CF₃CO₂H and the product containing fractions evaporated, further purification by reversed phase chromatography to give the title compound. $^1$H NMR (400 MHz, DMSO-$d_6$): δ 12.05 (s, 1H), 8.44 (s, br, 1H), 8.30-8.25 (m, 2H), 7.55 (d, 1H), 7.46 (s, 1H), 7.04 (s, br, 1H), 6.59 (s, br, 1H), 3.54-3.48 (m, 5H), 3.41-3.35 (m, 2H), 3.29 (s, 3H). (UPLC-MS 7) $t_R$ 0.71 min; ESI-MS 399.3 [M+H]⁺.

Example 10: 3-(5-cyano-4-((2-methoxyethyl)amino) pyridin-2-yl)-1-ethyl-1-(6-formyl-5-(1-methyl-1H-pyrazol-4-yl)pyridin-2-yl)urea

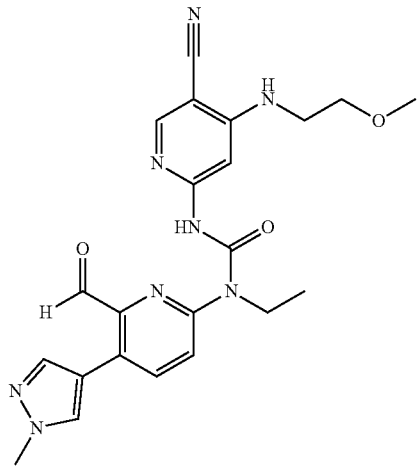 [SMILES: CCN(C(=O)Nc1cc(NCCOC)c(C#N)cn1)c1ccc(-c2cnn(C)c2)c(C=O)n1]

Concentrated hydrochloric acid (0.40 ml) was added to 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34, 60 mg, 0.097 mmol) in THF (3 ml) and water (0.4 ml) at room temperature. After stirring for 18 h the reaction mixture was partitioned between saturated aqueous $NaHCO_3$ and DCM, extracted 2× with DCM, the organic layers dried over $Na_2SO_4$ and evaporated. The residue was absorbed onto isolute HM-N Sorbent® and purified by normal phase chromatography using a 12 g RediSep® column, eluting with a gradient from heptane to EtOAc. Product containing fractions were then combined and evaporated to give the title compound. $^1$H NMR (400 MHz, DMSO-$d_6$): δ 12.44 (s, 1H), 10.11 (s, 1H), 8.26 (s, 1H), 8.17 (s, 1H), 8.10 (d, 1H), 7.83 (s, 1H), 7.50 (s, 1H), 6.93 (t, br, 1H), 4.12-4.03 (m, 2H), 3.92 (s, 3H), 3.55-3.48 (m, 2H), 3.40-3.33 (m, 2H), 3.30 (s, 3H), 1.23 (t, 3H). (UPLC-MS 6) $t_R$ 1.10 min; ESI-MS 477.3 [M+H]$^+$.

Example 11: 3-(5-cyano-4-(isopropylamino)pyridin-2-yl)-1-ethyl-1-(6-formyl-5-(1-methyl-1H-pyrazol-4-yl)pyridin-2-yl)urea

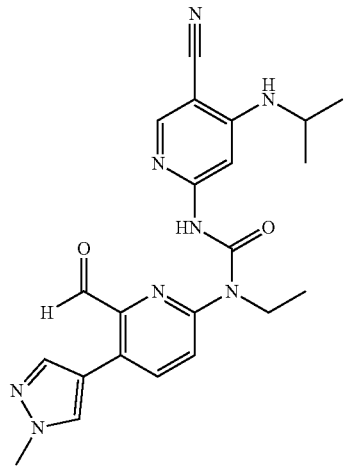 [SMILES: CCN(C(=O)Nc1cc(NC(C)C)c(C#N)cn1)c1ccc(-c2cnn(C)c2)c(C=O)n1]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-(1-methyl-1H-pyrazol-4-yl)pyridin-2-yl)-3-(5-cyano-4-(isopropylamino)pyridin-2-yl)-1-ethylurea (Intermediate 38) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-$d_6$): δ 12.43 (s, 1H), 10.10 (s, 1H), 8.24 (s, 1H), 8.17 (s, 1H), 8.10 (d, 1H), 7.83 (s, 1H), 7.66 (d, 1H), 7.53 (s, 1H), 6.64 (d, br, 1H), 4.11-4.03 (m, 2H), 3.92 (s, 3H), 3.80-3.71 (m, 1H), 1.25-1.16 (m, 9H). (UPLC-MS 6) $t_R$ 0.96/1.00 min; sample dissolved in MeOH shows a double peak; ESI-MS 433.3 [M+H]$^+$.

Example 12: 3-(5-cyano-4-isopropoxypyridin-2-yl)-1-ethyl-1-(6-formyl-5-(1-methyl-1H-pyrazol-4-yl)pyridin-2-yl)urea

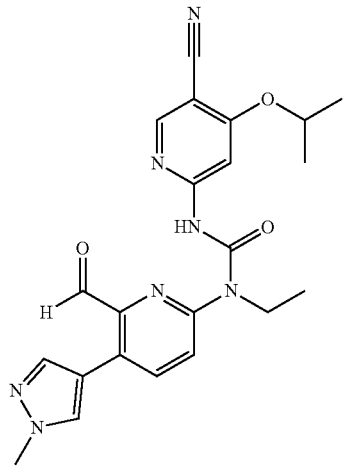 [SMILES: CCN(C(=O)Nc1cc(OC(C)C)c(C#N)cn1)c1ccc(-c2cnn(C)c2)c(C=O)n1]

The title compound was prepared in an analogous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-(1-methyl-1H-pyrazol-4-yl)pyridin-2-yl)-3-(5-cyano-4-(isopropoxyamino)pyridin-2-yl)-1-ethylurea (Intermediate 40) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-$d_6$): δ 12.71 (s, 1H), 10.12 (s, 1H), 8.56 (s, 1H), 8.18 (s, 1H), 8.11 (d, 1H), 7.91 (s, 1H), 7.84 (s, 1H), 7.70 (d, 1H), 4.90-4.78 (m, 1H), 4.13-4.04 (m, 2H), 3.92 (s, 3H), 1.42-1.36 (m, 6H), 1.20 (t, br, 3H).

(UPLC-MS 7) $t_R$ 1.05/1.07 min; sample dissolved in MeOH shows a double peak; ESI-MS 434.3 [M+H]$^+$.

Example 13: 3-(5-cyano-4-((2-methoxyethyl)amino) pyridin-2-yl)-1-methyl-1-(6-formyl-5-(1-methyl-1H-pyrazol-4-yl)pyridin-2-yl)urea

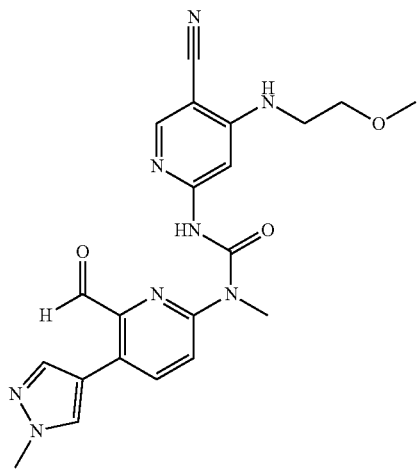 [SMILES: COCCNc1cc(NC(=O)N(C)c2ccc(-c3cnn(C)c3)c(C=O)n2)ncc1C#N]

The title compound was prepared in an analogous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-methylurea (Intermediate 41) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-d$_6$): b 12.57 (s, 1H), 10.12 (s, 1H), 8.26 (s, 1H), 8.17 (s, 1H), 8.13 (d, 1H), 7.83 (s, 1H), 7.67 (d, 1H), 7.49 (s, 1H), 6.95 (d, br, 1H), 3.92 (s, 3H), 3.56-3.50 (m, 2H), 3.46 (s, 3H), 3.42-3.35 (m, 2H), 3.29 (s, 3H). (UPLC-MS 6) $t_R$ 0.66/0.81 min; merged peaks with hydrate; ESI-MS 435.1 [M+H]$^+$.

Example 14: 3-(5-cyano-4-(isopropylamino)pyridin-2-yl)-1-(6-formyl-5-(1-methyl-1H-pyrazol-4-yl)pyridin-2-yl)-1-methylurea

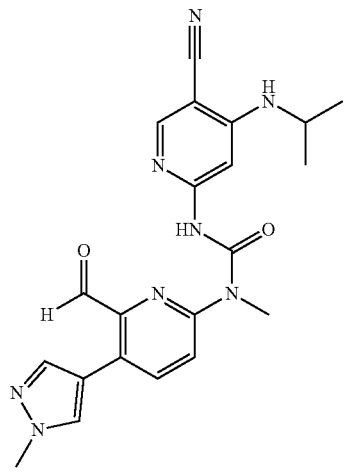 [SMILES: CC(C)Nc1cc(NC(=O)N(C)c2ccc(-c3cnn(C)c3)c(C=O)n2)ncc1C#N]

The title compound was prepared in an analogous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-(1-methyl-1H-pyrazol-4-yl)pyridin-2-yl)-3-(5-cyano-4-(isopropylamino)pyridin-2-yl)-1-methylurea (Intermediate 44) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-d$_6$): δ 12.55 (s, 1H), 10.12 (s, 1H), 8.29 (s, 1H), 8.25 (s, 1H), 8.13 (d, 1H), 7.83 (s, 1H), 7.65 (d, 1H), 7.49 (s, 1H), 6.65 (d, br, 1H), 3.92 (s, 3H), 3.82-3.70 (m, 1H), 3.46 (s, 3H), 1.24 (d, 6H). (UPLC-MS 6) $t_R$ 0.94/1.06 min; merged peaks with hydrate; ESI-MS 419.2 [M+H]$^+$.

Example 15: N-((6-(3-(5-cyano-4-((2-methoxyethyl)amino)pyridin-2-yl)-1-methylureido)-2-formylpyridin-3-yl)methyl)-N-methylacetamide

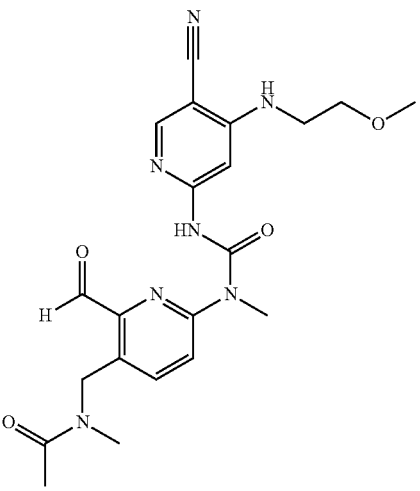 [SMILES: COCCNc1cc(NC(=O)N(C)c2ccc(CN(C)C(C)=O)c(C=O)n2)ncc1C#N]

Concentrated hydrochloric acid (0.50 ml) was added to N-((6-(3-(5-cyano-4-((2-methoxyethyl)amino)pyridin-2-yl)-1-methylureido)-2-(1,3-dioxolan-2-yl) pyridin-3-yl)methyl)-N-methylacetamide (Intermediate 45, 100 mg, 0.194 mmol) in THF (2 ml) at room temperature. The reaction mixture was stirred for a further 18 h, then neutralised with saturated aqueous NaHCO$_3$, filtered and the solid washed with water. The solid residue was sonicated with Et$_2$O and DCM and the title compound was isolated by filtration as a white solid. $^1$H NMR (400 MHz, DMSO-d$_6$) mixture of rotamers: δ 12.47 (s, 1H), 10.07 (s, 1H), 8.23 (s, 1H), 7.73-7.55 (m, 2H), 7.44 (s, 1H), 6.87 (s, br, 1H), 4.95 and 4.87 (s, 2H), 3.54-3.25 (m, 10H), 3.00 and 2.84 (s, 3H), 2.12 and 1.97 (s, 3H). (UPLC-MS 7) $t_R$ 0.81 min; ESI-MS 440.2 [M+H]$^+$.

Example 16: 3-(5-cyano-4-((2-methoxyethyl)amino)pyridin-2-yl)-1-(5-(difluoromethyl)-6-formylpyridin-2-yl)-1-methylurea

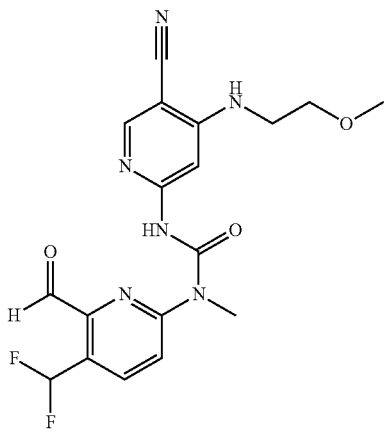 [SMILES: COCCNc1cc(NC(=O)N(C)c2ccc(C(F)F)c(C=O)n2)ncc1C#N]

The title compound was prepared in an analagous manner to N-((6-(3-(5-cyano-4-((2-methoxyethyl)amino)pyridin-2-yl)-1-methylureido)-2-formylpyridin-3-yl)methyl)-N-methylacetamide (Example 15) except 3-(5-cyano-4-((2-methoxyethyl)amino)pyridin-2-yl)-1-(5-(difluoromethyl)-6-(1,3-dioxolan-2-yl)pyridin-2-yl)-1-methylurea (Intermediate 50) was used in place of N-((6-(3-(5-cyano-4-((2-methoxyethyl)amino)pyridin-2-yl)-1-methylureido)-2-(1,3-dioxolan-2-yl)pyridin-3-yl)methyl)-N-methylacetamide (Intermediate 45). $^1$H NMR (400 MHz, DMSO-d$_6$): δ 12.20 (s, 1H), 9.99 (s, 1H), 8.31 (d, 1H), 8.26 (s, 1H), 7.78 (d, 1H), 7.55 (t, 1H), 7.44 (s, 1H), 6.98 (s, br, 1H), 3.56-3.45 (m, 5H), 3.43-3.31 (m, 2H), 3.28 (s, 3H). (UPLC-MS 7) t$_R$ 1.03 min; ESI-MS 405.2 [M+H]$^+$.

Example 17: 3-(5-cyano-4-isopropoxypyridin-2-yl)-1-(6-formyl-5-((4-methylpiperazin-1-yl)methyl)pyridin-2-yl)-1-methylurea

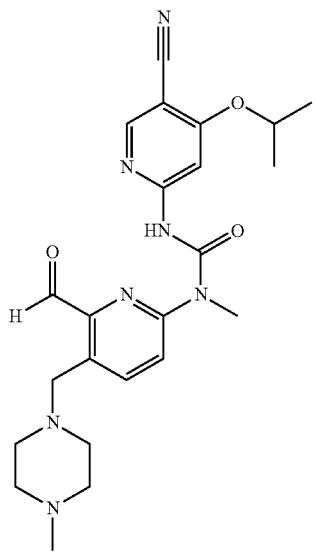 [SMILES: CC(C)Oc1cc(NC(=O)N(C)c2ccc(CN3CCN(C)CC3)c(C=O)n2)ncc1C#N]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-((4-methylpiperazin-1-yl)methyl)pyridin-2-yl)-3-(5-cyano-4-isopropoxypyridin-2-yl)-1-methylurea (Intermediate 53) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-d$_6$): δ 12.84 (s, 1H), 10.19 (s, 1H), 8.56 (s, 1H), 8.10 (d, 1H), 7.89 (m, 1H), 7.63 (d, 1H), 4.84 (septet, 1H), 3.87 (s, 2H), 3.47 (s, 3H), 3.30 (s, br, 3H), 2.58-2.07 (m, 8H), 1.39 (d, 6H). (UPLC-MS 6) t$_R$ 0.77 min; ESI-MS 452.4 [M+H]$^+$.

Example 18: 3-(5-cyano-4-isopropoxypyridin-2-yl)-1-(5-(difluoromethyl)-6-formylpyridin-2-yl)-1-methylurea

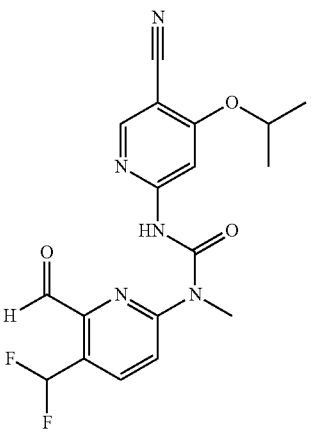 [SMILES: CC(C)Oc1cc(NC(=O)N(C)c2ccc(C(F)F)c(C=O)n2)ncc1C#N]

The title compound was prepared in an analagous manner to N-((6-(3-(5-cyano-4-((2-methoxyethyl)amino)pyridin-2-yl)-1-methylureido)-2-formylpyridin-3-yl)methyl)-N-methylacetamide (Example 15) except 3-(5-cyano-4-isopropoxypyridin-2-yl)-1-(5-(difluoromethyl)-6-(1,3-dioxolan-2-yl)pyridin-2-yl)-1-methylurea (Intermediate 56) was used in place of N-((6-(3-(5-cyano-4-((2-methoxyethyl)amino)pyridin-2-yl)-1-methylureido)-2-(1,3-dioxolan-2-yl)pyridin-3-yl)methyl)-N-methylacetamide (Intermediate 45). $^1$H NMR (400 MHz, DMSO-d$_6$): δ 12.35 (s, 1H), 10.00 (s, 1H), 8.58 (s, 1H), 8.33 (d, 1H), 7.87-7.78 (m, 2H), 7.57 (t, 1H), 4.90-4.80 (m, 1H), 3.53 (s, 3H), 1.39 (d, 6H). (UPLC-MS 7) t$_R$ 0.97/1.18 min; merged peaks with hydrate; ESI-MS 390.2 [M+H]$^+$.

Example 19: 3-(5-cyanopyridin-2-yl)-1-(6-formyl-5-((2-oxopyrrolidin-1-yl)methyl)pyridin-2-yl)-1-methylurea

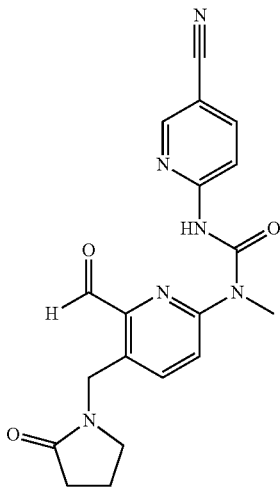 [SMILES: CN(C(=O)Nc1ccc(C#N)cn1)c1ccc(CN2CCCC2=O)c(C=O)n1]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-((2-oxopyrrolidin-1-yl)methyl)pyridin-2-yl)-3-(5-cyanopyridin-2-yl)-1-methylurea (Intermediate 57) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethyl urea (Intermediate 34). $^1$H NMR (400 MHz, DMSO-$d_6$): δ 12.74 (s, 1H), 10.12 (s, 1H), 8.79 (d, 1H), 8.25 (dd, 1H), 8.15 (d, 1H), 7.86 (d, 1H), 7.66 (d, 1H), 4.80 (s, 2H), 3.48 (s, 3H), 3.42-3.32 (m, 2H), 2.44-2.38 (m, 2H), 2.01-1.90 (m, 2H). (UPLC-MS 7) $t_R$ 0.77/0.84 min; sample dissolved in MeOH shows a double peak; ESI-MS 379.0 [M+H]$^+$.

Example 20: 3-(5-cyano-4-((2-methoxyethyl)amino)pyridin-2-yl)-1-(6-formyl-5-((2-oxopyrrolidin-1-yl)methyl)pyridin-2-yl)-1-methylurea

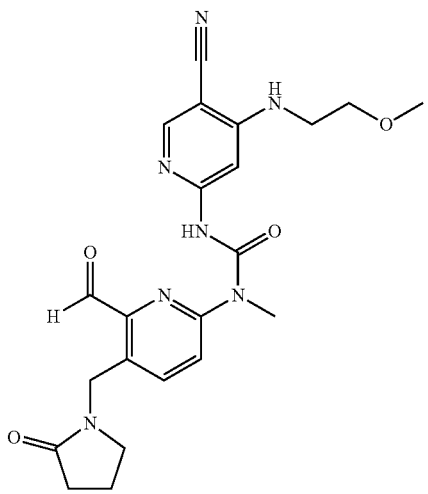 [SMILES: COCCNc1cc(NC(=O)N(C)c2ccc(CN3CCCC3=O)c(C=O)n2)ncc1C#N]

The title compound was prepared in an analagous manner to 3-(5-cyano-4-((2-methoxyethyl)amino)pyridin-2-yl)-1-(6-formyl-5-(hydroxymethyl)pyridin-2-yl)-1-((tetrahydrofuran-3-yl)methyl)urea (Example 5) except 1-(6-(1,3-dioxolan-2-yl)-5-((2-oxopyrrolidin-1-yl)methyl) pyridin-2-yl)-3-(5-cyano-4-((2-methoxyethyl)amino)pyridin-2-yl)-1-methylurea (Intermediate 60) was used in place of 1-(5-(((tert-butyldimethylsilyl)oxy)methyl)-6-(1,3-dioxolan-2-yl)pyridin-2-yl)-3-(5-cyano-4-((2-methoxyethyl)amino)pyridin-2-yl)-1-((tetrahydrofuran-3-yl)methyl)urea (Intermediate 18). $^1$H NMR (400 MHz, DMSO-$d_6$): δ 12.49 (s, 1H), 10.10 (s, 1H), 8.27 (s, 1H), 7.86 (d, 1H), 7.63 (d, 1H), 7.48 (s, 1H), 6.99 (t, br, 1H), 4.79 (s, 2H), 3.56-3.51 (m, 2H), 3.46 (s, 3H), 3.42-3.32 (m, 2H), 3.32-3.27 (m, 5H), 2.36-2.28 (m, 2H), 2.04-1.92 (m, 2H). (UPLC-MS 6) $t_R$ 0.72/0.80 min; sample dissolved in MeOH shows a double peak; ESI-MS 452.2 [M+H]$^+$.

Example 21: 3-(5-cyano-4-isopropoxypyridin-2-yl)-1-(6-formyl-5-((4-methyl-2-oxopiperazin-1-yl)methyl)pyridin-2-yl)-1-methylurea

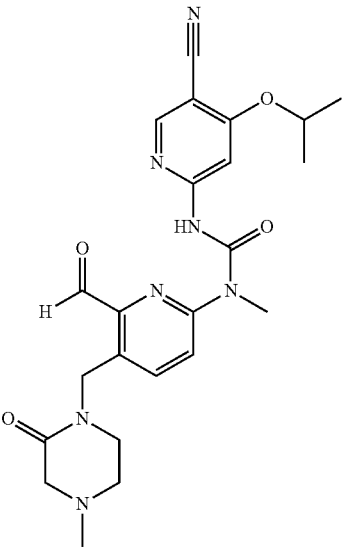 [SMILES: CC(C)Oc1cc(NC(=O)N(C)c2ccc(CN3CCN(C)CC3=O)c(C=O)n2)ncc1C#N]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-((4-methyl-2-oxopiperazin-1-yl)methyl)pyridin-2-yl)-3-(5-cyano-4-isopropoxypyridin-2-yl)-1-methylurea (Intermediate 61) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-$d_6$): δ 12.68 (s, 1H), 10.10 (s, 1H), 8.57 (s, 1H), 7.87 (s, 1H), 7.78 (d, 1H), 7.68 (d, 1H), 4.92 (s, 2H), 4.84 (septet, 1H), 3.53-3.26 (m, 5H), 3.06 (s, 2H), 2.67-2.58 (m, 2H), 2.24 (s, 6H). (UPLC-MS 6) $t_R$0.75/0.80 min; sample dissolved in MeOH shows a double peak; ESI-MS 466.3 [M+H]$^+$.

Example 22: 3-(5-cyano-4-((2-hydroxy-2-methyl-propyl)amino)pyridin-2-yl)-1-(6-formyl-5-(1-methyl-1H-pyrazol-4-yl)pyridin-2-yl)-1-methylurea

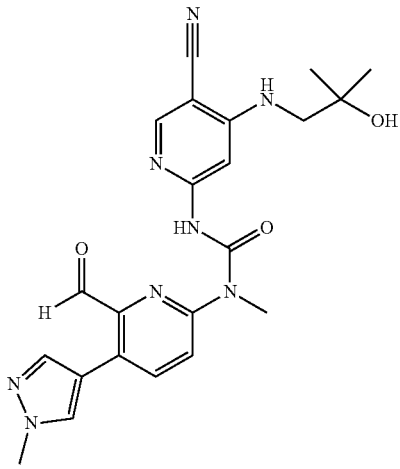 [SMILES: CN(C(=O)Nc1cc(NCC(C)(C)O)c(C#N)cn1)c1ccc(-c2cnn(C)c2)c(C=O)n1]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-(1-methyl-1H-pyrazol-4-yl)pyridin-2-yl)-3-(5-cyano-4-((2-hydroxy-2-methylpropyl)amino)pyridin-2-yl)-1-methylurea (Intermediate 66) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-$d_6$): δ 12.56 (s, 1H), 10.12 (s, 1H), 8.28 (s, 1H), 8.17 (s, 1H), 8.13 (d, 1H), 7.83 (s, 1H), 7.65 (d, 1H), 7.54 (s, 1H), 6.30 (t, br, 1H), 3.92 (s, 3H), 3.46 (s, 3H), 3.40 (d, 1H), 3.16 (d, 2H), 1.17 (d, 6H). (UPLC-MS 6) $t_R$ 0.76/0.78 min; sample dissolved in MeOH shows a double peak; ESI-MS 449.3 [M+H]$^+$.

Example 23: 3-(5-cyano-4-isopropoxypyridin-2-yl)-1-(6-formyl-5-((2-oxopyrrolidin-1-yl)methyl)pyridin-2-yl)-1-methylurea

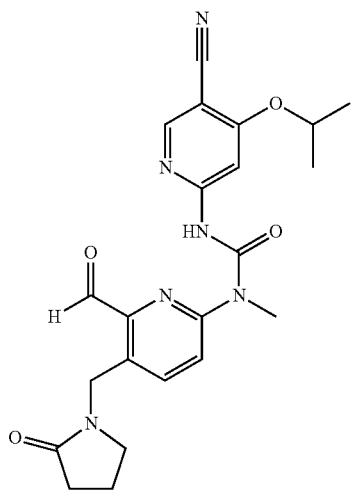 [SMILES: CC(C)Oc1cc(NC(=O)N(C)c2ccc(CN3CCCC3=O)c(C=O)n2)ncc1C#N]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-((2-oxopyrrolidin-1-yl)methyl)pyridin-2-yl)-3-(5-cyano-4-isopropoxypyridin-2-yl)-1-methylurea (Intermediate 68) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-$d_6$): δ 12.67 (s, 1H), 10.11 (s, 1H), 8.57 (s, 1H), 7.87 (s, 1H), 7.86 (d, 1H), 7.65 (d, 1H), 4.85 (septet, 1H), 4.79 (s, 2H), 3.48 (s, 3H), 3.33-3.25 (m, 2H), 2.35-2.26 (m, 2H), 2.03-1.93 (m, 2H), 1.39 (d, 6H). (UPLC-MS 6) $t_R$ 0.92/0.97 min; sample dissolved in MeOH shows a double peak; ESI-MS 437.2 [M+H]$^+$.

Example 24: 3-(5-cyano-4-((2-methoxyethyl)amino)pyridin-2-yl)-1-(6-formyl-5-((4-methyl-2-oxopiperazin-1-yl)methyl)pyridin-2-yl)-1-methylurea

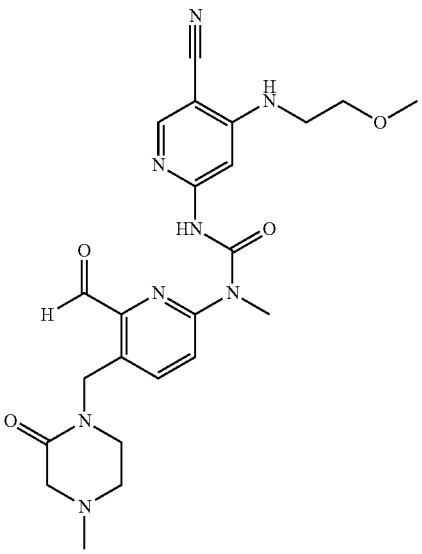 [SMILES: COCCNc1cc(NC(=O)N(C)c2ccc(CN3CCN(C)CC3=O)c(C=O)n2)ncc1C#N]

Concentrated hydrochloric acid (1.31 ml) was added to 1-(6-(1,3-dioxolan-2-yl)-5-((4-methyl-2-oxopiperazin-1-yl)methyl)pyridin-2-yl)-3-(5-cyano-4-((2-methoxyethyl)amino)pyridin-2-yl)-1-methylurea (Intermediate 69, 167 mg, 0.318 mmol) in THF (5 ml) at room temperature. After stirring for 18 h additional concentrated hydrochloric acid (1.31 ml) was added and stirring continued at room temperature for a further 1 h. The reaction mixture was partitioned between saturated aqueous NaHCO$_3$ and DCM, extracted 2× with DCM, the organic layers dried over Na$_2$SO$_4$ and evaporated. The residue was absorbed onto isolute HM-N Sorbent® and purified by normal phase chromatography using a 24 g RediSep® column, eluting with a gradient from DCM to 20% MeOH in DCM. Product containing fractions were then combined and evaporated to give the title compound. $^1$H NMR (400 MHz, DMSO-$d_6$): δ 12.46 (s, 1H), 10.09 (s, 1H), 8.26 (s, 1H), 7.78 (d, 1H), 7.66 (d, 1H), 7.47 (s, 1H), 6.96 (t, br, 1H), 4.91 (s, 2H), 3.57-3.51 (m, 2H), 3.45 (s, 3H), 3.39-3.32 (m, 2H), 3.33 15-3.26 (m, 5H), 3.05 (s, 2H), 2.66-2.59 (m, 2H), 2.24 (s, 3H). (UPLC-MS 6) $t_R$ 0.60/0.63 min; merged peaks with hydrate; ESI-MS 481.3 [M+H]$^+$.

Example 25: 3-(5-cyano-4-isopropoxypyridin-2-yl)-1-(6-formyl-5-(1-methyl-1H-pyrazol-4-yl)pyridin-2-yl)-1-methylurea

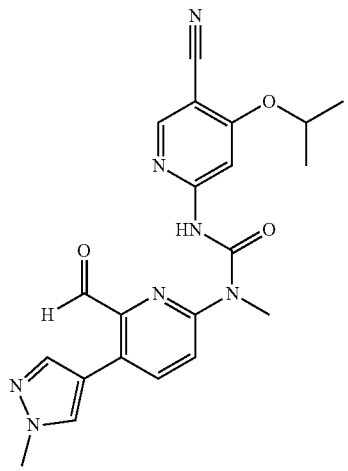 [SMILES: CC(C)Oc1cc(NC(=O)N(C)c2ccc(-c3cnn(C)c3)c(C=O)n2)ncc1C#N]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 24) except 1-(6-(1,3-dioxolan-2-yl)-5-(1-methyl-1H-pyrazol-4-yl)pyridin-2-yl)-3-(5-cyano-4-isopropoxypyridin-2-yl)-1-methylurea (Intermediate 70) was used in place of 1-(6-(1,3-dioxolan-2-yl)-5-((4-methyl-2-oxopiperazin-1-yl)methyl)pyridin-2-yl)-3-(5-cyano-4-((2-methoxyethyl)amino)pyridin-2-yl)-1-methylurea (Intermediate 69). (UPLC-MS 6) $t_R$ 1.00/1.02 min; sample dissolved in MeOH shows a double peak; ESI-MS 420.1 [M+H]$^+$.

Example 26: (racemic) 3-(5-cyano-4-isopropoxy-pyridin-2-yl)-1-(6-formyl-5-((3-methoxypyrrolidin-1-yl)methyl)pyridin-2-yl)-1-methylurea

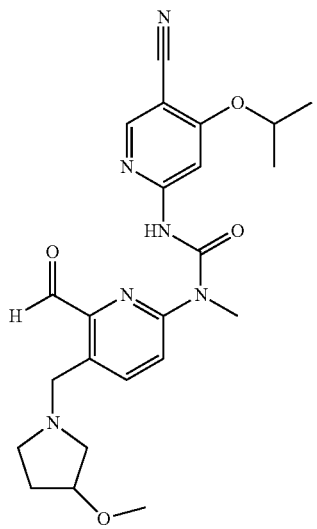 [SMILES: COC1CCN(Cc2ccc(N(C)C(=O)Nc3cc(OC(C)C)c(C#N)cn3)nc2C=O)C1]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 10) except 1-(6-(1,3-dioxolan-2-yl)-5-((3-methoxypyrrolidin-1-yl)methyl)pyridin-2-yl)-3-(5-cyano-4-isopropoxypyridin-2-yl)-1-methylurea (Intermediate 71) was used in place of 1-(6-(1,3-dioxolan-2-yl)-5-(1-methyl-1H-pyrazol-4-yl)pyridin-2-yl)-3-(5-cyano-4-((2-methoxyethyl)amino)pyridin-2-yl)-1-ethylurea (Intermediate 34). $^1$H NMR (400 MHz, DMSO-d$_6$): b 12.85 (s, 1H), 10.17 (s, 1H), 8.56 (s, 1H), 8.11 (d, 1H), 7.89 (s, 1H), 7.64 (d, 1H), 4.84 (septet, 1H), 3.99 (s, 2H), 3.91-3.82 (m, 1H), 3.47 (s, 3H), 3.15 (s, 3H), 2.74-2.58 (m, 2H), 2.48-2.39 (m, 2H), 2.01-1.92 (m, 1H), 1.69-1.61 (m, 1H), 1.38 (d, 6H). (UPLC-MS 7) $t_R$ 0.77 min; ESI-MS 453.3 [M+H]$^+$.

Example 27: 6-(2-((4-((2-methoxyethyl)amino)-5-(trifluoromethyl)pyridin-2-yl)amino)-1H-imidazol-1-yl)-3-(1-methyl-1H-pyrazol-4-yl)picolinaldehyde

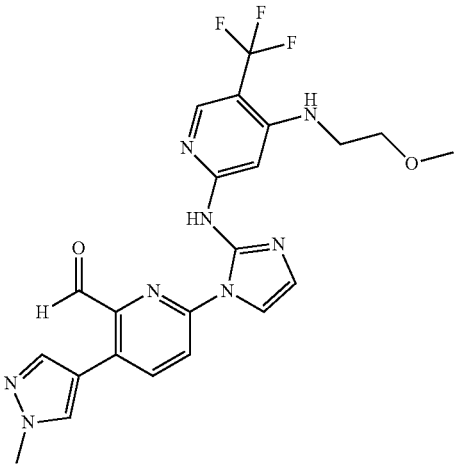 [SMILES: COCCNc1cc(Nc2nccn2-c2ccc(-c3cnn(C)c3)c(C=O)n2)ncc1C(F)(F)F]

Concentrated hydrochloric acid (0.10 ml) was added to a solution of N2-(1-(6-(1,3-dioxolan-2-yl)-5-(1-methyl-1H-pyrazol-4-yl)pyridin-2-yl)-1H-imidazol-2-yl)-N4-(2-methoxyethyl)-5-(trifluoromethyl)pyridine-2,4-diamine (Intermediate 73, 13 mg, 0.025 mmol) in THF (0.3 ml) at room temperature. Additional concentrated hydrochloric acid (0.3 ml) was added after 3 h. After stirring for 5 h, sat. aq. NaHCO$_3$ was added and the mixture extracted with DCM (3×). The combined organic layers were dried over Na$_2$SO$_4$ and evaporated. The residue was triturated with Et$_2$O to give the title compound as a light yellow solid. $^1$H NMR (400 MHz, DMSO-d$_6$) δ 11.25 (br s, 1H), 10.20 (s, 1H), 8.31 (m, 1H), 8.28 (s, 1H), 8.10-8.18 (m, 2H), 7.92 (s, 1H), 7.80-7.91 (m, 2H), 7.02 (m, 1H), 6.15 (m, 1H), 3.95 (s, 3H), 3.59 (m, 2H), 3.43 (m, 2H), 3.33 (s, 3H). (UPLC-MS 3) $t_R$ 0.73/0.84 (broad peak); ESI-MS 487.1 [M+H]$^+$.

Example 28: 6-(5-((4-((2-methoxyethyl)amino)-5-(trifluoromethyl)pyridin-2-yl)amino)-1H-pyrazol-1-yl)-3-(1-methyl-1H-pyrazol-4-yl)picolinaldehyde

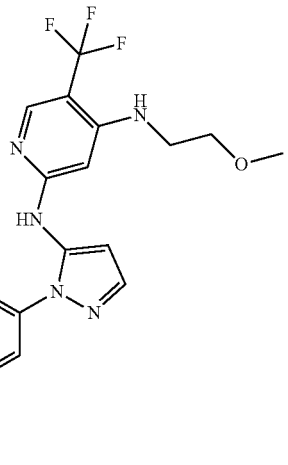

The title compound was synthesized in an analogous manner to 6-(2-((4-((2-methoxyethyl)amino)-5-(trifluoromethyl)pyridin-2-yl)amino)-1H-imidazol-1-yl)-3-(1-methyl-1H-pyrazol-4-yl)picolinaldehyde (Example 27) except N2-(1-(6-(1,3-dioxolan-2-yl)-5-(1-methyl-1H-pyrazol-4-yl)pyridin-2-yl)-1H-pyrazol-5-yl)-N4-(2-methoxyethyl)-5-(trifluoromethyl)pyridine-2,4-diamine (Intermediate 77) was used in place of N2-(1-(6-(1,3-dioxolan-2-yl)-5-(1-methyl-1H-pyrazol-4-yl)pyridin-2-yl)-1H-imidazol-2-yl)-N4-(2-methoxyethyl)-5-(trifluoromethyl)pyridine-2,4-diamine (Intermediate 73). The title compound was obtained as a light yellow solid. $^1$H NMR (400 MHz, DMSO-$d_6$) δ 12.51 (s, 1H), 10.26 (s, 1H), 8.29-8.30 (m, 2H), 8.21-8.23 (m, 2H), 7.94 (s, 1H), 7.70 (d, 1H), 6.90 (d, 1H), 6.52 (s, 1H), 6.18 (m, 1H), 3.96 (s, 3H), 3.63 (m, 2H), 3.49 (m, 2H), 3.33 (s, 3H). (UPLC-MS 3) $t_R$ 1.22; ESI-MS 487.1 [M+H]$^+$.

Example 29: 3-(5-cyano-4-isopropoxypyridin-2-yl)-1-(6-formyl-5-(pyrrolidin-1-ylmethyl)pyridin-2-yl)-1-methylurea

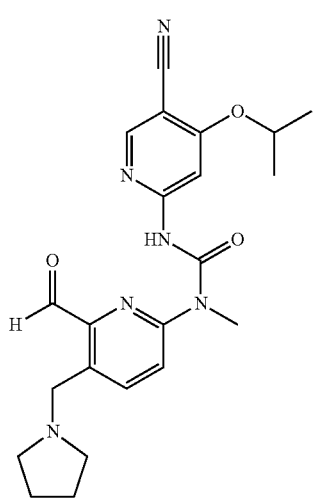 [SMILES: CC(C)Oc1cc(NC(=O)N(C)c2ccc(CN3CCCC3)c(C=O)n2)ncc1C#N]

The title compound was prepared in an analagous manner to 3-(5-cyano-4-((2-methoxyethyl)amino)pyridin-2-yl)-1-ethyl-1-(6-formyl-5-(1-methyl-1H-pyrazol-4-yl)pyridin-2-yl)urea (Example 24) except 1-(6-(1,3-dioxolan-2-yl)-5-(pyrrolidin-1-ylmethyl)pyridin-2-yl)-3-(5-cyano-4-isopropoxypyridin-2-yl)-1-methylurea (Intermediate 80) was used in place of 1-(6-(1,3-dioxolan-2-yl)-5-((4-methyl-2-oxopiperazin-1-yl)methyl)pyridin-2-yl)-3-(5-cyano-4-((2-methoxyethyl)amino)pyridin-2-yl)-1-methylurea (Intermediate 69), and the material was further purified by SFC (SFC 1). (UPLC-MS 7) $t_R$ 0.73 min; ESI-MS 423.5 [M+H]$^+$.

Example 30: 1-(5-cyano-4-isopropoxypyridin-2-yl)-3-(4-formylpyrimidin-2-yl)urea

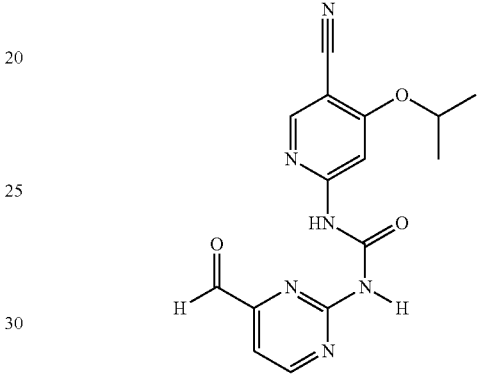

The title compound was prepared in an analogous manner to N-((6-(3-(5-cyano-4-((2-methoxyethyl)amino)pyridin-2-yl)-1-methylureido)-2-formylpyridin-3-yl)methyl)-N-methylacetamide (Example 15) except 3-(5-cyano-4-isopropoxypyridin-2-yl)-1-(4-(dimethoxymethyl)pyrimidin-2-yl)urea (Intermediate 82) was used in place of N-((6-(3-(5-cyano-4-((2-methoxyethyl)amino)pyridin-2-yl)-1-methylureido)-2-(1,3-dioxolan-2-yl)pyridin-3-yl)methyl)-N-methylacetamide (Intermediate 45). $^1$H NMR (400 MHz, DMSO-$d_6$): δ 11.76 (s, 1H), 10.95 (s, 1H), 9.88 (s, 1H), 9.04 (d, 1H), 8.57 (s, 1H), 7.92 (s, 1H), 7.57 (d, 1H), 4.90 (septet, 1H), 1.50 (d, 6H). (UPLC-MS 7) $t_R$ 0.74 min; broad peak; ESI-MS 345.2 [M+H]$^+$.

In-Vitro Biochemical Kinase Assays for FGFR4

All assays were performed in 384 well microtiter plates. Each assay plate contained 8-point serial dilutions for 40 test compounds, as well as four 8-point serial dilutions of staurosporine as reference compound, plus 16 high and 16 low controls.

Liquid handling and incubation steps were done on an Innovadyne Nanodrop Express equipped with a robotic arm (Thermo CatX, Caliper Twister II) and an incubator (Liconic STX40, Thermo Cytomat 2C450). The assay plates were prepared by addition of 50 nl per well of compound solution in 90% DMSO. The kinase reactions were started by stepwise addition of 4.5 μl per well of peptide/ATP-solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 16 mM MgCl2, 1122 μM ATP, 4 μM peptide (5-Fluo-Ahx-KKKKEEIYFFFG-NH2, Biosyntan GmbH) and 4.5 μl per well of enzyme solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 16 mM MgCl2, 6 nM FGFR4 (GST- FGFR4(388-802), produced in-house by expression in insect cells and affinity chromatography). Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-Dilution Plates:

96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master Plates:

30 µL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 µM, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

In Vitro Cellular Kinase Assays for FGFR4

As a read out for cellular FGFR4 kinase activity, an assay that measures the Tyrosine phosphorylation content on FGFR4 was developed. For this, a BaF3-Tel-FGFR4 cell line was generated: BaF3 cells were stably transduced with a retrovirus encoding a fusion protein consisting of the amino terminal portion of TEL (aa1-337) fused to the cytoplasmic domain of FGFR4, including the yuxtamembrane domain. The presence of the TEL domain mediates constitutive activation of the fused FGFR4 kinase by oligomerization, and thus autophosphorylation on the Tyrosine sites.

A MSD (Meso Scale Discovery)-based capture ELISA was developed and used as follows:

Cell treatment: 250000 BaF3-Tel-FGFR4 cells per well were seeded in 96-well tissue culture plates (Corning Cat#3359) in 40 uL of growth medium (RPMI-1640 (Amimed Cat#1-41F01-1) supplemented with 10% foetal calf serum, 10 mM HEPES, 1 mM Sodium Pyruvate, 2 mM Stable Glutamine and 1× Penicillin-Streptomycin). Using a liquid handling device (Velocity 11 Bravo, Agilent), serial 3-fold dilutions of compounds were prepared in DMSO, prediluted in growth medium, followed by transfer of 10 uL/well to the cell plates. After incubation for 1 hour at 37° C./5% CO2, 50 uL of lysis buffer (150 mM NaCl, 20 mM Tris (pH 7.5), 1 mM EDTA, 1 mM EGTA, 1% Triton X-100, 10 mM NaF, complemented with protease inhibitors (Complete Mini, Roche Cat#11836153001) and phosphatase) inhibitors (Phosphatase Inhib I, SIGMA Cat# P2850; Phosphatase Inhib II, SIGMA Cat# P5726 according to supplier instructions) was added and incubated for 30 minutes on ice with shaking at 300 rpm. Sample plates were then frozen and stored at −70° C. Following thawing on ice, the sample plates were centrifuged for 15 minutes at 1200 rpm at 6° C.

ELISA assay: Multi array 96 well plates (MSD, Cat# L15XB-3) were coated for 1 hour at room temperature with 25 uL/well of mouse anti-H-TEL antibody (Santa Cruz, Cat#sc-166835) diluted 1:400 in PBS/O. Following addition of 150 uL of 3% MSD-blocker A (Cat# $R_{93}BA$-1) in TBS-T (50 mM Tris, 150 mM NaCl, 0.02% Tweeen-20), plates were incubated for 1 hour at room temperature with shaking. Plates were then washed 3 times with 200 uL/well of TBS-T. 50 uL of the cell lysate was then transferred to the coated plate and incubated for 15 hours at 4° C., followed by 3 washes with 200 µl TBS-T/well and addition of 25 µl/well of MSD SULFOTAGGED PY20 antibody (MSD Cat# R32AP-5), diluted 1:250 in TBS-T+1% MSD Blocker A. Following Incubation for 1h at room temperature with shaking, wells were washed 3 times with 200 µl TBS-T/well. Following ition of 150 µl MSD Read Buffer (MSD, Cat# R92TC-2) stock solution diluted 1:4 with nano water, electro-chemiluminescent signal generation was immediately quantified on a SectorImager 6000 (MSD). IC50 calculation: For data analysis, the assay background was determined in wells containing medium and lysis buffer, but no cells, and the corresponding value subtracted from all data points. The effect of a particular test compound concentration on FGFR4 phosphorylation is expressed as percentage of the background-corrected electro-chemiluminescence reading obtained for cells treated with vehicle only (DMSO, 0.2% f.c.), which is set as 100. Compound concentrations leading to half-maximal signal inhibition (IC50) were determined by standard four parametric curve fitting (XLfit 5.4, IDBS).

Cell Proliferation Assay

Methylene Blue Staining Proliferation Assay (MBS):

The effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-1), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Specifically, 5000 cells/well were seeded in 96-well tissue culture plates (TPP Cat#92696) in a total media volume of 100 µl/well and increasing compound dilutions or DMSO were added 24 hours thereafter in triplicates. 72 hours after compound addition, cells were fixed by adding 25 µL/well of 20% glutaraldehyde (Sigma Aldrich Cat#G400-4) and incubated for 10 minutes at room temperature. Cells were washed three times with H₂O, 200 µL/well and stained with 100 µL/well 0.05% methylene blue (ABCR GmbH Cat# AB117904) for 10 minutes at room temperature. Cells were washed 3 times with H₂O, 200 µL/well and then lysed by adding 200 µL/well of 3% HCl (Fluka Cat#84422) for 30 minutes at room temperature with shaking. Optical density was measured at A650 nm. The concentration of compound providing 50% of proliferation inhibition with respect to DMSO-treated cells was determined (IC$_{50}$) using XLFit software.

CellTiter Glo (CTG) Assay:

The functional effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-I), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Compound-mediated suppression of cell proliferation/viability is assessed by quantification of cellular ATP levels using the CellTiter-Glo (CTG) reagent (Promega, Cat# G7573). Briefly, cells are seeded at 3'000 cells/well/80 µl fresh medium into tissue-culture-treated 96-well plates (Costar Cat#3904), followed by addition of 20 µl medium containing compound dilutions at 5-fold their final intended concentration. Dose-response effects are assessed by 3-fold serial dilutions of the test compound, starting at 10 µM. Following incubation of the cells for 3 days at 37° C. and 5% CO2, the effect of inhibitors on cell viability is quantified following addition of 50 µl CTG and luminescence measurement (integration time: 500 ms) as per vendor manual, using a correspondingly equipped multi-mode plate reader (M200Pro, TECAN, Switzerland). For data analysis, the assay background value determined in wells containing medium, but no cells, is subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% f.c.), which is set as 100%, whereas the luminescence reading for wells containing medium only, but no cells, is set as −100%. Compound concentrations leading to half-maximal growth inhibition (GI50) are determined using standard four parameter curve fitting (XLfit 5.2, IDBS, UK).

Biological Data

| Example | Biochemical FGFR4 IC$_{50}$ (nM) | Cellular BaF$_3$ FGFR4 IC$_{50}$ (nM) | HUH7 proliferation (nM) | |
|---|---|---|---|---|
| | | | MBS | CTG |
| 1 | 330 | | | |
| 2 | 6.5 | 41 | | >3000 |
| 3 | 7.4 | 91 | >3000 | |
| 4 | 1.9 | 268 | | |
| 5 | 66 | 234 | | |
| 6 | 4.7 | 140 | | |
| 7 | 5.1 | 223 | | |
| 8 | 1.6 | 737 | | |
| 9 | 1.3 | 1270 | >3000 | >3000 |
| 10 | 10 | 13 | 1089 | |
| 11 | 5.6 | 17 | | |
| 12 | 8.6 | 33 | | 2140 |
| 13 | 5.8 | 53 | | 664 |
| 14 | 3.6 | | | |
| 15 | | 4.8 | 25 | 106 |
| 16 | 2.7 | 7.7 | 51 | 90 |
| 17 | 29 | 145 | | 2760 |
| 18 | 1.9 | 25 | 191 | 463 |
| 19 | 78 | | | |
| 20 | 4.3 | 5.3 | | 100 |
| 21 | 4.8 | 6.9 | | 878 |
| 22 | 5.7 | 46 | | 1800 |
| 23 | 0.7 | 8.8 | | 118 |
| 24 | | 3.7 | | 66 |
| 25 | 6.3 | | | |
| 26 | 17 | 501 | | >3000 |
| 27 | 340 | 568 | | >3000 |
| 28 | 480 | 2640 | | 2660 |
| 29 | 250 | >3000 | | >3000 |
| 30 | 100 | 982 | | >3000 |

In addition to the above data, the following compounds were measured as >3000 nM in the indicated cellular assays: Example 22 in the HUH7 CTG; Example 28 in the BaF3 and HUH7 CTG.

Comparative Data

In vitro biochemical assays for FGFR1 (407-822), FGFR2 (406-821) and FGFR3 (411-806) were conducted in a similar manner to the in vitro biochemical assay for FGFR4 described above, using the indicated portions of the kinase domains. The following examples all produced IC$_{50}$ values >10000 nM in the biochemical FGFR1, FGFR2 and FGFR3 assays: 2, 3, 4, 11, 13, 16, 17, 18, 20, 28, 30.

As shown in the table and the comparative data presented above, the compounds of the invention are potent selective FGFR4 inhibitors.

The invention claimed is:

1. A method of treating liver cancer, comprising administering to a subject a therapeutically effective amount of a compound of formula (I):

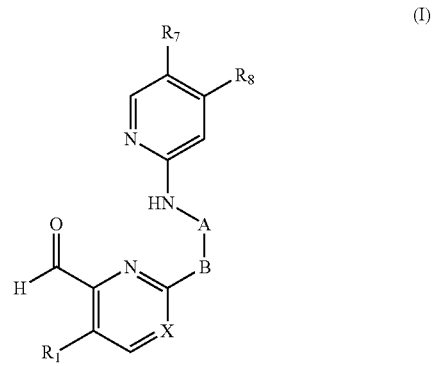

wherein

X is N or CH;

A is C(O) and B is NR$_5$ or

A and B together form part of a 5- or 6-membered aromatic ring wherein A is C and B is C or N;

$R_1$ is selected from hydrogen, hydroxy$C_1$-$C_3$alkyl, halo$C_1$-$C_3$alkyl, $CO_2H$, $CH_2NR_2R_3$, a 5-membered aromatic heterocyclic ring comprising at least one heteroatom selected from N, O or S, which ring is optionally substituted once or more than once with $C_1$-$C_3$alkyl;

$R_2$ is $C_1$-$C_3$alkyl and $R_3$ is $C(O)C_1$-$C_3$alkyl or $R_2$ and $R_3$ together with the N to which they are attached form a saturated 5- or 6-membered ring optionally comprising one additional heteroatom selected from N, O or S, which ring is optionally substituted once or more than once with $R_4$;

$R_4$ is for each occurrence independently selected from $C_1$-$C_3$alkyl, $C_1$-$C_3$alkoxy or two $R_4$ attached at the same carbon atom form an oxo group;

$R_5$ is selected from hydrogen, $C_1$-$C_3$alkyl, $C_1$-$C_3$alkoxy$C_1$-$C_3$alkyl, $(CH_2)_{0-1}$—$R_6$;

$R_6$ is a 4-, 5-, or 6-membered saturated heterocyclic ring comprising at least one heteroatom selected from N, O, or S;

$R_7$ is selected from cyano, halo$C_1$-$C_3$alkyl;

$R_8$ is selected from hydrogen, $NR_9R_{10}$, $C_1$-$C_6$alkoxy;

$R_9$ is hydrogen;

$R_{10}$ is selected from $C_1$-$C_6$alkyl, hydroxy$C_1$-$C_6$alkyl, $C_1$-$C_4$alkoxy$C_1$-$C_6$alkyl; in free form or in pharmaceutically acceptable salt form.

\* \* \* \* \*

UNITED STATES PATENT AND TRADEMARK OFFICE
CERTIFICATE OF CORRECTION

PATENT NO. : 10,786,492 B2
APPLICATION NO. : 16/211139
DATED : September 29, 2020
INVENTOR(S) : Nicole Buschmann et al.

It is certified that error appears in the above-identified patent and that said Letters Patent is hereby corrected as shown below:

On the Title Page

Item (62) and Item (30) should appear as follows:

Related U.S. Application Data
(62) Division of application No. 15/561,189, filed as application No. PCT/IB2016/051631 on Mar. 23, 2016, now Pat. No. 10,189,813.

(30) Foreign Application Priority Data
Mar. 25, 2015 (EP) .................... 15160735.5

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*